(12) United States Patent
Link

(10) Patent No.: US 9,896,722 B2
(45) Date of Patent: Feb. 20, 2018

(54) SYSTEMS FOR HANDLING MICROFLUIDIC DROPLETS

(71) Applicant: Raindance Technologies, Inc., Billerica, MA (US)

(72) Inventor: Darren Roy Link, Lexington, MA (US)

(73) Assignee: Raindance Technologies, Inc., Billerica, MA (US)

(*) Notice: Subject to any disclaimer, the term of this patent is extended or adjusted under 35 U.S.C. 154(b) by 0 days.

(21) Appl. No.: 15/415,044

(22) Filed: Jan. 25, 2017

(65) Prior Publication Data
US 2017/0183722 A1 Jun. 29, 2017

Related U.S. Application Data

(63) Continuation-in-part of application No. 13/855,318, filed on Apr. 2, 2013, now Pat. No. 9,562,837, which
(Continued)

(51) Int. Cl.
*C12Q 1/68* (2006.01)
*B01L 3/00* (2006.01)
(Continued)

(52) U.S. Cl.
CPC ...... *C12Q 1/6848* (2013.01); *B01L 3/502715* (2013.01); *B01L 3/502753* (2013.01);
(Continued)

(58) Field of Classification Search
CPC ........ C12Q 2563/159; C12Q 2565/629; C12Q 1/686; C12Q 1/00; C12Q 1/6848;
(Continued)

(56) References Cited

U.S. PATENT DOCUMENTS

2007/0141593 A1* 6/2007 Lee ................... B01L 3/502715
435/6.11

* cited by examiner

*Primary Examiner* — Jennifer Wecker
(74) *Attorney, Agent, or Firm* — Thomas C. Meyers; Brown Rudnick LLP

(57) ABSTRACT

The invention generally relates to assemblies for displacing droplets from a vessel that facilitate the collection and transfer of the droplets while minimizing sample loss. In certain aspects, the assembly includes at least one droplet formation module, in which the module is configured to form droplets surrounded by an immiscible fluid. The assembly also includes at least one chamber including an outlet, in which the chamber is configured to receive droplets and an immiscible fluid, and in which the outlet is configured to receive substantially only droplets. The assembly further includes a channel, configured such that the droplet formation module and the chamber are in fluid communication with each other via the channel. In other aspects, the assembly includes a plurality of hollow members, in which the hollow members are channels and in which the members are configured to interact with a vessel. The plurality of hollow members includes a first member configured to expel a fluid immiscible with droplets in the vessel and a second member configured to substantially only droplets from the vessel. The assembly also includes a main channel, in which the second member is in fluid communication with the main channel. The assembly also includes at least one analysis module connected to the main channel.

17 Claims, 40 Drawing Sheets

Related U.S. Application Data is a continuation-in-part of application No. 13/026,120, filed on Feb. 11, 2011, now Pat. No. 9,074,242, which is a continuation-in-part of application No. 12/504,764, filed on Jul. 17, 2009, now abandoned, said application No. 13/855,318 is a continuation-in-part of application No. 11/803,104, filed on May 11, 2007, now abandoned.

(60) Provisional application No. 61/388,937, filed on Oct. 1, 2010, provisional application No. 61/347,158, filed on May 21, 2010, provisional application No. 61/331,490, filed on May 5, 2010, provisional application No. 61/304,163, filed on Feb. 12, 2010, provisional application No. 61/081,930, filed on Jul. 18, 2008, provisional application No. 60/920,337, filed on Mar. 26, 2007, provisional application No. 60/904,293, filed on Feb. 28, 2007, provisional application No. 60/903,153, filed on Feb. 23, 2007, provisional application No. 60/899,258, filed on Feb. 2, 2007, provisional application No. 60/876,209, filed on Dec. 20, 2006, provisional application No. 60/874,640, filed on Dec. 12, 2006, provisional application No. 60/874,561, filed on Dec. 12, 2006, provisional application No. 60/873,766, filed on Dec. 8, 2006, provisional application No. 60/860,665, filed on Nov. 22, 2006, provisional application No. 60/858,279, filed on Nov. 8, 2006, provisional application No. 60/858,278, filed on Nov. 8, 2006, provisional application No. 60/856,540, filed on Nov. 3, 2006, provisional application No. 60/856,440, filed on Nov. 3, 2006, provisional application No. 60/843,374, filed on Sep. 8, 2006, provisional application No. 60/843,327, filed on Sep. 8, 2006, provisional application No. 60/841,716, filed on Sep. 1, 2006, provisional application No. 60/837,871, filed on Aug. 14, 2006, provisional application No. 60/837,695, filed on Aug. 14, 2006, provisional application No. 60/834,987, filed on Jul. 31, 2006, provisional application No. 60/833,151, filed on Jul. 24, 2006, provisional application No. 60/819,733, filed on Jul. 7, 2006, provisional application No. 60/819,734, filed on Jul. 7, 2006, provisional application No. 60/815,097, filed on Jun. 19, 2006, provisional application No. 60/808,614, filed on May 25, 2006, provisional application No. 60/799,833, filed on May 11, 2006, provisional application No. 60/799,834, filed on May 11, 2006.

(51) Int. Cl.
*C12Q 1/00* (2006.01)
*G01N 1/10* (2006.01)
*G01N 1/38* (2006.01)
*B01L 7/00* (2006.01)
*G01N 15/14* (2006.01)

(52) U.S. Cl.
CPC ... *B01L 3/502776* (2013.01); *B01L 3/502784* (2013.01); *C12Q 1/686* (2013.01); *C12Q 1/6806* (2013.01); *G01N 1/38* (2013.01); *B01L 7/525* (2013.01); *B01L 2200/027* (2013.01); *B01L 2200/0647* (2013.01); *B01L 2200/0673* (2013.01); *B01L 2200/141* (2013.01); *B01L 2300/0867* (2013.01); *C12Q 2563/159* (2013.01); *C12Q 2565/629* (2013.01); *G01N 15/147* (2013.01)

(58) Field of Classification Search
CPC ....... B01L 2200/0673; B01L 3/502715; B01L 3/502784; B01L 2200/027; B01L 2200/0647; B01L 2300/0867; B01L 3/502746; B01L 7/525; B01L 2200/141; B01L 3/502753; B01L 3/502776; G01N 15/147; G01N 1/38
See application file for complete search history.

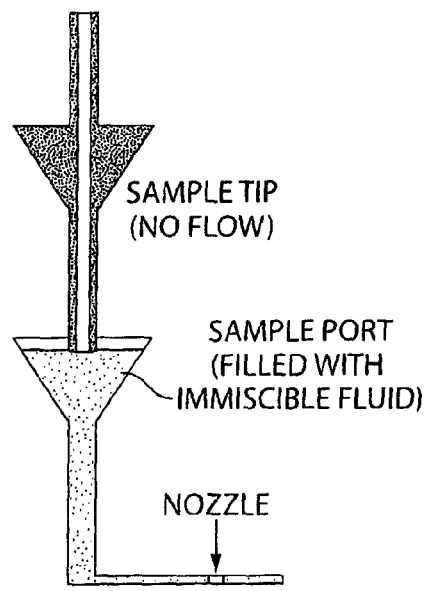
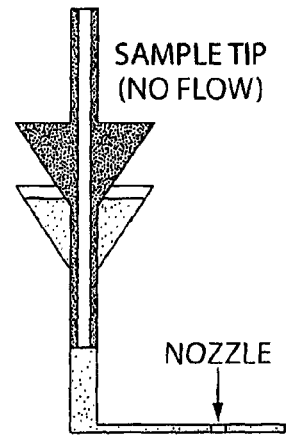
Fig. 7A          Fig. 7B
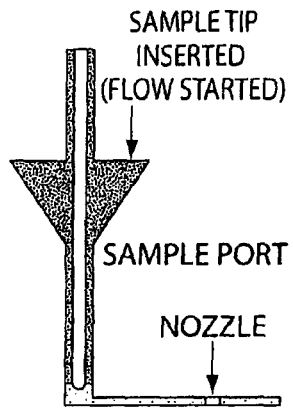
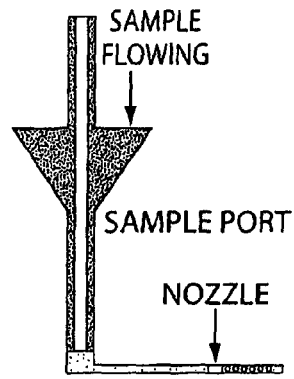
Fig. 7C          Fig. 7D
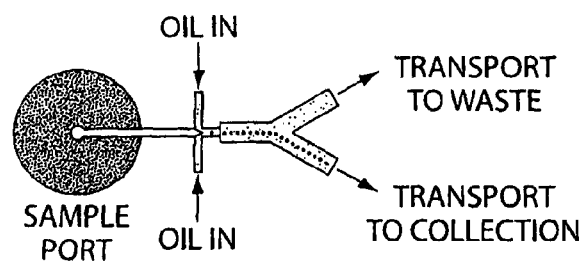
Fig. 7E BY USING OILS OF DIFFERING DENSITY WE CAN SANDWICH SMALL SAMPLES FOR LOADING ONTO THE PLS DEVICE

CAPILLARY TUBING USING THE 2-OIL SYSTEM IS A VIABLE LOADING ALTERNATIVE

ORIGINAL CONCEPT

DESIGN IMPLEMENTED

FLIPPED FLUIDIC GEOMETRY
(ASYMMETRIC FLOW GEOMETRY)

| HELICASES UNWIND DNA DUPLEXES IN THE PRESENCE OF SSB AND ACCESSORY PROTEIN | PRIMERS ANNEAL TO ssDNA | DNA POLYMERASES EXTEND THE PRIMERS; ONE DUPLEX IS AMPLIFIED TO TWO DUPLEXES | dsDNA ARE SEPARATED BY HELICASES AND THIS CHAIN REACTION REPEATS ITSELF |

SYSTEMS FOR HANDLING MICROFLUIDIC DROPLETS

RELATED APPLICATIONS

The present application is a continuation of U.S. nonprovisional patent application Ser. No. 13/855,318, filed Apr. 2, 2013, which is a continuation-in-part of U.S. nonprovisional patent application Ser. No. 11/803,104, filed May 11, 2007, which claims priority to, and the benefit of, U.S. Provisional Application Nos. 60/799,833 filed on May 11, 2006; 60/799,834 filed on May 11, 2006; 60/808,614 filed on May 25, 2006; 60/815,097 filed on Jun. 19, 2006; 60/819,733 filed on Jul. 7, 2006; 60/819,734 filed on Jul. 7, 2006; 60/841,716 filed on Sep. 1, 2006; 60/843,374 filed on Sep. 8, 2006; 60/833,151 filed on Jul. 24, 2006; 60/834,987 filed on Jul. 31, 2006; 60/837,871 filed on Aug. 14, 2006; 60/837,695 filed on Aug. 14, 2006; 60/843,327 filed on Sep. 8, 2006; 60/856,540 filed on Nov. 3, 2006; 60/856,440 filed on Nov. 3, 2006; 60/874,561 filed on Dec. 12, 2006; 60/858,279 filed on Nov. 8, 2006; 60/858,278 filed on Nov. 8, 2006; 60/874,640 filed on Dec. 12, 2006; 60/860,665 filed on Nov. 22, 2006; 60/873,766 filed on Dec. 8, 2006; 60/876,209 filed on Dec. 20, 2006; 60/899,258 filed on Feb. 2, 2007; 60/903,153 filed on Feb. 23, 2007; 60/904,293 filed on Feb. 28, 2007; 60/920,337 filed on Mar. 26, 2007. The present application is also a continuation-in-part of U.S. nonprovisional patent application Ser. No. 13/026,120, filed on Feb. 11, 2011, which claims priority to, and the benefit of U.S. Provisional Application Nos. 61/388,937, filed on Oct. 1, 2010; 61/347,158, filed on May 21; 2010, 61/331,490, filed on May 5, 2010; and 61/304,163, filed on Feb. 12, 2010. In addition, the present application is a continuation-in-part of U.S. nonprovisional patent application Ser. No. 12/504,764, which claims priority to, and the benefit of U.S. Provisional Application No. 61/081,930. The contents of each of these applications are incorporated herein by reference in their entirety.

FIELD OF THE INVENTION

The present invention generally relates to systems and methods for liquid handling.

BACKGROUND

Assays have been developed that rely on analysis of nucleic acid molecules for the presence of mutations, thus leading to early diagnosis of certain diseases, such as cancer. In a typical sample, however, any abnormal nucleic acid containing mutations of interest are often present in relatively small amounts (e.g., less than 1%) compared to the total amount of nucleic acid in the sample. Accordingly, it is difficult to detect small amounts of abnormal nucleic acid present in a sample.

The advent of PCR and real-time PCR methodologies has greatly improved the analysis of nucleic acids from both throughput and quantitative perspectives by allowing for the amplification of nucleic acids. While traditional PCR techniques typically rely on end-point or semi-quantitative analysis of amplified DNA targets via agarose gel electrophoresis, real-time PCR (or qPCR) methods are geared toward accurately quantifying exponential amplification as the reaction progresses. Digital PCR (dPCR) is an alternative quantitation method in which dilute samples are divided into many separate reactions. The distribution from background of target DNA molecules among the reactions follows Poisson statistics and at a terminal or limiting dilution, the vast majority of reactions contain either one or zero target DNA molecules.

A significant problem with PCR is sample contamination from non-target nucleic acid. Conventional PCR typically includes numerous handling steps that expose the sample to the outside environment, all which may introduce contamination into the sample. For example, a sample may be transferred by manual pipette from an open container where the sample was isolated to a PCR tube where amplification will occur. Although the tube may be closed after the addition of the sample, the PCR tube is then reopened to add the necessary reagents for amplification, again typically by manual pipette. The PCR tube is then closed and transferred to a thermocycler for the amplification process. After numerous cycles of heating and cooling, the PCR tube is removed from the thermocycler, whereupon the tube is reopened in order to remove and analyze the amplified product. Aside from exposing the sample to the outside environment whenever the container holding the sample is opened, the manual handling of the sample that occurs during the opening or closing of the tube, or during the process of manual pipetting, only increases the risk of contamination.

Since the PCR reaction is so efficient, the contaminant nucleic acid may be amplified during the PCR reaction, thus leading to biased or incorrect assay results. Contamination is especially problematic when the target nucleic acid is present in very small amounts, because the contaminant nucleic acid may easily out-compete the target nucleic acid during amplification, and thus the target nucleic acid will not be detected after the amplification reaction.

SUMMARY

The invention provides systems and methods that are designed to minimize sample contact and exposure of the sample to the surrounding environment, thereby minimizing or eliminating the introduction of contaminants into an amplification reaction. Aspects of the invention are accomplished using microfluidic assemblies. A sample including nucleic acid is loaded into a first microfluidic assembly that is used to partition the sample into partitioned portions using an immiscible fluid. Reagents for the amplification reaction are introduced to the partitioned portions, and the partitioned portions are flowed in the immiscible fluid to a chamber. The sample fluid and the immiscible fluid are of different densities, such that upon entry into the chamber, the density difference in the fluids is utilized to displace the partitioned portions from the chamber while the immiscible fluid remains in the chamber. The displaced sample portions are collected in a vessel that is sealed and transferred to a thermocycler for amplification of the nucleic acid in the partitioned portions.

Upon completion of the amplification reaction, the sealed vessel is transferred to a second assembly for analysis of the amplified nucleic acid in each partitioned portion. Connection of the vessel to the second microfluidic assembly, pierces the sealed vessel. A fluid that is immiscible with the sample portions is flowed into the vessel. That fluid has a different density than the partitioned portions of sample and thereby displaces the partitioned portions from the vessel and into at least one channel of the second assembly. The second assembly includes an analysis module that analyzes the products of the amplification reaction as they flow through the channels of the second microfluidic assembly.

Systems and methods of the invention eliminate the need for pipettes for transferring of the sample during the workflow process and substantially isolate the sample from the surrounding environment throughout the entire workflow process. Of importance is that post-amplification, the partitioned portions of sample can be transferred to the second microfluidic assembly and analyzed without exposing the partitioned portions of sample to the surrounding environment. Accordingly, the risk of contamination associated with operator handling has been eliminated. In addition, sample loss during transfer is also minimized due to the displacement of the entire sample the immiscible fluid.

In certain aspects, the first assembly includes at least one module configured for the formation of droplets. For example, the droplet formation module can include a channel adapted to carry an aqueous fluid and another channel adapted to carry a fluid immiscible with the aqueous fluid, such as an oil. The two channels are configured to intersect at a junction, such that the sample fluid is partitioned by the immiscible fluid, forming partitioned portions of sample in the immiscible fluid. In certain embodiments, reactions for the amplification reaction are pre-mixed with the sample so that the portioned portions include the reactions for the amplification reaction. In other embodiments, the first assembly also includes a module that introduces the amplification reagents to the partitioned portions. This may be accomplished by forming a droplet of amplification reagents and merging the droplet with a partitioned portion of sample. This may also be accomplished by flowing the partitioned portion of sample to interact with a stream of amplification reagents that is in fluid communication with the channel including the partitioned portions of the sample. The partitioned portion contacts the stream and a portion of the stream breaks-off into the partitioned portion. An electric field may be used to facilitate the break-off of the stream of amplification reagents.

The assembly also includes at least one chamber equipped with an outlet. The partitioned portions and immiscible fluid flow into the chamber. The partitioned portions and the immiscible fluid are of different densities. In certain embodiments, the partitioned portions are of a greater density than the immiscible fluid, so the partitioned portions sink within the chamber while the immiscible fluid rises. In other embodiments, the immiscible fluid is of a greater density than the partitioned portions, so the partitioned portions rise within the chamber while the immiscible fluid sinks. The chamber includes an outlet that is positioned to receive substantially only the partitioned portions of sample. The outlet may be positioned at any place in the chamber and it is positioned based upon the densities of the partitioned portions and the immiscible fluid. The outlet may be at the top, middle, or bottom of the chamber, and in certain embodiments, is positioned in a top portion of the chamber. In this embodiment, the partitioned portions and immiscible fluid flow in to the chamber. The immiscible fluid is of a greater density than the partitioned portions and the partitioned portions rise in the chamber while the immiscible fluid sinks. The partitioned portions then flow into the outlet.

Generally, assemblies of the invention encompass the use of any fluid that is immiscible with the partitioned portions. For example, if the partitioned portion is made from an aqueous solution, then the immiscible fluid is a fluid that is immiscible with the aqueous solution, such as an oil. Any oil that is immiscible with the partitioned portions can be used. In certain aspects, the oil is a fluorinated oil. In other aspects, the oil is a perfluorocarbon oil. Selected oils can further include one or more additives such as a surfactant or fluorosurfactant in order to stabilize the droplets. For example, the fluorosurfactant can be a perfluorinated polyether.

The selected oil is not only immiscible with the droplets, but also has a density different from that of the droplets. The density differential between the selected oil and the droplets facilitates the movement of the droplets in an upward or downward direction where they can be collected. For example, aqueous droplets placed in a chamber of fluorinated oil will tend to rise due to their lower density. Accordingly, an outlet for collecting the displaced droplets can be positioned at the top of the chamber. In another example, aqueous droplets placed in a chamber of certain mineral oils will tend to sink due to their greater density. Accordingly, an outlet for collecting the displaced droplets can be positioned at the bottom of the chamber.

In certain aspects, the outlet is connected to a slide. Partitioned portions that rise to the top of a chamber are collected at the outlet and transported down the slide to a second location. The distal end of the slide may be further equipped with an output nozzle to further facilitate the collection of partitioned portions at the second location.

The second location may include a vessel for the collection of partitioned portions. Any vessel known in the art may be used. Suitable vessels include, for example, PCR tubes, test tubes, vials, eppendorf tubes, and the like. The vessel may be coupled to the outlet to facilitate the collection of partitioned portions. In certain aspects, the outlet is sealably coupled with the vessel. By sealably coupling the vessel to the outlet, exposure to outside elements is reduced and sample contamination is further minimized. In certain aspects, the assembly includes a vessel that is pre-fitted to the output of the assembly. Because the vessel is pre-fitted to the assembly, there is no exposure of the sample to outside contaminants as the sample is displaced through the assembly into the vessel.

Once the amplification reaction is completed, the vessels are connected to a second microfluidic assembly. In certain embodiments, the second assembly includes a member configured for piercing the surface of a sealed vessel. In certain protocols, the vessel containing the partitioned portions is sealed in order to preserve the sample and minimize contamination. For instance, the lid of a PCR tube may be closed once the sample is inside the tube. Opening the lid may result in unnecessary exposure to outside contaminants. Allowing the vessel to remain sealed further reduces the risk of contamination. The distal end of the member is configured for piercing the lid such that the sample can be removed from the tube without opening it. In certain aspects, the piercing member is a spike. This second assembly may include a plurality of hollow members. Each hollow member is a channel through which fluid can flow through. The hollow members are configured to interact with the vessel to permit the removal of the droplets from the vessel while minimizing droplet handling and subsequent loss of any sample within the droplet. For example, a first hollow member may be configured to expel an immiscible fluid into the vessel while a second hollow member may be configured to receive substantially only droplets from the vessel.

In certain embodiments, the aforementioned hollow members are configured to run adjacent to the piercing member. This configuration facilitates the collection of the partitioned portions within the vessel while mitigating the risk of contamination. For example, the provided spike may be used to pierce the lid of a PCR tube containing the droplets. A first hollow member configured to run alongside the piercing member flows an immiscible fluid into the PCR tube. The displaced droplets rise to the top of the PCR tube, where they are collected by a second hollow member also configured to run alongside the piercing member.

As described above, when the immiscible fluid enters the vessel, the immiscible fluid displaces the vessel due to the density difference. Accordingly, as the first hollow member fills the vessel with the denser immiscible fluid, the droplets within the vessel will begin to rise to the top, where they can be collected by the second hollow member.

The second hollow member is connected to a main channel. As the droplets are displaced into the second hollow member, they will eventually move through the main channel. In certain aspects, the main channel is connected to an analysis module configured to analyze the characteristics of the droplets or their contents. The analysis module may include, for example, an optical detector, an electrical detector, or any combination of these. More specific components of the analysis module may include microscopes, diodes, light stimulating devices, photomultiplier tubes, processors, or any combination of these devices. Using the provided methods and assemblies, samples can be analyzed without the risk of contamination.

Assemblies of the invention are particularly suited for use in amplification reactions such as polymerase chain reaction (PCR), reverse transcription-PCR, real-time PCR, quantitative real-time PCR, digital PCR (dPCR), digital emulsion PCR (dePCR), clonal PCR, amplified fragment length polymorphism PCR (AFLP PCR), allele specific PCR, assembly PCR, asymmetric PCR (in which a great excess of primers for a chosen strand is used), colony PCR, helicase-dependent amplification (HDA), Hot Start PCR, inverse PCR (IPCR), in situ PCR, long PCR, multiplex PCR, nested PCR (uses more than one pair of primers), single-cell PCR, touchdown PCR, loop-mediated isothermal PCR (LAMP), and nucleic acid sequence based amplification (NASBA). Other amplification schemes include: Ligase Chain Reaction, Branch DNA Amplification, Rolling Circle Amplification, Circle to Circle Amplification, SPIA amplification, Target Amplification by Capture and Ligation (TACL) amplification, and RACE amplification. In particular embodiments, the amplification reaction is a PCR reaction, such as QPCR and digital PCR.

BRIEF DESCRIPTION OF THE DRAWINGS

FIGS. 7A-E illustrate a sample introduction when the sample is less dense than the fluid in the sample port, which is an alternative scheme used to introduce samples that are less dense than the oil used to emulsify the sample.

FIG. 22A shows the design using sharp tipped electrodes. FIG. 22B shows broad tipped electrodes to increase the interaction time between the droplets and the electric field (the tips could be many drop diameters long). FIG. 22C shows electrodes straddling the collection line. FIG. 22D shows electrodes on opposite sides of the main channel. FIG. 22E shows an Asymmetric Electrode Pair (the asymmetry may be present on any of the other electrode pair layouts as well).

FIG. 29A, Genomic DNA is isolated, fragmented, ligated to adapters and separated into single strands. FIG. 29B, Microscope photograph of emulsion showing droplets containing a bead and empty droplets. FIG. 29C, Scanning electron micrograph of a portion of a fiber-optic slide, showing fiber-optic cladding and wells before bead deposition. FIG. 29D, The sequencing instrument and its sub systems.

DETAILED DESCRIPTION

Figure 1:
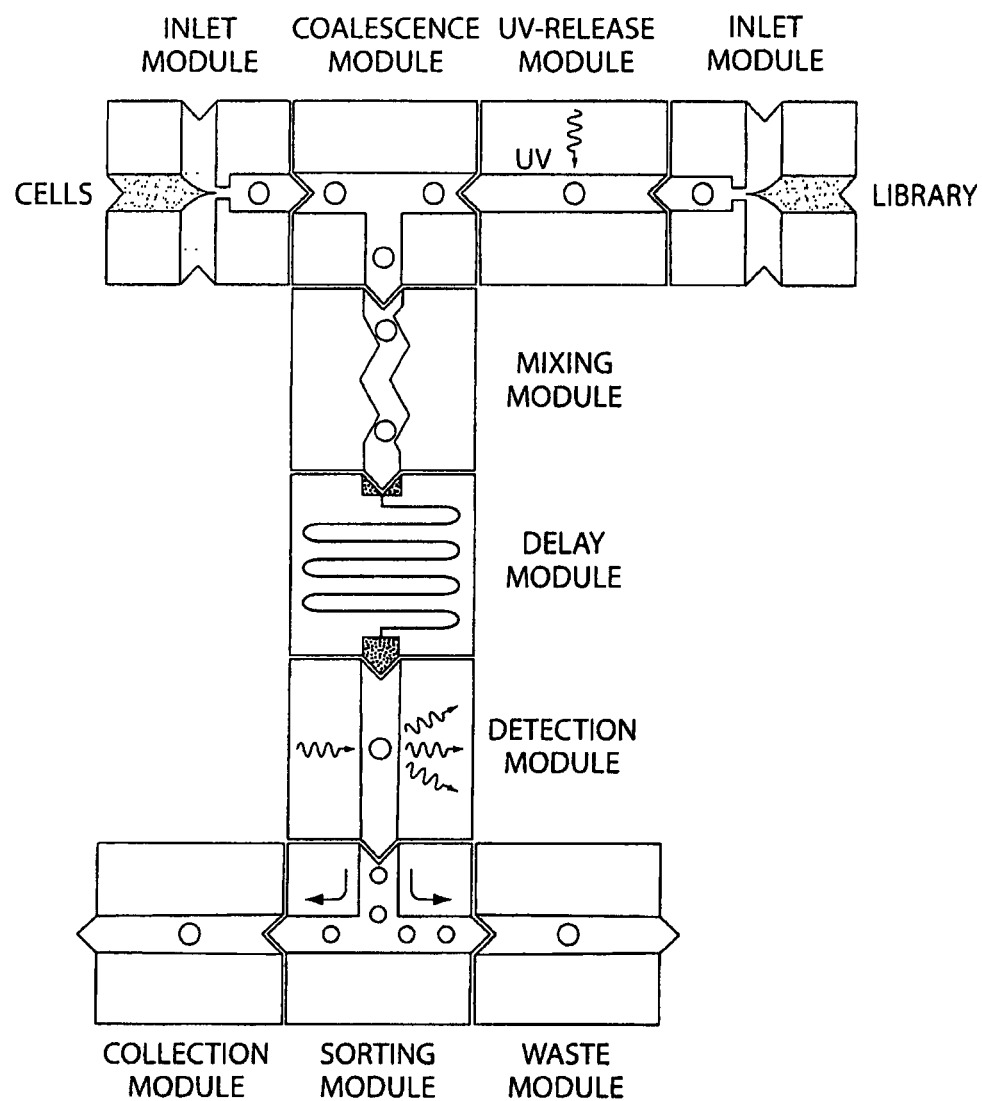
FIG. 1 is a schematic illustrating the interacting modules of a microfluidic device of the present invention.

The microfluidic devices and methods of use described herein are based on the creation and electrical manipulation of aqueous phase droplets completely encapsulated by an inert immiscible oil stream. This combination enables precise droplet generation, highly efficient, electrically addressable, droplet coalescence, and controllable, electrically addressable single droplet sorting. The microfluidic devices include one or more channels and modules. A schematic illustrating one example of interacting modules of a microfluidic substrate is shown in FIG. 1. The integration of these modules is an essential enabling technology for a droplet based, high-throughput microfluidic reactor system.

The microfluidic devices of the present invention can be utilized for numerous biological, chemical, or diagnostic applications, as described in further detail herein.

Substrates

The microfluidic device of the present invention includes one or more analysis units. An "analysis unit" is a microsubstrate, e.g., a microchip. The terms microsubstrate, substrate, microchip, and chip are used interchangeably herein. The analysis unit includes at least one inlet channel, at least one main channel, at least one inlet module, at least one coalescence module, and at least one detection module. The analysis unit can further includes one or more sorting modules. The sorting module can be in fluid communication with branch channels which are in fluid communication with one or more outlet modules (collection module or waste module). For sorting applications, at least one detection module cooperates with at least one sorting module to divert flow via a detector-originated signal. It shall be appreciated that the "modules" and "channels" are in fluid communication with each other and therefore may overlap; i.e., there may be no clear boundary where a module or channel begins or ends. A plurality of analysis units of the invention may be combined in one device. The analysis unit and specific modules are described in further detail herein.

The dimensions of the substrate are those of typical microchips, ranging between about 0.5 cm to about 15 cm per side and about 1 micron to about 1 cm in thickness. A substrate can be transparent and can be covered with a material having transparent properties, such as a glass coverslip, to permit detection of a reporter, for example, by an optical device such as an optical microscope. The material can be perforated for functional interconnects, such as fluidic, electrical, and/or optical interconnects, and sealed to the back interface of the device so that the junction of the interconnects to the device is leak-proof. Such a device can allow for application of high pressure to fluid channels without leaking.

A variety of materials and methods, according to certain aspects of the invention, can be used to form any of the described components of the systems and devices of the invention. In some cases, the various materials selected lend themselves to various methods. For example, various components of the invention can be formed from solid materials, in which the channels can be formed via molding, micromachining, film deposition processes such as spin coating and chemical vapor deposition, laser fabrication, photolithographic techniques, etching methods including wet chemical or plasma processes, and the like. See, for example, Scientific American, 248:44-55, 1983 (Angell, et al). At least a portion of the fluidic system can be formed of silicone by molding a silicone chip. Technologies for precise and efficient formation of various fluidic systems and devices of the invention from silicone are known. Various components of the systems and devices of the invention can also be formed of a polymer, for example, an elastomeric polymer such as polydimethylsiloxane ("PDMS"), polytetrafluoroethylene ("PTFE") or Teflon®, or the like.

The channels of the invention can be formed, for example by etching a silicon chip using conventional photolithography techniques, or using a micromachining technology called "soft lithography" as described by Whitesides and Xia, Angewandte Chemie International Edition 37, 550 (1998). These and other methods may be used to provide inexpensive miniaturized devices, and in the case of soft lithography, can provide robust devices having beneficial properties such as improved flexibility, stability, and mechanical strength. When optical detection is employed, the invention also provides minimal light scatter from molecule, cell, small molecule or particle suspension and chamber material.

Different components can be formed of different materials. For example, a base portion including a bottom wall and side walls can be formed from an opaque material such as silicone or PDMS, and a top portion can be formed from a transparent or at least partially transparent material, such as glass or a transparent polymer, for observation and/or control of the fluidic process. Components can be coated so as to expose a desired chemical functionality to fluids that contact interior channel walls, where the base supporting material does not have a precise, desired functionality. For example, components can be formed as illustrated, with interior channel walls coated with another material. Material used to form various components of the systems and devices of the invention, e.g., materials used to coat interior walls of fluid channels, may desirably be selected from among those materials that will not adversely affect or be affected by fluid flowing through the fluidic system, e.g., material(s) that is chemically inert in the presence of fluids to be used within the device.

Various components of the invention when formed from polymeric and/or flexible and/or elastomeric materials, and can be conveniently formed of a hardenable fluid, facilitating formation via molding (e.g. replica molding, injection molding, cast molding, etc.). The hardenable fluid can be essentially any fluid that can be induced to solidify, or that spontaneously solidifies, into a solid capable of containing and/or transporting fluids contemplated for use in and with the fluidic network. In one embodiment, the hardenable fluid comprises a polymeric liquid or a liquid polymeric precursor (i.e. a "prepolymer"). Suitable polymeric liquids can include, for example, thermoplastic polymers, thermoset polymers, or mixture of such polymers heated above their melting point. As another example, a suitable polymeric liquid may include a solution of one or more polymers in a suitable solvent, which solution forms a solid polymeric material upon removal of the solvent, for example, by evaporation. Such polymeric materials, which can be solidified from, for example, a melt state or by solvent evaporation, are well known to those of ordinary skill in the art. A variety of polymeric materials, many of which are elastomeric, are suitable, and are also suitable for forming molds or mold masters, for embodiments where one or both of the mold masters is composed of an elastomeric material. A non-limiting list of examples of such polymers includes polymers of the general classes of silicone polymers, epoxy polymers, and acrylate polymers. Epoxy polymers are characterized by the presence of a three-membered cyclic ether group commonly referred to as an epoxy group, 1,2-epoxide, or oxirane. For example, diglycidyl ethers of bisphenol A can be used, in addition to compounds based on aromatic amine, triazine, and cycloaliphatic backbones. Another example includes the well-known Novolac polymers. Non-limiting examples of silicone elastomers suitable for use according to the invention include those formed from precursors including the chlorosilanes such as methylchlorosilanes, ethylchlorosilanes, phenylchlorosilanes, etc.

Silicone polymers are preferred, for example, the silicone elastomer polydimethylsiloxane. Non-limiting examples of PDMS polymers include those sold under the trademark Sylgard by Dow Chemical Co., Midland, Mich., and particularly Sylgard 182, Sylgard 184, and Sylgard 186. Silicone polymers including PDMS have several beneficial properties simplifying formation of the microfluidic structures of the invention. For instance, such materials are inexpensive, readily available, and can be solidified from a prepolymeric liquid via curing with heat. For example, PDMSs are typically curable by exposure of the prepolymeric liquid to temperatures of about, for example, about 65° C. to about 75° C. for exposure times of, for example, about an hour. Also, silicone polymers, such as PDMS, can be elastomeric and thus may be useful for forming very small features with relatively high aspect ratios, necessary in certain embodiments of the invention. Flexible (e.g., elastomeric) molds or masters can be advantageous in this regard.

The present invention provides improved methods of bonding PDMS to incompatible media. Normal methods of bonding various materials (plastic, metals, etc) directly to materials such as PDMS, silicone, Teflon, and PEEK using traditional bonding practices (adhesives, epoxies, etc) do not work well due to the poor adhesion of the bonding agent to materials such as PDMS. Normal surface preparation by commercially available surface activators has not worked well in microfluidic device manufacturing. This problem is eliminated by treating the PDMS surface to be bonded with high intensity oxygen or air plasma. The process converts the top layer of PDMS to glass which bonds extremely well with normal adhesives. Tests using this method to bond external fluid lines to PDMS using a UV-cure adhesive (Loctite 352, 363, and others) resulted in a bond that is stronger than the PDMS substrate, resulting in fracture of the PDMS prior to failure of the bond. The present method combines high radiant flux, wavelength selection, and cure exposure time to significantly enhance the bond strength of the adhesive.

One advantage of forming structures such as microfluidic structures of the invention from silicone polymers, such as PDMS, is the ability of such polymers to be oxidized, for example by exposure to an oxygen-containing plasma such as an air plasma, so that the oxidized structures contain, at their surface, chemical groups capable of cross-linking to other oxidized silicone polymer surfaces or to the oxidized surfaces of a variety of other polymeric and non-polymeric materials. Thus, components can be formed and then oxidized and essentially irreversibly sealed to other silicone polymer surfaces, or to the surfaces of other substrates reactive with the oxidized silicone polymer surfaces, without the need for separate adhesives or other sealing means. In most cases, sealing can be completed simply by contacting an oxidized silicone surface to another surface without the need to apply auxiliary pressure to form the seal. That is, the pre-oxidized silicone surface acts as a contact adhesive against suitable mating surfaces. Specifically, in addition to being irreversibly sealable to itself, oxidized silicone such as oxidized PDMS can also be sealed irreversibly to a range of oxidized materials other than itself including, for example, glass, silicon, silicon oxide, quartz, silicon nitride, polyethylene, polystyrene, glassy carbon, and epoxy polymers, which have been oxidized in a similar fashion to the PDMS surface (for example, via exposure to an oxygen-containing plasma). Oxidation and sealing methods useful in the context of the present invention, as well as overall molding techniques, are described in the art, for example, in an article entitled "Rapid Prototyping of Microfluidic Systems and Polydimethylsiloxane," Anal. Chem., 70:474-480, 1998 (Duffy et al.), incorporated herein by reference.

Another advantage to forming microfluidic structures of the invention (or interior, fluid-contacting surfaces) from oxidized silicone polymers is that these surfaces can be much more hydrophilic than the surfaces of typical elastomeric polymers (where a hydrophilic interior surface is desired). Such hydrophilic channel surfaces can thus be more easily filled and wetted with aqueous solutions than can structures comprised of typical, unoxidized elastomeric polymers or other hydrophobic materials.

In one embodiment, a bottom wall is formed of a material different from one or more side walls or a top wall, or other components. For example, the interior surface of a bottom wall can comprise the surface of a silicon wafer or microchip, or other substrate. Other components can, as described above, be sealed to such alternative substrates. Where it is desired to seal a component comprising a silicone polymer (e.g. PDMS) to a substrate (bottom wall) of different material, the substrate may be selected from the group of materials to which oxidized silicone polymer is able to irreversibly seal (e.g., glass, silicon, silicon oxide, quartz, silicon nitride, polyethylene, polystyrene, epoxy polymers, and glassy carbon surfaces which have been oxidized). Alternatively, other sealing techniques can be used, as would be apparent to those of ordinary skill in the art, including, but not limited to, the use of separate adhesives, thermal bonding, solvent bonding, ultrasonic welding, etc.

Channels

The microfluidic substrates of the present invention include channels that form the boundary for a fluid. A "channel," as used herein, means a feature on or in a substrate that at least partially directs the flow of a fluid. In some cases, the channel may be formed, at least in part, by a single component, e.g., an etched substrate or molded unit. The channel can have any cross-sectional shape, for example, circular, oval, triangular, irregular, square or rectangular (having any aspect ratio), or the like, and can be covered or uncovered (i.e., open to the external environment surrounding the channel). In embodiments where the channel is completely covered, at least one portion of the channel can have a cross-section that is completely enclosed, and/or the entire channel may be completely enclosed along its entire length with the exception of its inlet and outlet.

An open channel generally will include characteristics that facilitate control over fluid transport, e.g., structural characteristics (an elongated indentation) and/or physical or chemical characteristics (hydrophobicity vs. hydrophilicity) and/or other characteristics that can exert a force (e.g., a containing force) on a fluid. The fluid within the channel may partially or completely fill the channel. In some cases the fluid may be held or confined within the channel or a portion of the channel in some fashion, for example, using surface tension (e.g., such that the fluid is held within the channel within a meniscus, such as a concave or convex meniscus). In an article or substrate, some (or all) of the channels may be of a particular size or less, for example, having a largest dimension perpendicular to fluid flow of less than about 5 mm, less than about 2 mm, less than about 1 mm, less than about 500 microns, less than about 200 microns, less than about 100 microns, less than about 60 microns, less than about 50 microns, less than about 40 microns, less than about 30 microns, less than about 25 microns, less than about 10 microns, less than about 3 microns, less than about 1 micron, less than about 300 nm, less than about 100 nm, less than about 30 nm, or less than about 10 nm or less in some cases. Of course, in some cases, larger channels, tubes, etc. can be used to store fluids in bulk and/or deliver a fluid to the channel. In one embodiment, the channel is a capillary.

The dimensions of the channel may be chosen such that fluid is able to freely flow through the channel, for example, if the fluid contains cells. The dimensions of the channel may also be chosen, for example, to allow a certain volumetric or linear flow rate of fluid in the channel. Of course, the number of channels and the shape of the channels can be varied by any method known to those of ordinary skill in the art. In some cases, more than one channel or capillary may be used. For example, two or more channels may be used, where they are positioned inside each other, positioned adjacent to each other, etc.

For particles (e.g., cells) or molecules that are in droplets (i.e., deposited by the inlet module) within the flow of the main channel, the channels of the device are preferably square, with a diameter between about 2 microns and 1 mm. This geometry facilitates an orderly flow of droplets in the channels. Similarly, the volume of the detection module in an analysis device is typically in the range of between about 0.1 picoliters and 500 nanoliters.

A "main channel" is a channel of the device of the invention which permits the flow of molecules, cells, small molecules or particles past a coalescence module for coalescing one or more droplets, a detection module for detection (identification) or measurement of a droplet and a sorting module, if present, for sorting a droplet based on the detection in the detection module. The main channel is typically in fluid communication with the coalescence, detection and/or sorting modules, as well as, an inlet channel of the inlet module. The main channel is also typically in fluid communication with an outlet module and optionally with branch channels, each of which may have a collection module or waste module. These channels permit the flow of molecules, cells, small molecules or particles out of the main channel. An "inlet channel" permits the flow of molecules, cells, small molecules or particles into the main channel. One or more inlet channels communicate with one or more means for introducing a sample into the device of the present invention. The inlet channel communicates with the main channel at an inlet module.

The microfluidic substrate can also comprise one or more fluid channels to inject or remove fluid in between droplets in a droplet stream for the purpose of changing the spacing between droplets.

The channels of the device of the present invention can be of any geometry as described. However, the channels of the device can comprise a specific geometry such that the contents of the channel are manipulated, e.g., sorted, mixed, prevent clogging, etc.

A microfluidic substrate can also include a specific geometry designed in such a manner as to prevent the aggregation of biological/chemical material and keep the biological/chemical material separated from each other prior to encapsulation in droplets. The geometry of channel dimension can be changed to disturb the aggregates and break them apart by various methods, that can include, but is not limited to, geometric pinching (to force cells through a (or a series of) narrow region(s), whose dimension is smaller or comparable to the dimension of a single cell) or a barricade (place a series of barricades on the way of the moving cells to disturb the movement and break up the aggregates of cells).

To prevent material (e.g., cells and other particles or molecules) from adhering to the sides of the channels, the channels (and coverslip, if used) may have a coating which minimizes adhesion. Such a coating may be intrinsic to the material from which the device is manufactured, or it may be applied after the structural aspects of the channels have been microfabricated. "TEFLON" is an example of a coating that has suitable surface properties. The surface of the channels of the microfluidic device can be coated with any anti-wetting or blocking agent for the dispersed phase. The channel can be coated with any protein to prevent adhesion of the biological/chemical sample. For example, in one embodiment the channels are coated with BSA, PEG-silane and/or fluorosilane. For example, 5 mg/ml BSA is sufficient to prevent attachment and prevent clogging. In another embodiment, the channels can be coated with a cyclized transparent optical polymer obtained by copolymerization of perfluoro (alkenyl vinyl ethers), such as the type sold by Asahi Glass Co. under the trademark Cytop. In such an embodiment, the coating is applied from a 0.1-0.5 wt % solution of Cytop CTL-809M in CT-Solv 180. This solution can be injected into the channels of a microfluidic device via a plastic syringe. The device can then be heated to about 90° C. for 2 hours, followed by heating at 200° C. for an additional 2 hours. In another embodiment, the channels can be coated with a hydrophobic coating of the type sold by PPG Industries, Inc. under the trademark Aquapel (e.g., perfluoroalkylalkylsilane surface treatment of plastic and coated plastic substrate surfaces in conjunction with the use of a silica primer layer) and disclosed in U.S. Pat. No. 5,523,162, which patent is hereby incorporated by reference.

By fluorinating the surfaces of the channels, the continuous phase preferentially wets the channels and allows for the stable generation and movement of droplets through the device. The low surface tension of the channel walls thereby minimizes the accumulation of channel clogging particulates.

The surface of the channels in the microfluidic device can be also fluorinated to prevent undesired wetting behaviors. For example, a microfluidic device can be placed in a polycarbonate dessicator with an open bottle of (tridecafluoro-1,1,2,2-tetrahydrooctyl)trichlorosilane. The dessicator is evacuated for 5 minutes, and then sealed for 2040 minutes. The dessicator is then backfilled with air and removed. This approach uses a simple diffusion mechanism to enable facile infiltration of channels of the microfluidic device with the fluorosilane and can be readily scaled up for simultaneous device fluorination.

Fluids

The microfluidic device of the present invention is capable of controlling the direction and flow of fluids and entities within the device. The term "flow" means any movement of liquid or solid through a device or in a method of the invention, and encompasses without limitation any fluid stream, and any material moving with, within or against the stream, whether or not the material is carried by the stream. For example, the movement of molecules, beads, cells or virions through a device or in a method of the invention, e.g. through channels of a microfluidic chip of the invention, comprises a flow. This is so, according to the invention, whether or not the molecules, beads, cells or virions are carried by a stream of fluid also comprising a flow, or whether the molecules, cells or virions are caused to move by some other direct or indirect force or motivation, and whether or not the nature of any motivating force is known or understood. The application of any force may be used to provide a flow, including without limitation, pressure, capillary action, electro-osmosis, electrophoresis, dielectrophoresis, optical tweezers, and combinations thereof, without regard for any particular theory or mechanism of action, so long as molecules, cells or virions are directed for detection, measurement or sorting according to the invention. Specific flow forces are described in further detail herein.

The flow stream in the main channel is typically, but not necessarily, continuous and may be stopped and started, reversed or changed in speed. A liquid that does not contain sample molecules, cells or particles can be introduced into a sample inlet well or channel and directed through the inlet module, e.g., by capillary action, to hydrate and prepare the device for use. Likewise, buffer or oil can also be introduced into a main inlet region that communicates directly with the main channel to purge the device (e.g., or "dead" air) and prepare it for use. If desired, the pressure can be adjusted or equalized, for example, by adding buffer or oil to an outlet module.

As used herein, the term "fluid stream" or "fluidic stream" refers to the flow of a fluid, typically generally in a specific direction. The fluidic stream may be continuous and/or discontinuous. A "continuous" fluidic stream is a fluidic stream that is produced as a single entity, e. g., if a continuous fluidic stream is produced from a channel, the fluidic stream, after production, appears to be contiguous with the channel outlet. The continuous fluidic stream is also referred to as a continuous phase fluid or carrier fluid. The continuous fluidic stream may be laminar, or turbulent in some cases.

Similarly, a "discontinuous" fluidic stream is a fluidic stream that is not produced as a single entity. The discontinuous fluidic stream is also referred to as the dispersed phase fluid or sample fluid. A discontinuous fluidic stream may have the appearance of individual droplets, optionally surrounded by a second fluid. A "droplet," as used herein, is an isolated portion of a first fluid that completely surrounded by a second fluid. In some cases, the droplets may be spherical or substantially spherical; however, in other cases, the droplets may be non-spherical, for example, the droplets may have the appearance of "blobs" or other irregular shapes, for instance, depending on the external environment. As used herein, a first entity is "surrounded" by a second entity if a closed loop can be drawn or idealized around the first entity through only the second entity. The dispersed phase fluid can include a biological/chemical material. The biological/chemical material can be tissues, cells, particles, proteins, antibodies, amino acids, nucleotides, small molecules, and pharmaceuticals. The biological/chemical material can include one or more labels known in the art. The label can be a DNA tag, dyes or quantum dot, or combinations thereof.

Droplets

The term "emulsion" refers to a preparation of one liquid distributed in small globules (also referred to herein as drops, droplets or NanoReactors) in the body of a second liquid. The first and second fluids are immiscible with each other. For example, the discontinuous phase can be an aqueous solution and the continuous phase can a hydrophobic fluid such as an oil. This is termed a water in oil emulsion. Alternatively, the emulsion may be a oil in water emulsion. In that example, the first liquid, which is dispersed in globules, is referred to as the discontinuous phase, whereas the second liquid is referred to as the continuous phase or the dispersion medium. The continuous phase can be an aqueous solution and the discontinuous phase is a hydrophobic fluid, such as an oil (e.g., decane, tetradecane, or hexadecane). The droplets or globules of oil in an oil in water emulsion are also referred to herein as "micelles", whereas globules of water in a water in oil emulsion may be referred to as "reverse micelles".

The fluidic droplets may each be substantially the same shape and/or size. The shape and/or size can be determined, for example, by measuring the average diameter or other characteristic dimension of the droplets. The "average diameter" of a plurality or series of droplets is the arithmetic average of the average diameters of each of the droplets. Those of ordinary skill in the art will be able to determine the average diameter (or other characteristic dimension) of a plurality or series of droplets, for example, using laser light scattering, microscopic examination, or other known techniques. The diameter of a droplet, in a non-spherical droplet, is the mathematically-defined average diameter of the droplet, integrated across the entire surface. The average diameter of a droplet (and/or of a plurality or series of droplets) may be, for example, less than about 1 mm, less than about 500 micrometers, less than about 200 micrometers, less than about 100 micrometers, less than about 75 micrometers, less than about 50 micrometers, less than about 25 micrometers, less than about 10 micrometers, or less than about 5 micrometers in some cases. The average diameter may also be at least about 1 micrometer, at least about 2 micrometers, at least about 3 micrometers, at least about 5 micrometers, at least about 10 micrometers, at least about 15 micrometers, or at least about 20 micrometers in certain cases.

As used herein, the term "NanoReactor" and its plural encompass the terms "droplet", "nanodrop", "nanodroplet", "microdrop" or "microdroplet" as defined herein, as well as an integrated system for the manipulation and probing of droplets, as described in detail herein. Nanoreactors as described herein can be 0.1-1000 μm (e.g., 0.1, 0.2 . . . 5, 10, 15, 20, 25, 30, 35, 40, 45, 50 . . . 1000), or any size within in this range. Droplets at these dimensions tend to conform to the size and shape of the channels, while maintaining their respective volumes. Thus, as droplets move from a wider channel to a narrower channel they become longer and thinner, and vice versa.

The microfluidic substrate of this invention most preferably generate round, monodisperse droplets. The droplets can have a diameter that is smaller than the diameter of the microchannel; i.e., preferably 15 to 100 μm when cells are used; or 10 to 75 μm when reagents or other chemical or biological agents are used; or 100 to 1000 μm when droplets are used for sequencing reactions such that droplets will be removed and dispensed into other collection apparatuses, such as microtiter plates or utilized in sequencing devices. Monodisperse droplets are particularly preferably, e.g., in high throughput devices and other embodiments where it is desirable to generate droplets at high frequency and of high uniformity.

The droplet forming liquid is typically an aqueous buffer solution, such as ultrapure water (e.g., 18 mega-ohm resistivity, obtained, for example by column chromatography), 10 mM Tris HCl and 1 mM EDTA (TE) buffer, phosphate buffer saline (PBS) or acetate buffer. Any liquid or buffer that is physiologically compatible with the population of molecules, cells or particles to be analyzed and/or sorted can be used. The fluid passing through the main channel and in which the droplets are formed is one that is immiscible with the droplet forming fluid. The fluid passing through the main channel can be a non-polar solvent, decane (e g., tetradecane or hexadecane), fluorocarbon oil, silicone oil or another oil (for example, mineral oil).

The dispersed phase fluid may also contain biological/chemical material (e.g., molecules, cells, or other particles) for combination, analysis and/or sorting in the device. The droplets of the dispersed phase fluid can contain more than one particle or can contain no more than one particle. For example, where the biological material comprises cells, each droplet preferably contains, on average, no more than one cell. However, in some embodiments, each droplet may contain, on average, at least 1000 cells. The droplets can be detected and/or sorted according to their contents.

The concentration (i.e., number) of molecules, cells or particles in a droplet can influence sorting efficiently and therefore is preferably optimized. In particular, the sample concentration should be dilute enough that most of the droplets contain no more than a single molecule, cell or particle, with only a small statistical chance that a droplet will contain two or more molecules, cells or particles. This is to ensure that for the large majority of measurements, the level of reporter measured in each droplet as it passes through the detection module corresponds to a single molecule, cell or particle and not to two or more molecules, cells or particles.

The parameters which govern this relationship are the volume of the droplets and the concentration of molecules, cells or particles in the sample solution. The probability that a droplet will contain two or more molecules, cells or particles ($P_{\leq 2}$) can be expressed as $$P_{\leq 2} = 1 - \{1 + [\text{cell}] \times V\} \times e^{-[\text{cell}] \times V}$$

where "[cell]" is the concentration of molecules, cells or particles in units of number of molecules, cells or particles per cubic micron ($\mu m^3$), and V is the volume of the droplet in units of $\mu m^3$.

It will be appreciated that $P_{\leq 2}$ can be minimized by decreasing the concentration of molecules, cells or particles in the sample solution. However, decreasing the concentration of molecules, cells or particles in the sample solution also results in an increased volume of solution processed through the device and can result in longer run times. Accordingly, it is desirable to minimize to presence of multiple molecules, cells or particles in the droplets (thereby increasing the accuracy of the sorting) and to reduce the volume of sample, thereby permitting a sorted sample in a reasonable time in a reasonable volume containing an acceptable concentration of molecules, cells or particles.

The maximum tolerable $P_{\leq 2}$ depends on the desired "purity" of the sorted sample. The "purity" in this case refers to the fraction of sorted molecules, cells or particles that possess a desired characteristic (e.g., display a particular antigen, are in a specified size range or are a particular type of molecule, cell or particle). The purity of the sorted sample is inversely proportional to $P_{\leq 2}$. For example, in applications where high purity is not needed or desired a relatively high $P_{\leq 2}$ (e.g., $P_{\leq 2}=0.2$) may be acceptable. For most applications, maintaining $P_{\leq 2}$ at or below about 0.1, preferably at or below about 0.01, provides satisfactory results.

The fluids used to generate droplets in microfluidic devices are typically immiscible liquids such as oil and water. These two materials generally have very different dielectric constants associated with them. These differences can be exploited to determine droplet rate and size for every drop passing through a small section of a microfluidic device. One method to directly monitor this variation in the dielectric constant measures the change in capacitance over time between a pair of closely spaced electrodes. This change in capacitance can be detected by the change in current measured in these electrodes:

$$i = V(dC/dt)$$

where i is the current, V is the voltage applied across the electrodes, and dC/dt is the change in capacitance with time. Alternatively, the capacitance can be measured directly if a time varying voltage is applied to these same electrodes: i=CdV/dt Where C is the measured capacitance, and dV/dt is the change in voltage with time. As a first approximation, the electrode pair can be determined as a parallel plate capacitor:

$$C = \in_0 k \, A/d$$

where $\in_0$ is the permittivity of free space, k is the effective dielectric constant (this changes every time a droplet passes through), A is the area of the capacitor and d is the electrode separation. The current measured in the device is then plotted as a function of time.

The fluidic droplets may contain additional entities, for example, other chemical, biochemical, or biological entities (e.g., dissolved or suspended in the fluid), cells, particles, gases, molecules, or the like. In some cases, the droplets may each be substantially the same shape or size, as discussed above. In certain instances, the invention provides for the production of droplets consisting essentially of a substantially uniform number of entities of a species therein (i.e., molecules, cells, particles, etc.). For example, about 90%, about 93%, about 95%, about 97%, about 98%, or about 99%, or more of a plurality or series of droplets may each contain the same number of entities of a particular species. For instance, a substantial number of fluidic droplets produced, e.g., as described above, may each contain 1 entity, 2 entities, 3 entities, 4 entities, 5 entities, 7 entities, 10 entities, 15 entities, 20 entities, 25 entities, 30 entities, 40 entities, 50 entities, 60 entities, 70 entities, 80 entities, 90 entities, 100 entities, etc., where the entities are molecules or macromolecules, cells, particles, etc. In some cases, the droplets may each independently contain a range of entities, for example, less than 20 entities, less than 15 entities, less than 10 entities, less than 7 entities, less than 5 entities, or less than 3 entities in some cases. In some embodiments, a droplet may contain 100,000,000 entities. In other embodiments, a droplet may contain 1,000,000 entities.

In a liquid containing droplets of fluid, some of which contain a species of interest and some of which do not contain the species of interest, the droplets of fluid may be screened or sorted for those droplets of fluid containing the species as further described below (e.g., using fluorescence or other techniques such as those described above), and in some cases, the droplets may be screened or sorted for those droplets of fluid containing a particular number or range of entities of the species of interest, e.g., as previously described. Thus, in some cases, a plurality or series of fluidic droplets, some of which contain the species and some of which do not, may be enriched (or depleted) in the ratio of droplets that do contain the species, for example, by a factor of at least about 2, at least about 3, at least about 5, at least about 10, at least about 15, at least about 20, at least about 50, at least about 100, at least about 125, at least about 150, at least about 200, at least about 250, at least about 500, at least about 750, at least about 1000, at least about 2000, or at least about 5000 or more in some cases. In other cases, the enrichment (or depletion) may be in a ratio of at least about 104, at least about 105, at least about 106, at least about 107, at least about 108, at least about 109, at least about 1010, at least about 1011, at least about 1012, at least about 1013, at least about 1014, at least about 1015, or more. For example, a fluidic droplet containing a particular species may be selected from a library of fluidic droplets containing various species, where the library may have about 100, about 103, about 104, about 105, about 106, about 107, about 108, about 109, about 1010, about 1011, about 1012, about 1013, about 1014, about 1015, or more items, for example, a DNA library, an RNA library, a protein library, a combinatorial chemistry library, etc. In certain embodiments, the droplets carrying the species may then be fused, reacted, or otherwise used or processed, etc., as further described below, for example, to initiate or determine a reaction.

Droplets of a sample fluid can be formed within the inlet module on the microfluidic device or droplets (or droplet libraries) can be formed before the sample fluid is introduced to the microfluidic device ("off chip" droplet formation). To permit effective interdigitation, coalescence and detection, the droplets comprising each sample to be analyzed must be monodisperse. As described in more detail herein, in many applications, different samples to be analyzed are contained within droplets of different sizes. Droplet size must be highly controlled to ensure that droplets containing the correct contents for analysis and coalesced properly. As such, the present invention provides devices and methods for forming droplets and droplet libraries.

Devices and Methods for Forming Sample Droplets on a Microfluidic Substrate

Figure 2A:
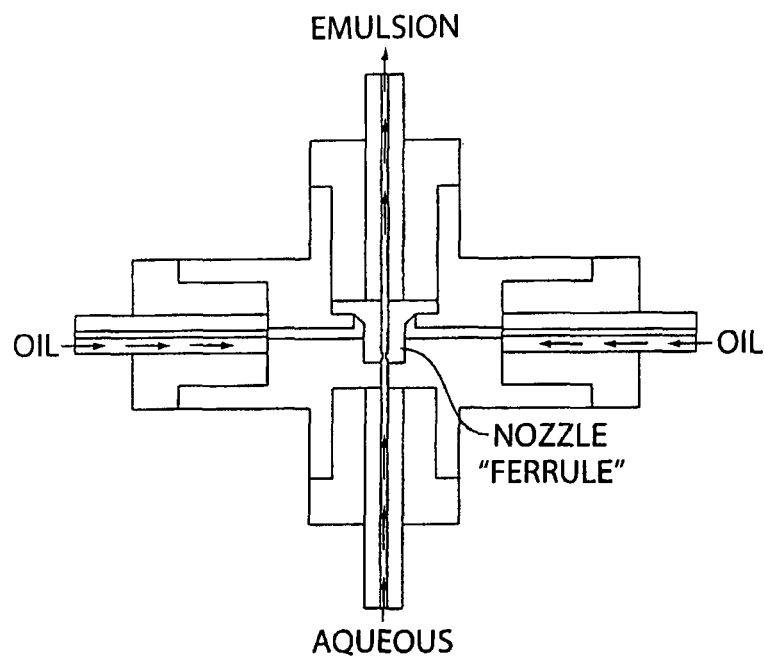
FIGS. 2A-B show dual and single oil versions of the nozzle concept using a small ferrule for the nozzle section.
Figure 2B:
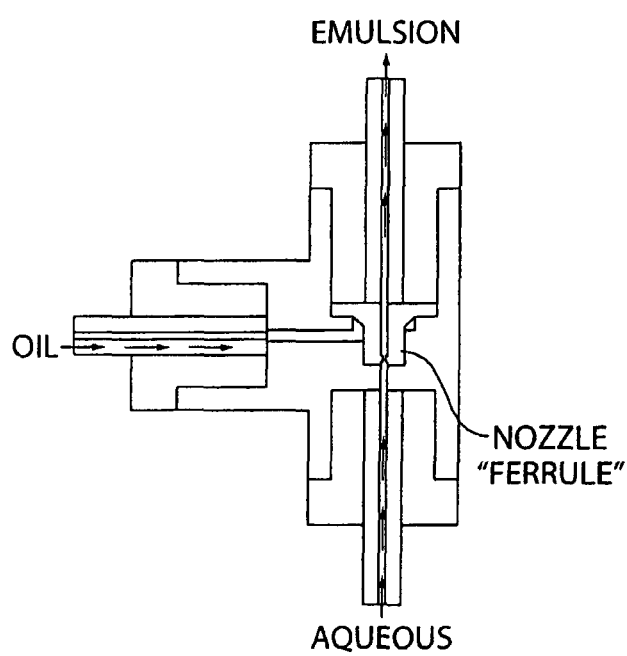
Figure 2C:
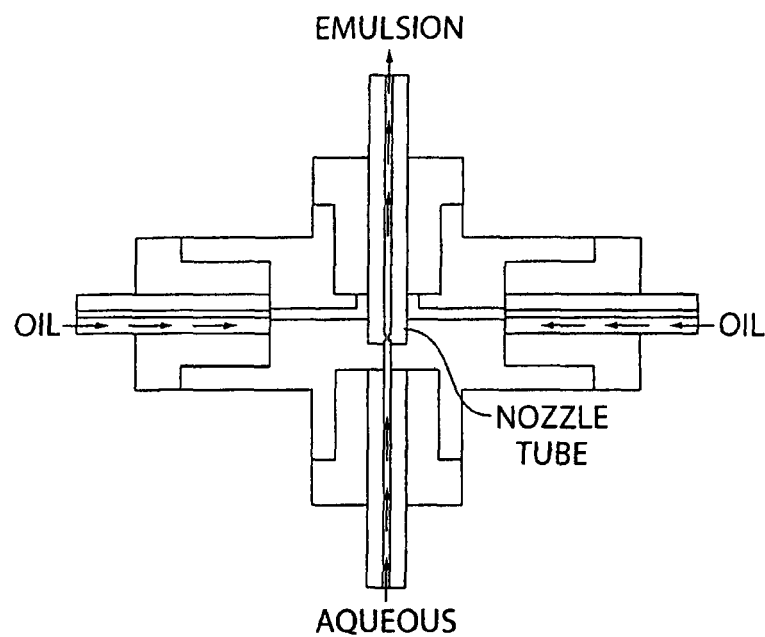
FIGS. 2C-D show the same nozzles made directly out of small bore tubing (the "nozzle" runs the entire length of the tubing).
Figure 2D:
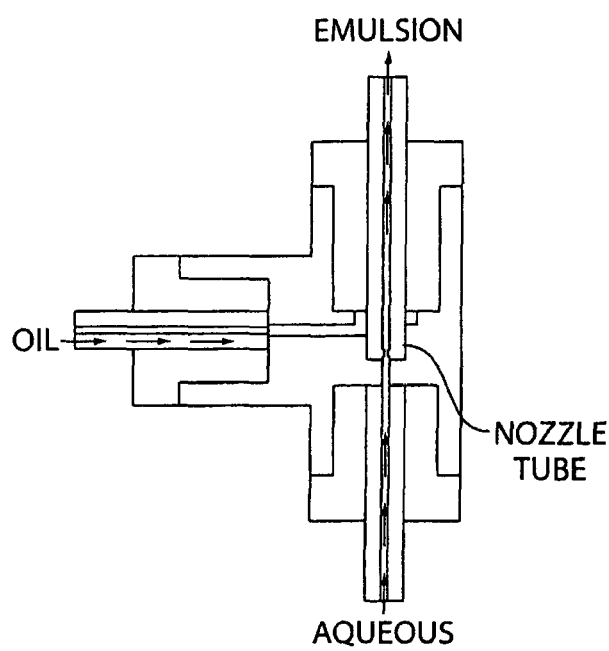
Figure 3:
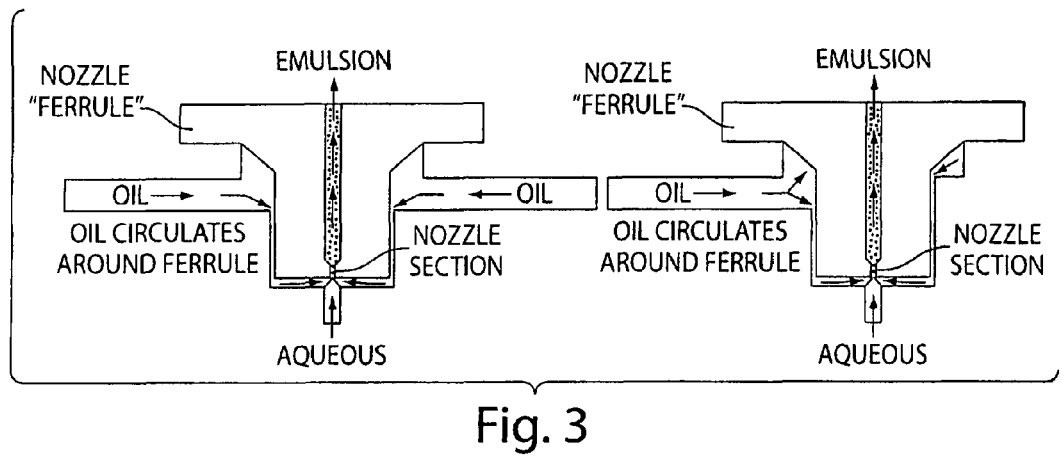
FIG. 3 shows the expansion of the nozzle ferrule concept shown in FIGS. 2A and 2B.
Figure 4:
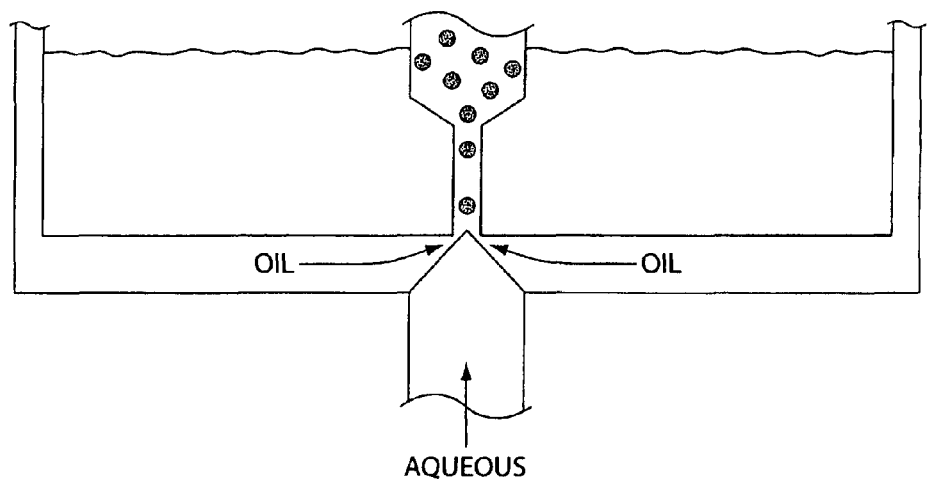
FIG. 4 shows the expansion of the nozzle section contained in the ferrule.
Figure 5A:
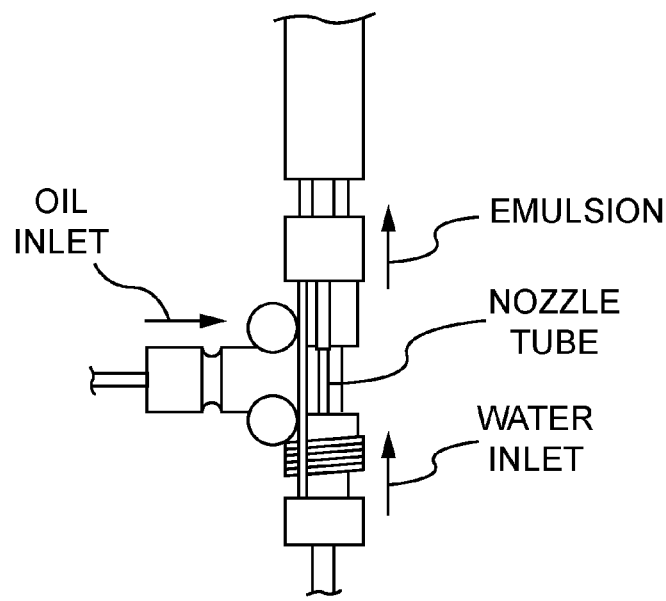
FIG. 5A shows the operation of the nozzle in Aspiration Mode.
Figure 5B:
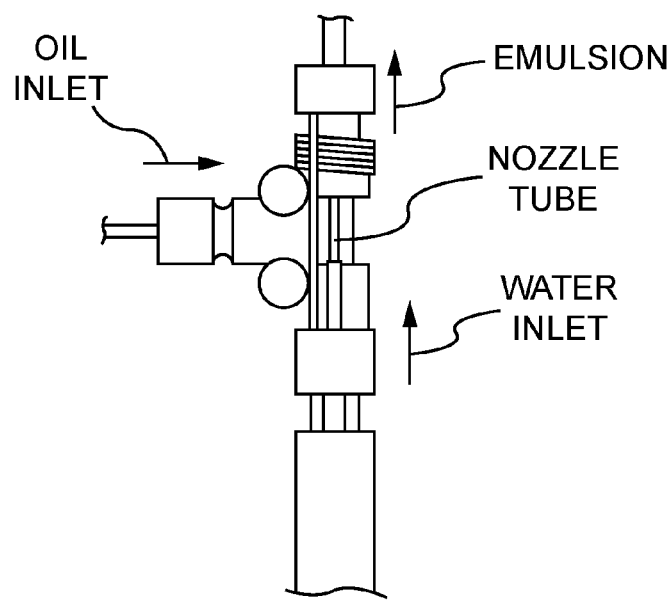
FIG. 5B shows the operation of the nozzle in Injection Mode.
Figure 6A:
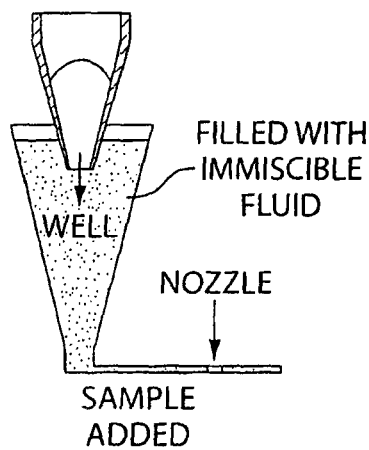
FIGS. 6A-E show a reservoir based sample emulsification where the well is initially filled with a fluid with lower density than the sample to be introduced.
Figure 6B:
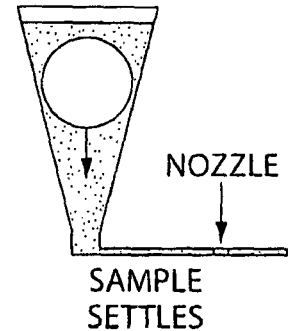
Figure 6C:
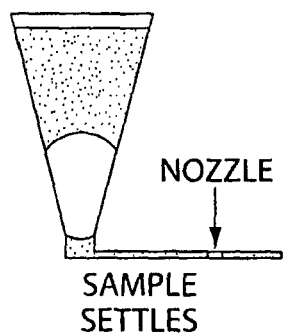
Figure 6D:
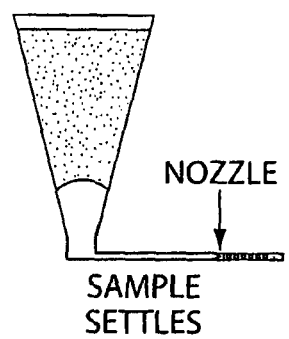
Figure 6E:
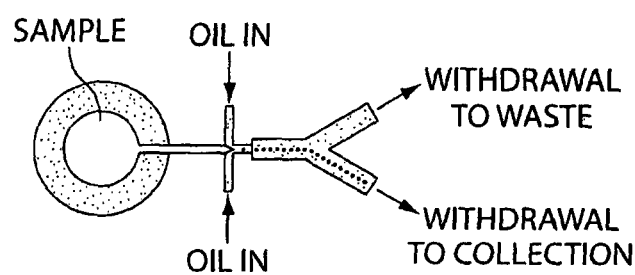

The present invention provides compositions and methods for forming sample droplet emulsions on a microfluidic substrate. The present invention also provides embedded microfluidic nozzles. In order to create a monodisperse emulsion directly from a library well, this invention would form a nozzle directly into the fitting used to connect the storage well/reservoir (e.g. syringe) to a syringe tip (e.g. capillary tubing), as shown in FIGS. 2-6. FIGS. 2A-B show dual and single oil versions of the nozzle concept using a small ferrule for the nozzle section. FIGS. 2C-D show the same Nozzles made directly out of small bore tubing (the "nozzle" runs the entire length of the tubing). Both designs can form droplets identically, although the pressure drop will be higher for the tube based nozzle (bottom). FIG. 3 shows the expansion of the nozzle ferrule concept shown in FIGS. 2A and 2B. The tube based nozzles (FIGS. 2C, 2D) function identically to this, except the "nozzle" runs the entire length of the tube instead of having a short transition. The ability to form droplets is identical in both cases. FIG. 4 shows the expansion of the nozzle section contained in the ferrule. The tee design in FIG. 2D has been built and tested, with a cross-section cut of this design shown in FIG. 5. FIG. 5A shows the operation of the nozzle in Aspiration Mode and FIG. 5B shows the operation of the nozzle in Injection Mode. The droplets formed are approximately 45 um in diameter, and were formed from PCR mix (210 ul/hr) and SpectraSyn-10 (600 ul/hr). Other tests have been demonstrated with Spectrasyn-2 and PCR mix. The droplets are traveling in 300 um wide×260 um deep channels. The Nozzle tube used was 100 um in diameter, and the fluids used were PCR Mix and Spectrasyn-10 with surfactant.

Since the flow is three dimensional, under this design surface wetting effects are minimized. The nozzle can be made from one or two oil lines providing constant flow of oil into the nozzle, a connection to the capillary tubing, and a connection to the storage well/reservoir (e.g. syringe). The high resolution part of the nozzle can be made out of a small bore tubing or a small, simple part molded or stamped from an appropriate material (Teflon®, plastic, metal, etc). If necessary, the nozzle itself could be formed into the tip of the ferrule using post mold processing such as laser ablation or drilling.

This nozzle design eliminates the surface wetting issues surrounding the quasi-2D flow associated with typical microfluidic nozzles made using soft lithography or other standard microfluidic chip manufacturing techniques. This is because the nozzle design is fully 3-dimensional, resulting is a complete isolation of the nozzle section from the continuous aqueous phase. This same design can also be used for generation of emulsions required for immediate use, where the aqueous line would be attached directly to a syringe and the outlet of the nozzle would be used to transport the emulsion to the point of use (e.g. into a microfluidic PCR chip, delay line, etc).

In another embodiment, the present invention provides compositions and methods to directly emulsify library elements from standard library storage geometries (e.g. 96 well plates, etc). In order to create a monodisperse emulsion from fluids contained in a library well plate, this invention would include microfluidic based nozzles manufactured simultaneously with an appropriately designed fluidic interconnect or well. FIGS. 6A-E and 7A-E present two possible approaches to interface with the nozzle.

FIGS. 6A-E show a reservoir based sample emulsification. In FIGS. 6A-E, the well is initially filled with a fluid with lower density than the sample to be introduced. The operation of this device would be very similar to the device described above, with the exception that the sample would be introduced into a port instead of being directly aspirated from a sample well. This could either be emulsification oil obtained directly from the nozzle, or a different material that is loaded or flowing into the well automatically. The oil lines would begin flowing at their prescribed rates (FIG. 6e), while the collection or waste port would begin withdrawing at a rate corresponding to the total oil flow plus the desired sample flow. Once the flow has been established, the sample would be introduced into the port either manually (e.g. a pipette) or with a robotic sample handling system. The sample volume permitted would be dependent on the port volume. Since the sample is more dense than the fluid in the well, it would settle into the bottom of the well and be transported to the nozzle (FIGS. 6a-6d). During this time, either the waste (used during startup only if transients cause problems) or the collection port would be withdrawing emulsified sample and stored. When the sample is completely emulsified the next sample would be introduced and the process repeated. If washing steps are required between runs, the washing fluids would be withdrawn into the waste line. If the pressure drop across the nozzle would cause cavitation on collection then an optional pressurization of the input well can be utilized.

FIGS. 7A-E shows sample introduction when the sample is less dense than the fluid in the sample port. FIGS. 7A-E depicts an alternative scheme that could be used to introduce samples that are less dense than the oil used to emulsify the sample. As with the concept in FIG. 1, the process of introducing the sample into the port could be run either manually or with a robotic sampling system. In this concept, the sample port could be filled with the emulsification oil through backflow from the nozzle prior to introduction of the sample (FIG. 7a). If this oil is not appropriate, the port can be filled from the top with a different immiscible fluid that might have more desirable properties than the emulsification oil (e.g. better wetting, less surfactant, etc). This second immiscible fluid could be introduced during startup and flow continuously into the port when the sample tip is not inserted. Keeping the sample port filled with fluid will prevent air entrainment during startup and should improve transient performance.

Figure 8:
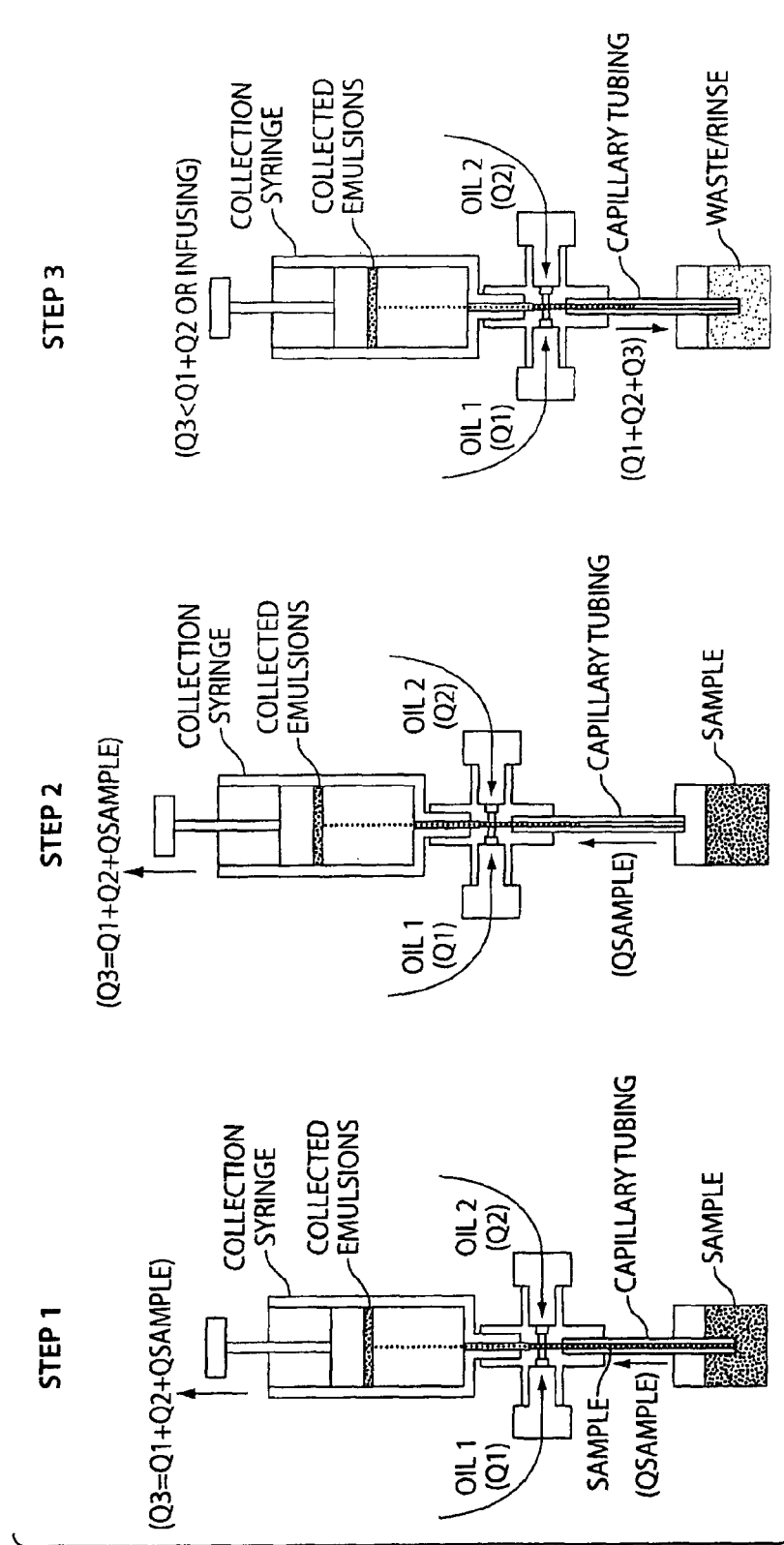
FIG. 8 illustrates a nozzle that formed directly into the fitting used to connect the collection syringe to a syringe tip (e.g. capillary tubing) in order to create a monodisperse emulsion directly from a library well. Step 1 shows the aspiration of the sample can be accomplished by running the collection syringe in withdrawal mode at a flow rate (Q3) above the flow rate of the two oil syringes. Step 2 shows the appropriate volume of sample loaded into the capillary tubing, and the capillary tubing would be removed from the sample well, an air bubble, and possibly a cleaning solution would be aspirated. Step 3 shows when almost all of the sample has been emulsified, the collection syringe withdrawal rate would either be reduced below the oil flow rates, stopped, or set to infuse at some nominal rate.

If the sample tip is connected to a pump capable of driving the sample into the device, it could be started up as the tip is inserted into the device (7b-c). When used with this sort of sample introduction, the device could be run identically to the "normal" operation of our devices, including having the "transport to waste" line (7e) not connected to a pump. If the sample tip loading pump is not capable of accurately forcing the flow (i.e. not connected to a suitable pump), the back end of the tip could be connected to a valve that would open to either atmospheric pressure (or possibly a pressurized gas supply) when the tip is fully inserted into the port. In order to prevent air entrainment into the sample tip and device, this connection could be made through a reservoir filled with the desired immiscible liquid. In either case, the device would run identically to the one described above and shown in FIGS. 6A-E. FIGS. 7A-E also show another possible configuration of the aspiration probe assembly used for the device in FIGS. 6A-E Methods for Forming Sample Droplet Emulsions Prior to Injection on a Microfluidic Substrate The present invention also provides compositions and methods for creating emulsion of the sample fluid (e.g. droplets) prior to the introduction of the sample fluid into the microfluidic devices of the present invention. More specifically, the methods are directed to the creating sample droplet emulsions "off chip", for example in a syringe. In order to create a monodisperse emulsion directly from a library well, a nozzle is formed directly into the fitting used to connect the collection syringe to a syringe tip (e.g. capillary tubing), as shown in FIG. 8. The nozzle can be made from one or two oil lines providing constant flow of oil into the nozzle, a connection to the capillary tubing, and a connection to the collection syringe. Aspiration of the sample can be accomplished by running the collection syringe in withdrawal mode at a flow rate (Q3) above the flow rate of the two oil syringes (Step 1 in FIG. 8). The difference in flow would correspond to the flow rate aspirated from the sample well. When the appropriate volume of sample has been loaded into the capillary tubing, the capillary tubing would be removed from the sample well, an air bubble, and possibly a cleaning solution would be aspirated (Step 2 in FIG. 8). When almost all of the sample has been emulsified, the collection syringe withdrawal rate would either be reduced below the oil flow rates, stopped, or set to infuse at some nominal rate (Step 3 in FIG. 8). The remaining sample, air, cleaning solution, etc, left in the capillary would be flushed back out into a cleaning well and the outside of the capillary would be cleaned at the "wash station." When the capillary is completely clean, the process would repeat for the next library element. The nozzle can be formed through using small bore tubing (glass, Teflon®, PEEK tubing or capillaries) or micro-fabrication or molding processes such as PDMS soft lithography, glass etching, hot embossing, or similar high resolution fabrication technology.

The present apparatus can be readily adapted for clinical applications or work where cross contamination must be eliminated, since the region from the nozzle to the syringe are isolated from the sample stream (e.g., the oil wets these surfaces and keeps the sample from directly contacting aqueous sample). The aspiration tip can be designed as a disposable item (like a robotic sampler aspiration tips) and automatically replaced between samples.

Multiple nozzle/syringe pairs can be operated in parallel, thus increasing throughput. This allows simultaneous sampling of multiple wells/samples during a single process step. Each sample can be collected into a separate syringe.

Other methods for forming sample droplet emulsions and emulsion libraries "off chip" are described in Example 1.

Methods for Minimizing Sample Volume Loss

As described herein, a significant problem when working with very small amounts of reagents comes from the losses associated with dead volumes found in the storage containers and transport lines. As an example, if 50 microliters of a material is injected into a 254 micron internal diameter capillary tube, a 75 cm long tube would consume about 38 microliters of the material (~75%). To address this problem, the present invention provides compositions and methods which eliminates the problems associated with dead volume and reagent waste when working with extremely small volumes of reagents.

Figure 9:
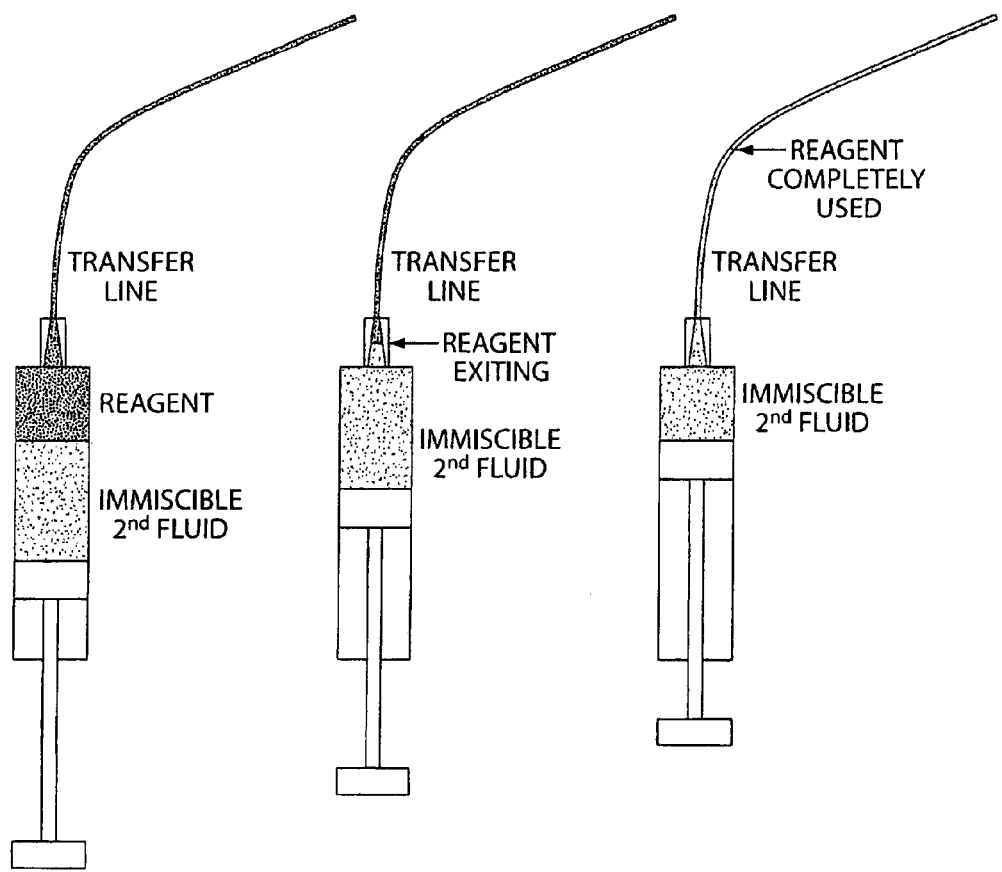
FIGS. 9A-C illustrate a two phase system where the reagent is injected on top of the 2nd, immiscible phase. (FIG. A) During injection, prior to transition from 1st phase to 2nd phase. (FIG. B) 2nd phase just entering the transfer lines. (FIG. C) 2nd phase has completely filled the transfer line and pushed the entire volume of reagent through the system.

In one embodiment, the primary reagents (sample) is combined with a second, immiscible phase in the storage container (e.g. a syringe or other reservoir). This second phase is used to push the entire amount of the first phase into the system with no significant losses. More specifically, when two immiscible fluids are combined in a reservoir, the two fluids will tend to separate into layers as long as the densities of the materials are different. If the fluid of interest (e.g., sample fluid) is closest to the exit of the reservoir, it will be the first to leave when the reservoir is emptied (the exit can be on either the top or bottom, depending on the density difference). Once the reagent has been pumped out of the reservoir, the second phase will follow. This second phase will then push the first phase completely through the system without any sample fluid loss. As an example of this, oil and water (the reagent) would be combined in a syringe. If the oil is denser than the water, the syringe would be oriented with its exit face up, if the oil were less dense, then the syringe would be face down. The oil would be chosen such that the materials of interest in the reagent are not soluble in the oil phase. FIGS. 9A-C show one example of this approach when a syringe is used as the reservoir and the second phase is denser than the reagent phase. If the reagent were more dense, then the syringe orientation would be reversed (i.e. the exit would be facing downward in the figure). Specifically, FIGS. 9A-C show a two phase system where the reagent is injected on top of the second, immiscible phase: (FIG. A) During injection, prior to transition from first phase to second phase, (FIG. B) second phase just entering the transfer line, (FIG. C) second phase has completely filled the transfer line and pushed the entire volume of reagent through the system.

Figure 10:
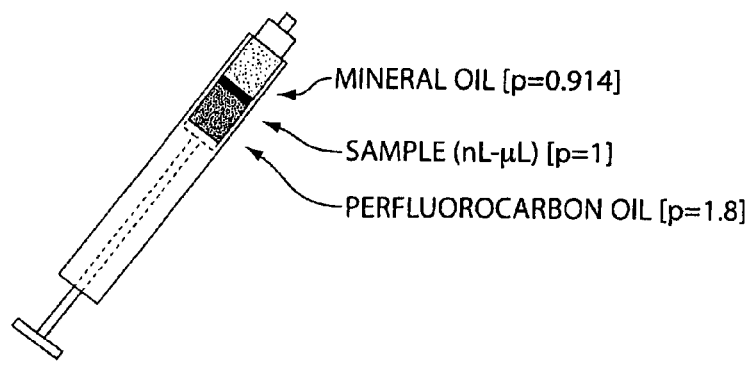
FIG. 10 illustrates sandwiching an ultra-small volume of fluid (i.e., sub-nanoliter) between two solutions having different densities.

Alternatively, a sample solution is sandwiched between two immiscible liquids, wherein one liquid has a density greater than the sample density, and the second liquid has a density less than the sample density. Referring to FIG. 10, the sample (density 1.0) can be layered between perflourocarbon oil (density 1.8) and mineral oil (density 0.914). Ideally, when the device is being used to analyze biological reactions the immiscible solutions do not inhibit the reactions of the sample, nor are any test molecules in the sample or the sample itself soluble in either immiscible fluid. The less dense fluid (in FIG. 10, the mineral oil) can be used to 'prime the pump' and remove any air or dead-space that occurs during normal injection. The sample then rises to the injection point after the mineral oil. It is further contemplated that the methods disclosed herein would also work for gases. The gases and/or liquids can be miscible, but of different densities such that they are layered on top each other in a manner that prevents their mixing.

Solid or Semi-Solid Phase Droplets

The present invention also provides solid phase particles and methods for the forming solid phase particles on a microfluidic device for downstream analysis. The solid phase particles can be used for various biological or chemical analysis (e.g., DNA or protein analyses). For DNA analysis, post amplification encapsulation of amplicons occurs within a gel or polymer matrix prior to breaking of the droplet emulsion. Amplification reactions within droplets using one of several amplification type methods (described in further detail herein), including, but not limited to; PCR, Rolling Circle Amplification (RCA), Nucleic Acid Sequence Based Amplification (NASBA), ligase chain reaction, etc. followed by encapsulation/solidification of the amplified reaction within the droplets by either polymerizing the droplets using chemical or physical means.

A physical means might be termed 'gelling' whereby one incorporates low temperature agarose within the droplet during formulation and keeping the droplet above the solidification temperature until one desires the droplet to solidify.

A chemical means might be termed 'polymerization' whereby one combines (if needed) the droplet with a polymerizing solution and then polymerizing the droplet using either a polymerization initiator (for example free radicals) or a means such as UV light. Some other means of gelling or polymerization include matragel, polyacrylamide, mixed polysaccharides, etc. Some example initiators can be temperature, UV irradiation, etc.

In a further example, one of the DNA primers used for amplification can be attached to one of the molecules that will form the polymerized matrix. Attachment can be through a direct chemical attachment, or through a secondary attachment such as biotin-streptavidin attachment. In this example, the DNA will become physically attached to the formed solid-phase that occurs after solidification of the droplet. Using one of several gelling or polymerizing methods it should be possible to further manipulate these droplets.

One could also either exchange or wash away unincorporated nucleotides, primers and exchange buffers so as to remove the initial amplification buffers, polymerases, etc. In an example of further droplet manipulation wherein one of the strands is polymerized from an attached DNA amplification primer, one could treat the polymerized or gelled droplet with a base solution to disassociate the two DNA strands and elute, from the gelled or polymerized droplet, the unattached strand.

For protein analysis, proteins can be either trapped within, or attached to the gel or polymer matrix. If attached, it can be through a covalent linkage or through an affinity tag, for example his6 or avi-tag. The proteins can be added to droplets containing gel or polymer reagent, or they can be formulated along with the gel or polymerization reagent. Variations that include both are also possible. The protein can be added to the droplets. Additionally, it is possible to add DNA to the droplet and allow in vitro transcription/translation to synthesize the protein.

The droplets can be kept in liquid form on the microfluidic device and either gelled or polymerized upon removal, or can be gelled or polymerized within the droplets anywhere on the device after the droplets have been formed.

In an example, multiple plasmids are formulated into a droplet along with an in vitro transcription/translation reaction. Genes, encoded by the plasmids, are translated and transcribed to protein molecules. The protein molecules attach to the polymer via an avi-tag, the droplets are allowed to gel and the plasmid molecules become 'fixed' or 'trapped' within the gel. The gelled droplets are collected, the emulsion is broken and the solidified droplets collected and washed. As an example application, DNA is amplified within a droplet wherein one primer is physically attached to a polymer monomer. The droplet is then combined with a droplet containing the enzymes DNA polymerase, luciferase and sulfurylase. The merged droplets are allowed to gel or polymerize, they are collected, and if needed, washed. These washed gelled droplets can then used for a DNA sequencing reaction.

Surfactants

The fluids used in the invention may contain one or more additives, such as agents which reduce surface tensions (surfactants). Surfactants can include Tween, Span, fluorosurfactants, and other agents that are soluble in oil relative to water. In some applications, performance is improved by adding a second surfactant to the aqueous phase. Surfactants can aid in controlling or optimizing droplet size, flow and uniformity, for example by reducing the shear force needed to extrude or inject droplets into an intersecting channel. This can affect droplet volume and periodicity, or the rate or frequency at which droplets break off into an intersecting channel. Furthermore, the surfactant can serve to stabilize aqueous emulsions in fluorinated oils from coalescing.

The droplets may be coated with a surfactant. Preferred surfactants that may be added to the continuous phase fluid include, but are not limited to, surfactants such as sorbitan-based carboxylic acid esters (e.g., the "Span" surfactants, Fluka Chemika), including sorbitan monolaurate (Span 20), sorbitan monopalmitate (Span 40), sorbitan monostearate (Span 60) and sorbitan monooleate (Span 80), and perfluorinated polyethers (e.g., DuPont Krytox 157 FSL, FSM, and/or FSH). Other non-limiting examples of non-ionic surfactants which may be used include polyoxyethylenated alkylphenols (for example, nonyl-, p-dodecyl-, and dinonylphenols), polyoxyethylenated straight chain alcohols, polyoxyethylenated polyoxypropylene glycols, polyoxyethylenated mercaptans, long chain carboxylic acid esters (for example, glyceryl and polyglyceryl esters of natural fatty acids, propylene glycol, sorbitol, polyoxyethylenated sorbitol esters, polyoxyethylene glycol esters, etc.) and alkanolamines (e.g., diethanolamine-fatty acid condensates and isopropanolamine-fatty acid condensates). In addition, ionic surfactants such as sodium dodecyl sulfate (SDS) may also be used. However, such surfactants are generally less preferably for many embodiments of the invention. For instance, in those embodiments where aqueous droplets are used as nanoreactors for chemical reactions (including biochemical reactions) or are used to analyze and/or sort biomaterials, a water soluble surfactant such as SDS may denature or inactivate the contents of the droplet.

The carrier fluid can be an oil (e.g., decane, tetradecane or hexadecane) or fluorocarbon oil that contains a surfactant (e.g., a non-ionic surfactant such as a Span surfactant) as an additive (preferably between about 0.2 and 5% by volume, more preferably about 2%). A user can preferably cause the carrier fluid to flow through channels of the microfluidic device so that the surfactant in the carrier fluid coats the channel walls.

In one embodiment, the fluorosurfactant can be prepared by reacting the perflourinated polyether DuPont Krytox 157 FSL, FSM, or FSH with aqueous ammonium hydroxide in a volatile fluorinated solvent. The solvent and residual water and ammonia can be removed with a rotary evaporator. The surfactant can then be dissolved (e.g., 2.5 wt %) in a fluorinated oil (e.g., Flourinert (3M)), which then serves as the continuous phase of the emulsion.

Driving Forces

The invention can use pressure drive flow control, e.g., utilizing valves and pumps, to manipulate the flow of cells, particles, molecules, enzymes or reagents in one or more directions and/or into one or more channels of a microfluidic device. However, other methods may also be used, alone or in combination with pumps and valves, such as electro-osmotic flow control, electrophoresis and dielectrophoresis (Fulwyer, Science 156, 910 (1974); Li and Harrison, Analytical Chemistry 69, 1564 (1997); Fiedler, et al. Analytical Chemistry 70, 1909-1915 (1998); U.S. Pat. No. 5,656,155). Application of these techniques according to the invention provides more rapid and accurate devices and methods for analysis or sorting, for example, because the sorting occurs at or in a sorting module that can be placed at or immediately after a detection module. This provides a shorter distance for molecules or cells to travel, they can move more rapidly and with less turbulence, and can more readily be moved, examined, and sorted in single file, i.e., one at a time.

Positive displacement pressure driven flow is a preferred way of controlling fluid flow and dielectrophoresis is a preferred way of manipulating droplets within that flow. The pressure at the inlet module can also be regulated by adjusting the pressure on the main and sample inlet channels, for example, with pressurized syringes feeding into those inlet channels. By controlling the pressure difference between the oil and water sources at the inlet module, the size and periodicity of the droplets generated may be regulated. Alternatively, a valve may be placed at or coincident to either the inlet module or the sample inlet channel connected thereto to control the flow of solution into the inlet module, thereby controlling the size and periodicity of the droplets. Periodicity and droplet volume may also depend on channel diameter, the viscosity of the fluids, and shear pressure.

Without being bound by any theory, electro-osmosis is believed to produce motion in a stream containing ions e.g. a liquid such as a buffer, by application of a voltage differential or charge gradient between two or more electrodes. Neutral (uncharged) molecules or cells can be carried by the stream. Electro-osmosis is particularly suitable for rapidly changing the course, direction or speed of flow. Electrophoresis is believed to produce movement of charged objects in a fluid toward one or more electrodes of opposite charge, and away from one on or more electrodes of like charge. Where an aqueous phase is combined with an oil phase, aqueous droplets are encapsulated or separated from each other by oil. Typically, the oil phase is not an electrical conductor and may insulate the droplets from the electro-osmotic field. In this example, electro-osmosis may be used to drive the flow of droplets if the oil is modified to carry or react to an electrical field, or if the oil is substituted for another phase that is immiscible in water but which does not insulate the water phase from electrical fields.

Dielectrophoresis is believed to produce movement of dielectric objects, which have no net charge, but have regions that are positively or negatively charged in relation to each other. Alternating, non-homogeneous electric fields in the presence of droplets and/or particles, such as cells or molecules, cause the droplets and/or particles to become electrically polarized and thus to experience dielectrophoretic forces. Depending on the dielectric polarizability of the particles and the suspending medium, dielectric particles will move either toward the regions of high field strength or low field strength. For example, the polarizability of living cells depends on their composition, morphology, and phenotype and is highly dependent on the frequency of the applied electrical field. Thus, cells of different types and in different physiological states generally possess distinctly different dielectric properties, which may provide a basis for cell separation, e.g., by differential dielectrophoretic forces. Likewise, the polarizability of droplets also depends upon their size, shape and composition. For example, droplets that contain salts can be polarized. According to formulas provided in Fiedler, et al. Analytical Chemistry 70, 1909-1915 (1998), individual manipulation of single droplets requires field differences (inhomogeneities) with dimensions close to the droplets.

The term "dielectrophoretic force gradient" means a dielectrophoretic force is exerted on an object in an electric field provided that the object has a different dielectric constant than the surrounding media. This force can either pull the object into the region of larger field or push it out of the region of larger field. The force is attractive or repulsive depending respectively on whether the object or the surrounding media has the larger dielectric constant.

Manipulation is also dependent on permittivity (a dielectric property) of the droplets and/or particles with the suspending medium. Thus, polymer particles, living cells show negative dielectrophoresis at high-field frequencies in water. For example, dielectrophoretic forces experienced by a latex sphere in a 0.5 MV/m field (10 V for a 20 micron electrode gap) in water are predicted to be about 0.2 piconewtons (pN) for a 3.4 micron latex sphere to 15 pN for a 15 micron latex sphere (Fiedler, et al. Analytical Chemistry 70, 1909-1915 (1998)). These values are mostly greater than the hydrodynamic forces experienced by the sphere in a stream (about 0.3 pN for a 3.4 micron sphere and 1.5 pN for a 15 micron sphere). Therefore, manipulation of individual cells or particles can be accomplished in a streaming fluid, such as in a cell sorter device, using dielectrophoresis. Using conventional semiconductor technologies, electrodes can be microfabricated onto a substrate to control the force fields in a microfabricated sorting device of the invention. Dielectrophoresis is particularly suitable for moving objects that are electrical conductors. The use of AC current is preferred, to prevent permanent alignment of ions. Megahertz frequencies are suitable to provide a net alignment, attractive force, and motion over relatively long distances. See U.S. Pat. No. 5,454,472.

Radiation pressure can also be used in the invention to deflect and move objects, e.g. droplets and particles (molecules, cells, particles, etc.) contained therein, with focused beams of light such as lasers. Flow can also be obtained and controlled by providing a pressure differential or gradient between one or more channels of a device or in a method of the invention. Molecules, cells or particles (or droplets containing molecules, cells or particles) can be moved by direct mechanical switching, e.g., with on-off valves or by squeezing the channels. Pressure control may also be used, for example, by raising or lowering an output well to change the pressure inside the channels on the chip. See, e.g., the devices and methods described U.S. Pat. No. 6,540,895. These methods and devices can further be used in combination with the methods and devices described in pending U.S. Patent Application Publication No. 20010029983 and 20050226742. Different switching and flow control mechanisms can be combined on one chip or in one device and can work independently or together as desired.

Inlet Module

The microfluidic device of the present invention includes one or more inlet modules. An "inlet module" is an area of a microfluidic substrate device that receives molecules, cells, small molecules or particles for additional coalescence, detection and/or sorting. The inlet module can contain one or more inlet channels, wells or reservoirs, openings, and other features which facilitate the entry of molecules, cells, small molecules or particles into the substrate. A substrate may contain more than one inlet module if desired. Different sample inlet channels can communicate with the main channel at different inlet modules. Alternately, different sample inlet channels can communication with the main channel at the same inlet module. The inlet module is in fluid communication with the main channel. The inlet module generally comprises a junction between the sample inlet channel and the main channel such that a solution of a sample (i.e., a fluid containing a sample such as molecules, cells, small molecules (organic or inorganic) or particles) is introduced to the main channel and forms a plurality of droplets. The sample solution can be pressurized. The sample inlet channel can intersect the main channel such that the sample solution is introduced into the main channel at an angle perpendicular to a stream of fluid passing through the main channel. For example, the sample inlet channel and main channel intercept at a T-shaped junction; i.e., such that the sample inlet channel is perpendicular (90 degrees) to the main channel. However, the sample inlet channel can intercept the main channel at any angle, and need not introduce the sample fluid to the main channel at an angle that is perpendicular to that flow. The angle between intersecting channels is in the range of from about 60 to about 120 degrees. Particular exemplary angles are 45, 60, 90, and 120 degrees.

Embodiments of the invention are also provided in which there are two or more inlet modules introducing droplets of samples into the main channel. For example, a first inlet module may introduce droplets of a first sample into a flow of fluid in the main channel and a second inlet module may introduce droplets of a second sample into the flow of fluid in main channel, and so forth. The second inlet module is preferably downstream from the first inlet module (e.g., about 30 µm). The fluids introduced into the two or more different inlet modules can comprise the same fluid or the same type of fluid (e.g., different aqueous solutions). For example, droplets of an aqueous solution containing an enzyme are introduced into the main channel at the first inlet module and droplets of aqueous solution containing a substrate for the enzyme are introduced into the main channel at the second inlet module. Alternatively, the droplets introduced at the different inlet modules may be droplets of different fluids which may be compatible or incompatible. For example, the different droplets may be different aqueous solutions, or droplets introduced at a first inlet module may be droplets of one fluid (e.g., an aqueous solution) whereas droplets introduced at a second inlet module may be another fluid (e.g., alcohol or oil).

Droplet Interdigitation

Particular design embodiments of the microfluidic device described herein allow for a more reproducible and controllable interdigitation of droplets of specific liquids followed by pair-wise coalescence of these droplets, described in further detail herein. The droplet pairs can contain liquids of different compositions and/or volumes, which would then combine to allow for a specific reaction to be investigated. The pair of droplets can come from any of the following: (i) two continuous aqueous streams and an oil stream; (ii) a continuous aqueous stream, an emulsion stream, and an oil stream, or (iii) two emulsion streams and an oil stream. The term "interdigitation" as used herein means pairing of droplets from separate aqueous streams, or from two separate inlet nozzles, for eventual coalescence.

The nozzle designs described herein enhance the interdigitation of droplets and further improves coalescence of droplets due to the better control of the interdigitation and smaller distance between pairs of droplets. The greater control over interdigitation allows for a perfect control over the frequency of either of the droplets. To obtain the optimum operation, the spacing between droplets and coupling of the droplets can be adjusted by adjusting flow of any of the streams, viscosity of the streams, nozzle design (including orifice diameter, the channel angle, and post-orifice neck of the nozzle).

Reservoir/Well

A device of the invention can include a sample solution reservoir or well or other apparatus for introducing a sample to the device, at the inlet module, which is typically in fluid communication with an inlet channel. Reservoirs and wells used for loading one or more samples onto the microfluidic device of the present invention, include but are not limited to, syringes, cartridges, vials, eppendorf tubes and cell culture materials (e.g., 96 well plates). A reservoir may facilitate introduction of molecules or cells into the device and into the sample inlet channel of each analysis unit.

Fluidic Interconnects

The microfluidic device can include a syringe (or other glass container) that is treated with a vapor or solution of an appropriate PEG-silane to effect the surface PEG functionalization. The purpose for treating the walls of glass containers (e.g., syringes) with a PEG functionality is to prevent biological adhesion to the inner walls of the container, which frustrates the proper transfer of biological/chemical materials into the microfluidic device of the present invention. The inlet channel is further connected to a means for introducing a sample to said device. The means can be a well or reservoir. The means can be temperature controlled. The inlet module may also contain a connector adapted to receive a suitable piece of tubing, such as liquid chromatography or HPLC tubing, through which a sample may be supplied. Such an arrangement facilitates introducing the sample solution under positive pressure in order to achieve a desired infusion rate at the inlet module.

The interconnections, including tubes, must be extremely clean and make excellent bonding with the PDMS surface in order to allow proper operation of the device. The difficulty in making a fluidic connection to a microfluidic device is primarily due to the difficulty in transitioning from a macroscopic fluid line into the device while minimizing dead volume. In order to minimize contamination and leakage and allow for greater reproducibility and reliability are improved, tubes and interconnects for the PDMS slab can be cured in place. The tubes and interconnects can be placed in position by applying a UV-cured adhesive to allow for holding the tubes in place on the silicone wafer. Once the tubes are placed in position, PDMS can be poured over the wafer and cured. The cured PDMS, along with the tubes in place, can be peeled off of the silicone wafer easily. This process can be applied to fluidics channels as well as other connection channels. Once the adhesive is applied onto the wafer, the process will allow for quick templating of PDMS slabs with exact reproducibility of channel locations and cleanliness. Tubes of any size can be implemented for this process. This process allows for less stress on the interconnection joints and smaller interconnection footprints in the device (see, for example, PCT/US2006/02186 filed on Jun. 1, 2006; PCT/US2006/021280 filed on Jun. 1, 2006 and PCT/US2006/021380 filed on Jun. 1, 2006, each of which is incorporated by reference in their entirety for all purposes).

The tubing side of the interconnect can be mounted into a retaining block that provides precise registration of the tubing, while the microfluidic device can be positioned accurately in a carrier that the retaining block would align and clamp to. The total dead volume associated with these designs would be critically dependent on how accurately the two mating surfaces could be positioned relative to each other. The maximum force required to maintain the seal would be limited by the exact shape and composition of the sealing materials as well as the rigidity and strength of the device itself. The shapes of the mating surfaces can be tailored to the minimal leakage potential, sealing force required, and potential for misalignment. By way of non-limiting example, the single ring indicated in can be replaced with a series of rings of appropriate cross-sectional shape.

Reservoirs and wells used for loading one or more samples onto the microfluidic device of the present invention, include but are not limited to, syringes, cartridges, vials, eppendorf tubes and cell culture materials (e.g., 96 well plates) as described above. One of the issues to be resolved in loading samples into the inlet channel at the inlet module of the substrate is the size difference between the loading means or injection means, e.g., capillary or HPLC tubing and the inlet channel. It is necessary to create an interconnect and loading method which limits leaks and minimizes dead volume and compliance problems. Several devices and methods described in further detail herein address and solve these art problems.

Self-Aligning Fluidic Interconnects

The present invention includes one or more inlet modules comprising self-aligning fluidic interconnects proximate to one or more inlet channels to improve the efficiency of sample loading and/or injection.

Figure 11:
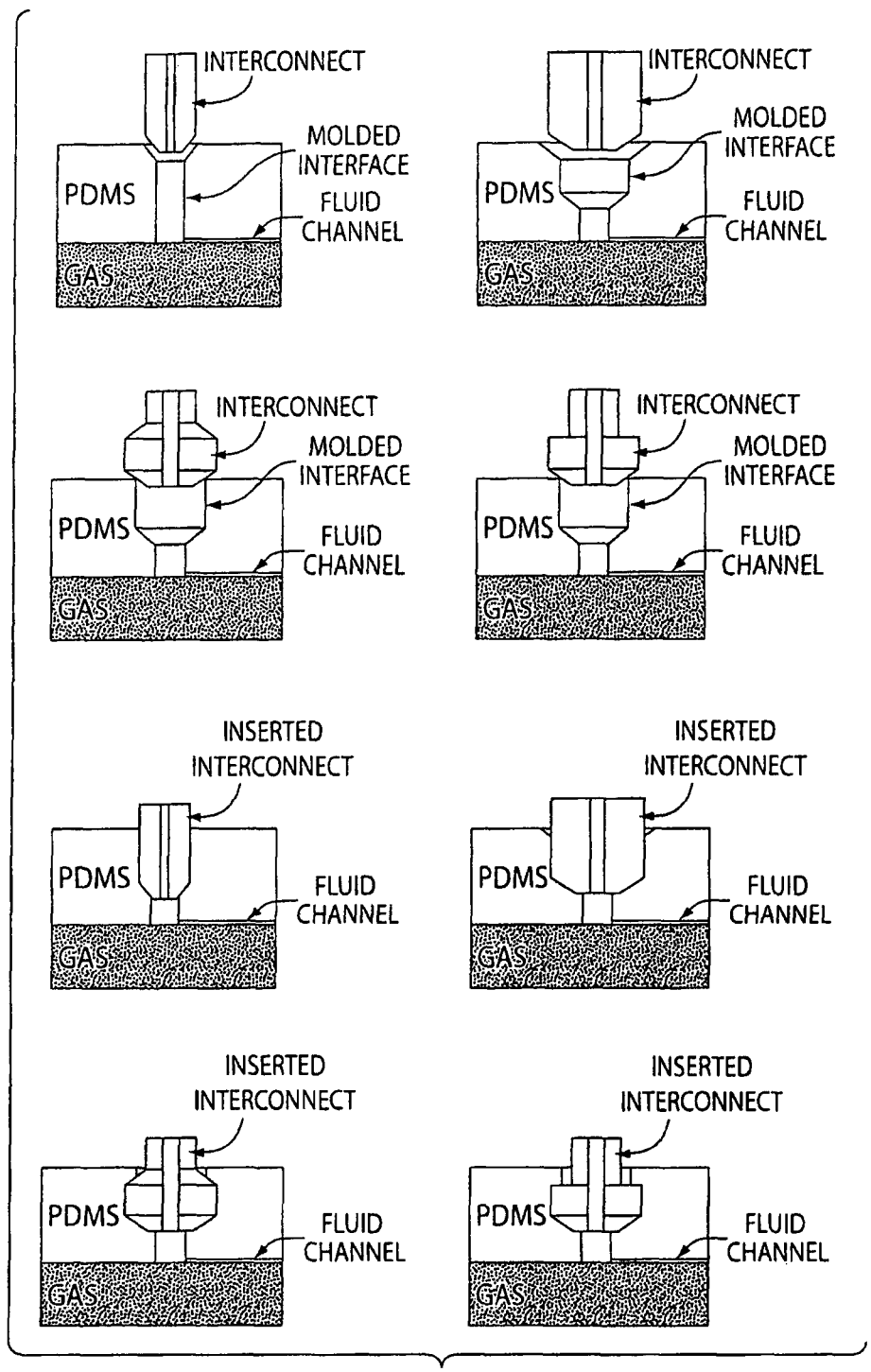
FIG. 11 illustrates possible interconnect designs for use with PDMS devices.

The present invention proposes the use of small interconnects based on creating a radial seal instead of a face seal between the microfluidic device and interconnect. The inserted interconnect would have a larger diameter than the mating feature on the device. When inserted, the stretching of the chip would provide the sealing force needed to make a leak-free seal between the external fluid lines and the microfluidic device. FIG. 11 details design possibilities for making this seal.

Studies were performed with the leftmost design of FIG. 1 using a cast hole in PDMS and 1/32" PEEK tubing, which showed that the seal was able to withstand more than 90 PSI of pressure without leakage.

Figure 12:
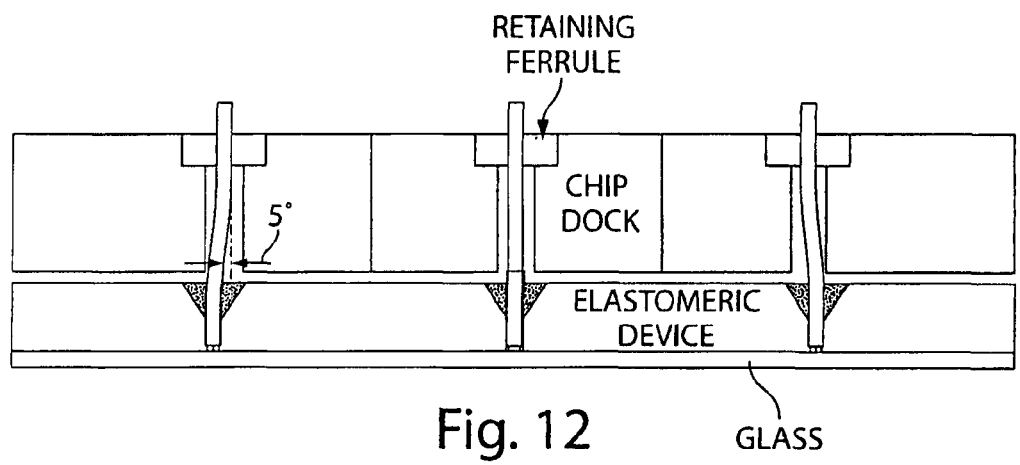
FIG. 12 illustrates self-alignment of fluidic interconnect

In order to handle instrument and chip manufacturing tolerances, the external interconnect must be self-aligning and the "capture radius" of the molded hole must be large enough to reliably steer the interconnect to the sealing surfaces. FIG. 12 shows that the entrance to the molded hole is large enough to guarantee capture but tapers down to the sealing surfaces. The external interconnect could be made directly out of the tubing leading up to the microfluidic substrate, thus eliminating potential leak points and unswept volumes. As seen in FIG. 12, the interconnect is surrounded by the substrate interconnects or "chip dock" for most of its length to make certain it is held within the tolerance stack-up of the system. The external interconnect is made from a hard but flexible material such as 1/32" PEEK tubing. The features in the microfluidic device can be molded directly into it during the manufacturing process, while the inserted seals can be molded/machined directly onto the tubing ends or molded as individual pieces and mechanically fastened to the tubing. The retaining ferrule shown in FIG. 12 would be attached during manufacturing and provide good absolute referencing of the tube length. The ferrule could be an off-the-shelf component or a custom manufactured part and be made from, for example, a polymer, an elastomer, or a metal. The tubing end could be tapered on the end (top most diagram) or squared off (the figure above). The specific shape of the end will be controlled by how easily the microfluidic device will gall during insertion.

Figure 13:
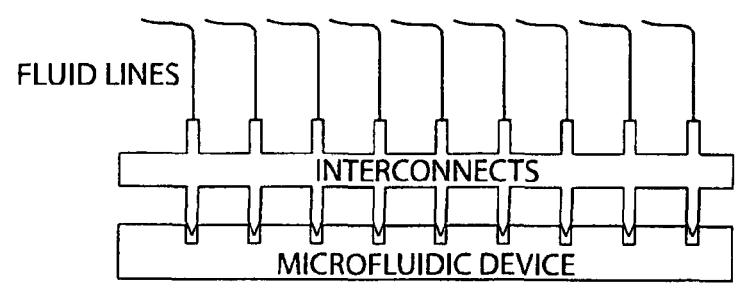
FIG. 13 illustrates the interconnects needed for each tube molded into a single monolithic self-aligned part.

Alternatively, it is also possible to mold all the interconnects needed for each tube into a single monolithic self-aligned part as detailed in FIG. 13. This may help reduce the difficulty in maintaining alignment of many external fluidic lines to the chip.

Methods for Molding Fluidic Interconnects Directly on the Substrate

The present invention also provides methods of direct molding of fluidic interconnects into a microfluidic device. Development of a commercial microfluidic platform requires a simple, reliable fluidic interconnect in order to reduce the chance of operator error and leaks. Molding these interconnects directly into the microfluidic device requires precise alignment of the molding pins to the patterned shim (the "master" manufactured from Silicon/photoresist or made from some metal) used to form the microfluidic and electrical channels. The extreme tolerances required when molding with a low viscosity elastomer such as PDMS requires near perfect sealing of the pin face to the master, while still accommodating imperfections in the master and assembly of the molding tool. In an embodiment, the present invention provides a precise and repeatable method of molding of interconnects while accommodating the imperfections in the molding process by introducing movable pins captured in an elastomeric sleeve molded directly into the tool. In order to effectively produce at relatively low volume and be able to inexpensively prototype devices, the tool must be able to use masters generated using standard photolithographic processes (e.g. silicon wafers patterned with SU-8).

Figure 14:
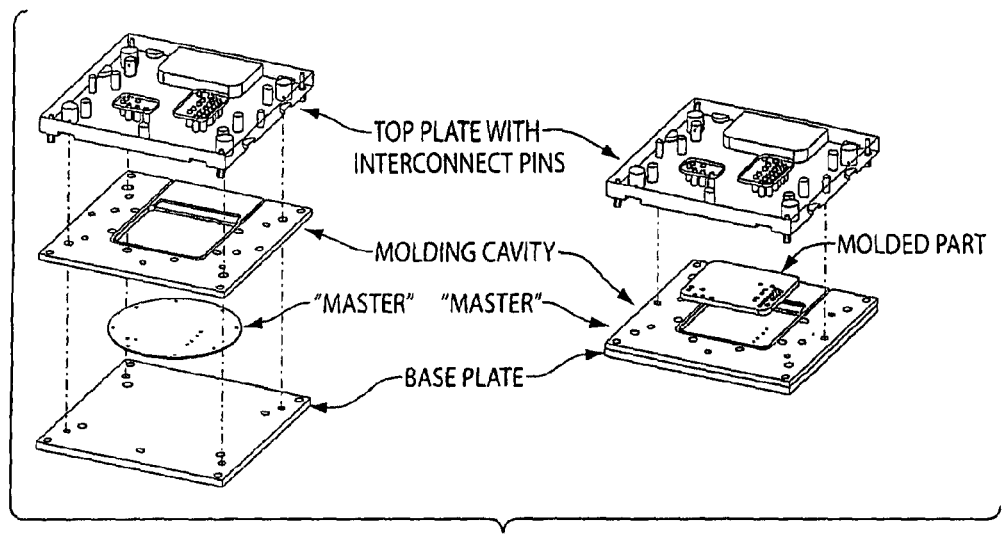
FIG. 14 shows a schematic of a molding tool based on this concept. The pins (orange) are captured within an elestomeric molded sleeve and a compression plate made from a rigid backer plate and foam rubber is used to apply gentle even pressure to the pins and generate the force needed to make the pins uniformly contact the master.

FIG. 14 shows a schematic of a molding tool based on this concept. In FIG. 14, the pins (orange) are captured within an elestomeric molded sleeve. A compression plate made from a rigid backer plate and foam rubber is used to apply gentle even pressure to the pins and generate the force needed to make the pins uniformly contact the master. The molded sleeve was found to be necessary to consistently prevent the uncured elastomer from penetrating the region between the pin and the top plate. Early designs used pins captured in tight clearance holes, and the pins would frequently bind in place (even with lubricant), preventing smooth motion of the pins and improper contact with the master. This would in turn cause a thin film of the elastomer to form between the bottom of the pin and the master ("Flash"). This flash prevents proper operation of the interconnects during chip operation. The addition of the elastomeric sleeves around each pin eliminated this problem, and produce consistent, reliable shutoff between the master and the pins.

Acoustic Actuator

The well or reservoir of the inlet module further include an acoustic actuator. To obtain one droplet comprising a single element of a specific biological/chemical material (e.g., a cell), separation of biological/chemical material, and uniformity of the number density of biological/chemical materials in a microfluidic channel is desirable. Accordingly, the microfluidic device can include an acoustic actuator. The loaded sample (biological/chemical material) can be well mixed and separated in a small chamber by acoustic wave before sending out to the nozzle region for encapsulation. The frequency of the acoustic wave should be fine-tuned so as not to cause any damage to the cells. The biological effects of acoustic mixing have been well studied (e.g., in the ink-jet industry) and many published literatures also showed that piezoelectric microfluidic device can deliver intact biological payloads such as live microorganisms and DNA.

The design of the acoustic resonant can use a Piezoelectric bimorph flat plate located on the side of the carved resonant in the PDMS slab. The resonant inlet can connect to the cell flow input channel and the outlet can connect to the cell flow pinching channel. The piezoelectric driving waveform can be carefully optimized to select the critical frequencies that can separate cells in fluids. There are five parameters to optimize beyond the frequency parameter and Lab electronics can be used to optimize the piezoelectric driving waveform. Afterwards, a low cost circuit can be designed to generate only the optimized waveform in a preferred microfluidic device.

Coalescence Module

The microfluidic device of the present invention also includes one or more coalescence modules. A "coalescence module" is within or coincident with at least a portion of the main channel at or downstream of the inlet module where molecules, cells, small molecules or particles comprised within droplets are brought within proximity of other droplets comprising molecules, cells, small molecules or particles and where the droplets in proximity fuse, coalesce or combine their contents. The coalescence module can also include an apparatus, for generating an electric force.

The electric force exerted on the fluidic droplet may be large enough to cause the droplet to move within the liquid. In some cases, the electric force exerted on the fluidic droplet may be used to direct a desired motion of the droplet within the liquid, for example, to or within a channel or a microfluidic channel (e.g., as further described herein), etc.

The electric field can be generated from an electric field generator, i.e., a device or system able to create an electric field that can be applied to the fluid. The electric field generator may produce an AC field (i.e., one that varies periodically with respect to time, for example, sinusoidally, sawtooth, square, etc.), a DC field (i.e., one that is constant with respect to time), a pulsed field, etc. The electric field generator may be constructed and arranged to create an electric field within a fluid contained within a channel or a microfluidic channel. The electric field generator may be integral to or separate from the fluidic system containing the channel or microfluidic channel, according to some embodiments. As used herein, "integral" means that portions of the components integral to each other are joined in such a way that the components cannot be in manually separated from each other without cutting or breaking at least one of the components.

Techniques for producing a suitable electric field (which may be AC, DC, etc.) are known to those of ordinary skill in the art. For example, in one embodiment, an electric field is produced by applying voltage across a pair of electrodes, which may be positioned on or embedded within the fluidic system (for example, within a substrate defining the channel or microfluidic channel), and/or positioned proximate the fluid such that at least a portion of the electric field interacts with the fluid. The electrodes can be fashioned from any suitable electrode material or materials known to those of ordinary skill in the art, including, but not limited to, silver, gold, copper, carbon, platinum, copper, tungsten, tin, cadmium, nickel, indium tin oxide ("ITO"), etc., as well as combinations thereof.

Electrodes

The device can include channels for use in fluid control and other channels filled with a metal alloy for casting integrated metal alloy components (i.e., electrodes). Alternatively, the electrodes can be manufactured using other technologies (e.g., lithographically patterned electrodes made from indium tin oxide or a metal such as platinum). The microfluidic device can include metal alloy components useful for performing electrical functions on fluids, including but not limited to, coalescing droplets, charging droplets, sorting droplets, detecting droplets and shaking droplets to mix the contents of coalesced droplets. The device can contain more than one of the above mentioned components for more than one of the above mentioned functions.

The electrodes comprising metal alloy components may either terminate at fluid channels or be isolated from fluid channels. The electrodes can be constructed by filling the appropriate channels with metal alloy. One way this can be accomplished is to use positive pressure injection of the metal alloy in a melted state, such as with a syringe, into the channels, and then cool the metal alloy to a solid form. Another example is to use negative pressure to draw the metal alloy in a melted state into the channels, and then cool the metal alloy to a solid form. This can be accomplished for example by use of capillary forces. Another method of construction can use any of the above mentioned embodiments, and then flush out the metal alloy in a melted state with another liquid to define the geometry of the metal alloy components. Another example is to use any of the above mentioned embodiments, and then use a localized cold probe to define a solid termination point for the metal alloy, and then cool the remaining metal alloy to a solid form. A further example is to use another material, such as microscopic solder spheres or UV curable conductive ink, to form a barrier between fluid and metal alloy channels, to define the geometry of the metal alloy components.

The device can include a combination of both integrated metal alloy components and a patterned electrically conductive layer. The patterned electrically conductive layer can have features patterned such that their boundaries are within a leak-proof seal. The device can have a patterned electrically conductive feature as one of two charging electrodes and one integrated metal alloy component as the other of two charging electrodes.

The device can include a plurality of electrodes that are insulated from the fluid present in the device, and the method of operation including appropriate application of dielectrical signals and appropriate fluids. In known devices, the electrodes are typically in contact with the fluids in order to allow discharge of species that would otherwise screen the applied dielectric field. Whereas, in devices where the electrodes have been insulated from the fluid, this screening effect typically arises so quickly that the device is not useful for any significantly extended period of time. The drawbacks of electrodes in contact with the fluids vs. insulated electrodes are (a) degraded reliability against leaking (since the interface between the electrodes and the other components of the device may be more difficult to effect a leak-proof seal), and (b) degraded reliability against electrode corrosion (whose failure mode effects include failure of application of dielectric fields, and fluid channel contamination).

The device of the present invention comprising a plurality of electrodes that are insulated from the fluid present in the device counteracts this screening effect by extending the screening rise time and including a polarity switch for all of the different dielectric fields applied in the device. The screening rise time is extended by using fluids with dielectrical properties. A polarity switch for all of the different dielectric fields applied in the device is achieved by using an algorithm for dielectrical control, which switches the polarity of the dielectrical fields at a frequency sufficiently high to maintain proper dielectrical function of the device. This dielectrical control algorithm may also switch the polarity for the dielectric fields in a cascading, time controlled manner starting at the fluid origin point and progressing downstream, so that given fluid components experience one polarity at every point along their course. The device of the present invention can be used with metal alloy electrodes or using a combination of metal alloy electrodes and patterned conductive film electrodes.

The invention can provide a microfluidic device using injected electrodes. The interface between the microscopic electrode (typically 25 μm thick) and the macroscopic interconnect can easily fail if the joint between the two is flexed. The flexing of the joint can be eliminated by securing a firm material that serves to fasten, support, and re-enforce the joint (i.e., a grommet) into the interface. In order to prevent flexing, the mating surface of the device can be manufactured from a hard material such as glass or plastic. The electrical connection with the external system can be made by securing the device such that it connects to a spring loaded contact, which is either offset from the grommet (thereby minimizing the force applied to the solder region), or centered on the grommet (as long as the contact does not touch the solder).

The metal alloy components are also useful for performing optical functions on fluids, including but not limited to, optical detection of droplets in a geometry which may include a mirror.

To prevent leakage of fluid out of electrodes placed within microfluidic channels, the microfluidic device can include a layer patterned with channels for fluid control, and another layer with patterned electrically conductive features, where the features are patterned such that their boundaries are within a leak-proof seal. The leak-proof seal can be achieved at the interface between the unpatterned areas of the fluid control layer and the unpatterned areas of the electrically conductive layer. The leak-proof seal can also be achieved by a third interfacial layer between the fluid control layer and the unpatterned areas of the electrically conductive layer. The third interfacial layer can or cannot be perforated at specific locations to allow contact between the fluid and the electrically conductive layer. Electrical access ports can also be patterned in the fluid control layer.

The electrodes and patterned electrically conductive layers as described can be associated with any module of the device (inlet module, coalescence module, mixing module, delay module, detection module and sorting module) to generate dielectric or electric forces to manipulate and control the droplets and their contents.

Effective control of uncharged droplets within microfluidic devices can require the generation of extremely strong dielectric field gradients. The fringe fields from the edges of a parallel plate capacitor can provide an excellent topology to form these gradients. The microfluidic device according to the present invention can include placing a fluidic channel between two parallel electrodes, which can result in a steep electric field gradient at the entrance to the electrodes due to edge effects at the ends of the electrode pair. Placing these pairs of electrodes at a symmetric channel split can allow precise bi-directional control of droplet within a device. Using the same principle, only with asymmetric splits, can allow single ended control of the droplet direction in the same manner. Alternatively, a variation on this geometry will allow precise control of the droplet phase by shifting.

In some cases, transparent or substantially transparent electrodes can be used. The electric field generator can be constructed and arranged (e.g., positioned) to create an electric field applicable to the fluid of at least about 0.01 V/micrometer, and, in some cases, at least about 0.03 V/micrometer, at least about 0.05 V/micrometer, at least about 0.08 V/micrometer, at least about 0.1 V/micrometer, at least about 0.3 V/micrometer, at least about 0.5 V/micrometer, at least about 0.7 V/micrometer, at least about 1 V/micrometer, at least about 1.2 V/micrometer, at least about 1.4 V/micrometer, at least about 1.6 V/micrometer, or at least about 2 V/micrometer. In some embodiments, even higher electric field intensities may be used, for example, at least about 2 V/micrometer, at least about 3 V/micrometer, at least about 5 V/micrometer, at least about 7 V/micrometer, or at least about 10 V/micrometer or more.

As described, an electric field may be applied to fluidic droplets to cause the droplets to experience an electric force. The electric force exerted on the fluidic droplets may be, in some cases, at least about 10-16 N/micrometer$^3$. In certain cases, the electric force exerted on the fluidic droplets may be greater, e.g., at least about 10-15 N/micrometer$^3$, at least about 1014 N/micrometer$^3$, at least about 10-13 N/micrometer, at least about 10-12 N/micrometer$^3$, at least about 10-11 N/micrometer$^3$, at least about 10-10 N/micrometer3, at least about 10-9 N/micrometer, at least about 108 N/micrometer$^3$, or at least about 10-7 N/micrometer3 or more. The electric force exerted on the fluidic droplets, relative to the surface area of the fluid, may be at least about 10-15 N/micrometer$^2$, and in some cases, at least about 10-14 N/micrometer$^2$, at least about 10-13 N/micrometer$^2$, at least about 10-12 N/micrometer$^2$, at least about 10-11 N/micrometer, at least about 10-10 N/micrometer$^2$, at least about 10-9 N/micrometer$^2$, at least about 10-8 N/micrometer, at least about 10-7 N/micrometer$^2$, or at least about 10-6 N/micrometer$^2$ or more. In yet other embodiments, the electric force exerted on the fluidic droplets may be at least about 10-9 N, at least about 10-8 N, at least about 10-7 N, at least about 10-6 N, at least about 10-5 N, or at least about 10-4 N or more in some cases.

Channel Expansion Geometries

In preferred embodiments described herein, droplet coalescence is presently carried out by having two droplet forming nozzles emitting droplets into the same main channel. The size of the nozzles allow for one nozzle to form a large drop that fills the exhaust line while the other nozzle forms a drop that is smaller than the first. The smaller droplet is formed at a rate that is less than the larger droplet rate, which insures that at most one small droplet is between big droplets. Normally, the small droplet will catch up to the larger one over a relatively short distance, but sometimes the recirculation zone behind the large drop causes the small drop to separate from the large drop cyclically. In addition, the small drop occasionally does not catch up with the large one over the distance between the nozzles and the coalescing electrodes. Thus, in some situations is a need for a more robust coalescence scheme.

Figure 15:
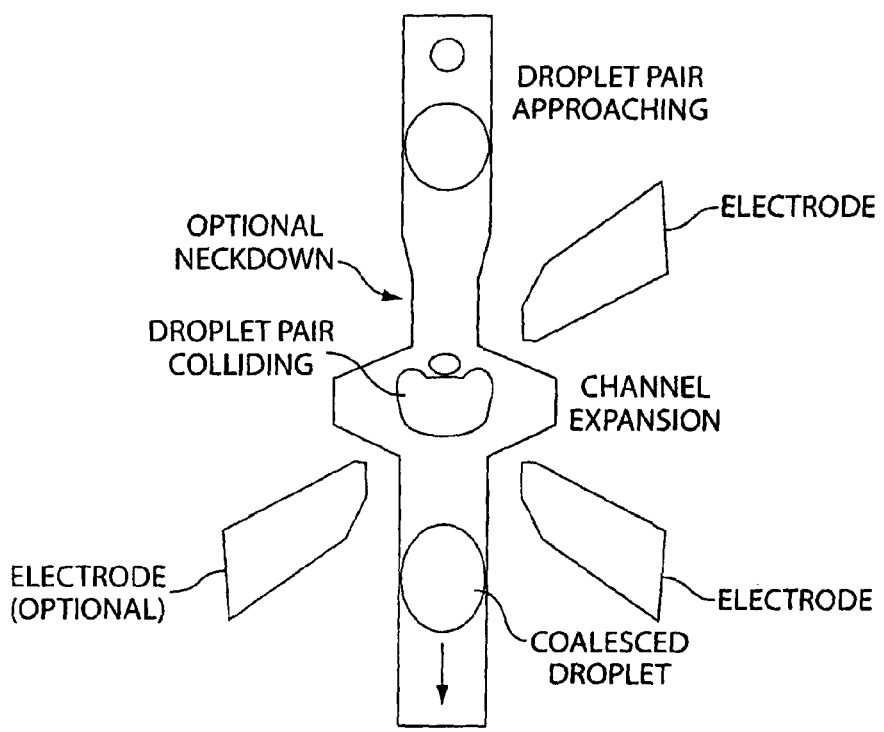
FIG. 15 is a schematic diagram of an improved coalescence module that shows an optional small constriction (neckdown) just before this expansion can be used to better align the droplets on their way into the coalescence point.

Geometric alterations in the coalescence module can create a more robust, reliable coalescence or fusing of droplets over a wider range of sizes and flows. The solution to improve the performance is to place an expansion in the main channel between the electrodes. FIG. 15 is a schematic diagram of the improved coalescence module. Optionally, a small constriction (neckdown) just before this expansion can be used to better align the droplets on their way into the coalescence point (also shown in the FIG. 15). This optional neckdown can help center the small droplet in the channel stream lines, reducing the chance that it will flow around the larger droplet prior to coalescing in the expansion. The electrode pair may be placed on either one side of the channel or on both sides.

The expansion in the coalescing region allows for a dramatic catching up of the small drop to the large drop, as shown through micrographs taken on an operating device. The volume of the expansion is big enough to slow the large droplet down so that the small drop always catches up to the large drop, but doesn't allow the next large drop to catch up and make contact with the pair to be coalesced. The electrodes allow for coalescence to take place when the drops are in contact with each other and passing through the field gradient.

Detection Module

The microfluidic device of the present invention can also include one or more detection modules. A "detection module" is a location within the device, typically within the main channel where molecules, cells, small molecules or particles are to be detected, identified, measured or interrogated on the basis of at least one predetermined characteristic. The molecules, cells, small molecules or particles can be examined one at a time, and the characteristic is detected or measured optically, for example, by testing for the presence or amount of a reporter. For example, the detection module is in communication with one or more detection apparatuses. The detection apparatuses can be optical or electrical detectors or combinations thereof. Examples of suitable detection apparatuses include optical waveguides, microscopes, diodes, light stimulating devices, (e.g., lasers), photo multiplier tubes, and processors (e.g., computers and software), and combinations thereof, which cooperate to detect a signal representative of a characteristic, marker, or reporter, and to determine and direct the measurement or the sorting action at the sorting module. However, other detection techniques can also be employed The term "determining," as used herein, generally refers to the analysis or measurement of a species, for example, quantitatively or qualitatively, and/or the detection of the presence or absence of the species. "Determining" may also refer to the analysis or measurement of an interaction between two or more species, for example, quantitatively or qualitatively, or by detecting the presence or absence of the interaction. Examples of suitable techniques include, but are not limited to, spectroscopy such as infrared, absorption, fluorescence, UV/visible, FTIR ("Fourier Transform Infrared Spectroscopy"), or Raman; gravimetric techniques; ellipsometry; piezoelectric measurements; immunoassays; electrochemical measurements; optical measurements such as optical density measurements; circular dichroism; light scattering measurements such as quasielectric light scattering; polarimetry; refractometry; or turbidity measurements as described further herein.

A detection module is within, communicating or coincident with a portion of the main channel at or downstream of the inlet module and, in sorting embodiments, at, proximate to, or upstream of, the sorting module or branch point. The sorting module may be located immediately downstream of the detection module or it may be separated by a suitable distance consistent with the size of the molecules, the channel dimensions and the detection system. Precise boundaries for the detection module are not required, but are preferred.

Detection modules used for detecting molecules and cells have a cross-sectional area large enough to allow a desired molecule, cells, bead, or particles to pass through without being substantially slowed down relative to the flow carrying it. The dimensions of the detection module are influenced by the nature of the sample under study and, in particular, by the size of the droplets, beads, particles, molecules or cells (including virions) under study. For example, mammalian cells can have a diameter of about 1 to 50 microns, more typically 10 to 30 microns, although some mammalian cells (e.g., fat cells) can be larger than 120 microns. Plant cells are generally 10 to 100 microns. However, other molecules or particles can be smaller with a diameter from about 20 nm to about 500 mn.

Waveguides

The present invention provides self-aligning optical waveguides and optical elements (lenses, prisms, mirrors, interconnects, etc.) for detection and control of droplets. Such waveguides can be used to provide well defined optical access to the fluidic channels to permit optical scattering, absorption, fluorescence, or any other optical measurement technique. In order to create the waveguides, a separate series of channels and useful shapes (lenses, mirrors, etc) can be created either simultaneously within the other channels in the substrate (i.e. in the same processing step) or in successive steps. The reusable master created in this way can then used to form the waveguide components and fluid channels without the need for special fixturing or careful alignment in subsequent steps. The extra channels or shapes can then filled with a high index of refraction liquid (for waveguides) or reflective material (for mirrors) through injection into the channel or void. The liquid can either remain as a fluid or be allowed to solidify. UV cure epoxies used by the telecommunications industry are excellent choices for the waveguide materials. Possible waveguide geometry can include a focusing lens and a back-reflecting mirror.

Sensors

One or more detections sensors and/or processors may be positioned to be in sensing communication with the fluidic droplet. "Sensing communication," as used herein, means that the sensor may be positioned anywhere such that the fluidic droplet within the fluidic system (e.g., within a channel), and/or a portion of the fluidic system containing the fluidic droplet may be sensed and/or determined in some fashion. For example, the sensor may be in sensing communication with the fluidic droplet and/or the portion of the fluidic system containing the fluidic droplet fluidly, optically or visually, thermally, pneumatically, electronically, or the like. The sensor can be positioned proximate the fluidic system, for example, embedded within or integrally connected to a wall of a channel, or positioned separately from the fluidic system but with physical, electrical, and/or optical communication with the fluidic system so as to be able to sense and/or determine the fluidic droplet and/or a portion of the fluidic system containing the fluidic droplet (e.g., a channel or a microchannel, a liquid containing the fluidic droplet, etc.). For example, a sensor may be free of any physical connection with a channel containing a droplet, but may be positioned so as to detect electromagnetic radiation arising from the droplet or the fluidic system, such as infrared, ultraviolet, or visible light. The electromagnetic radiation may be produced by the droplet, and/or may arise from other portions of the fluidic system (or externally of the fluidic system) and interact with the fluidic droplet and/or the portion of the fluidic system containing the fluidic droplet in such as a manner as to indicate one or more characteristics of the fluidic droplet, for example, through absorption, reflection, diffraction, refraction, fluorescence, phosphorescence, changes in polarity, phase changes, changes with respect to time, etc. As an example, a laser may be directed towards the fluidic droplet and/or the liquid surrounding the fluidic droplet, and the fluorescence of the fluidic droplet and/or the surrounding liquid may be determined. "Sensing communication," as used herein may also be direct or indirect. As an example, light from the fluidic droplet may be directed to a sensor, or directed first through a fiber optic system, a waveguide, etc., before being directed to a sensor.

Non-limiting examples of detection sensors useful in the invention include optical or electromagnetically-based systems. For example, the sensor may be a fluorescence sensor (e.g., stimulated by a laser), a microscopy system (which may include a camera or other recording device), or the like. As another example, the sensor may be an electronic sensor, e.g., a sensor able to determine an electric field or other electrical characteristic. For example, the sensor may detect capacitance, inductance, etc., of a fluidic droplet and/or the portion of the fluidic system containing the fluidic droplet. In some cases, the sensor may be connected to a processor, which in turn, cause an operation to be performed on the fluidic droplet, for example, by sorting the droplet.

Characteristics

Characteristics determinable with respect to the droplet and usable in the invention can be identified by those of ordinary skill in the art. Non-limiting examples of such characteristics include fluorescence, spectroscopy (e.g., optical, infrared, ultraviolet, etc.), radioactivity, mass, volume, density, temperature, viscosity, pH, concentration of a substance, such as a biological substance (e.g., a protein, a nucleic acid, etc.), or the like.

A corresponding signal is then produced, for example indicating that "yes" the characteristic is present, or "no" it is not. The signal may correspond to a characteristic qualitatively or quantitatively. That is, the amount of the signal can be measured and can correspond to the degree to which a characteristic is present. For example, the strength of the signal may indicate the size of a molecule, or the potency or amount of an enzyme expressed by a cell, or a positive or negative reaction such as binding or hybridization of one molecule to another, or a chemical reaction of a substrate catalyzed by an enzyme. In response to the signal, data can be collected and/or a control system in the sorting module, if present, can be activated to divert a droplet into one branch channel or another for delivery to the collection module or waste module. Thus, in sorting embodiments, molecules or cells within a droplet at a sorting module can be sorted into an appropriate branch channel according to a signal produced by the corresponding examination at a detection module. The means of changing the flow path can be accomplished through mechanical, electrical, optical, or some other technique as described herein.

A preferred detector is an optical detector, such as a microscope, which may be coupled with a computer and/or other image processing or enhancement devices to process images or information produced by the microscope using known techniques. For example, molecules can be analyzed and/or sorted by size or molecular weight. Enzymes can be analyzed and/or sorted by the extent to which they catalyze chemical reaction of a substrate (conversely, substrate can be analyzed and/or sorted by the level of chemical reactivity catalyzed by an enzyme). Cells can be sorted according to whether they contain or produce a particular protein, by using an optical detector to examine each cell for an optical indication of the presence or amount of that protein. The protein may itself be detectable, for example by a characteristic fluorescence, or it may be labeled or associated with a reporter that produces a detectable signal when the desired protein is present, or is present in at least a threshold amount. There is no limit to the kind or number of characteristics that can be identified or measured using the techniques of the invention, which include without limitation surface characteristics of the cell and intracellular characteristics, provided only that the characteristic or characteristics of interest for sorting can be sufficiently identified and detected or measured to distinguish cells having the desired characteristic(s) from those which do not. For example, any label or reporter as described herein can be used as the basis for analyzing and/or sorting molecules or cells, i.e. detecting molecules or cells to be collected.

Fluorescence Polarization

As described herein, the biological/chemical entity to be analyzed may itself be detectable, for example by a characteristic fluorescence, or it may be labeled or associated with a reporter that produces a detectable signal when the desired protein is present, or is present in at least a threshold amount. Luminescent colloidal semiconductor nanocrystals called quantum dots or q-dots (QD) are inorganic fluorophores that have the potential to circumvent some of the functional limitations encountered by organic dyes. In particular, CdSe—ZnS core-shell QDs exhibit size-dependent tunable photoluminescence (PL) with narrow emission bandwidths (FWHM ~30 to 45 nm) that span the visible spectrum and broad absorption bands. These allow simultaneous excitation of several particle sizes (colors) at a common wavelength. This, in turn, allows simultaneous resolution of several colors using standard instrumentation. CdSe—ZnS QDs also have high quantum yields, are resistant to photodegradation, and can be detected optically at concentrations comparable to organic dyes.

Quantum dots are nano-scale semiconductors typically consisting of materials such as crystalline cadmium selenide. The term 'q-dot' emphasizes the quantum confinement effect of these materials, and typically refers to fluorescent nanocrystals in the quantum confined size range. Quantum confinement refers to the light emission from bulk (macroscopic) semiconductors such as LEDs which results from exciting the semiconductor either electrically or by shining light on it, creating electron-hole pairs which, when they recombine, emit light. The energy, and therefore the wavelength, of the emitted light is governed by the composition of the semiconductor material. If, however, the physical size of the semiconductor is considerably reduced to be much smaller than the natural radius of the electron-hole pair (Bohr radius), additional energy is required to "confine" this excitation within the nanoscopic semiconductor structure leading to a shift in the emission to shorter wavelengths. Three different q-dots in several concentrations each can be placed in a microdroplet, and can then be used with a microfluidic device to decode what is in the drop. The Q-dot readout extension to the fluorescence station can be incorporated into the design of the microfluidic device. A series of dichroic beamsplitters, emission filters, and detectors can be stacked onto the system, allowing measurement of the required five emission channels (two fluorescence polarization signals and three q-dot bands).

Fluorescence Polarization (FP) detection technology enables homogeneous assays suitable for high throughput screening assays in the Drug Discovery field. The most common label in the assays is fluorescein. In FP-assay the fluorophore is excited with polarized light. Only fluorophores parallel to the light absorb and are excited. The excited state has a lifetime before the light emission occurs. During this time the labeled fluorophore molecule rotates and the polarization of the light emitted differs from the excitation plane. To evaluate the polarization two measurements are needed: the first using a polarized emission filter parallel to the excitation filter (S-plane) and the second with a polarized emission filter perpendicular to the excitation filter (P-plane). The Fluorescence Polarization response is given as mP (milli-Polarization level) and is obtained from the equation:

$$\text{Polarization}(mP)=1000*(S-G*P)/(S+G*P)$$

where S and P are background subtracted fluorescence count rates and G (grating) is an instrument and assay dependent factor.

The rotational speed of a molecule is dependent on the size of the molecule, temperature and viscosity of the solution. Fluorescein has a fluorescence lifetime suitable for the rotation speeds of molecules in bio-affinity assays like receptor-ligand binding assays or immunoassays of haptens. The basic principle is that the labeled compound is small and rotates rapidly (low polarization). When the labeled compound binds to the larger molecule, its rotation slows down considerably (polarization changes from low to high polarization). Thus, FP provides a direct readout of the extent of tracer binding to protein, nucleic acids, and other biopolymers.

Fluorescence polarization technology has been used in basic research and commercial diagnostic assays for many decades, but has begun to be widely used in drug discovery only in the past six years. Originally, FP assays for drug discovery were developed for single-tube analytical instruments, but the technology was rapidly converted to high-throughput screening assays when commercial plate readers with equivalent sensitivity became available. These assays include such well-known pharmaceutical targets such as kinases, phosphatases, proteases, G-protein coupled receptors, and nuclear receptors. Other homogeneous technologies based on fluorescence intensity have been developed.

These include energy transfer, quenching, and enhancement assays. FP offers several advantages over these. The assays are usually easier to construct, since the tracers do not have to respond to binding by intensity changes. In addition, only one tracer is required and crude receptor preparations may be utilized. Furthermore, since FP is independent of intensity, it is relatively immune to colored solutions and cloudy suspensions. FP offers several advantages in the area of instrumentation. Because FP is a fundamental property of the molecule, and the reagents are stable, little or no standardization is required. FP is relatively insensitive to drift in detector gain settings and laser power.

The dyes chosen for FP are commonly used in most cell- and enzyme-based assays and are designed not to overlap significantly with the q-dots. The dyes are evaluated both independently and together with the q-dots (at first off-instrument) to assess the cross-talk. Preferably, the liquid q-dot labels are read outside a spectral wavelength band currently used in FACS analysis and sorting (i.e., the dyes flourescein, Cy3, Cy5, etc). This permits the use of currently-available assays (dependent on these dyes). Using specific q-dots, crosstalk is minimized.

Accordingly, the present invention provides methods to label droplets and/or nanoreactors formed on a microfluidic device by using only a single dye code to avoid cross-talk with other dyes during FP. Additionally, the present invention provides methods to create FP dye codes to label compounds contained within liquids (including droplets and/or nanoreactors) where the compound is designed to be differentiated by FP on a microfluidic device. In this manner, dye codes having the same color, absorption, and emission could be used to label compounds within liquids.

In one aspect, the present invention is directed to the use of fluorescence polarization to label liquids. Droplets can be labeled using several means. These labeling means include, but are not limited to, the use of different dyes, quantum dots, capacitance, opacity, light scattering, fluorecence intensity (FI), fluorescence lifetime (FL), fluorescence polarization (FP), circular dichroism (CD), fluoreceneece correlation and combinations of all of these previous labeling means. The following disclosure describes the use of FP and FI as a means to label droplets on a microfluidic device. In addition, the use of FL as a means to adjust the overall FP of a solution, and by varying the concentration of the total FI, to create a 2-dimensional encoding scheme is demonstrated.

Figure 16:
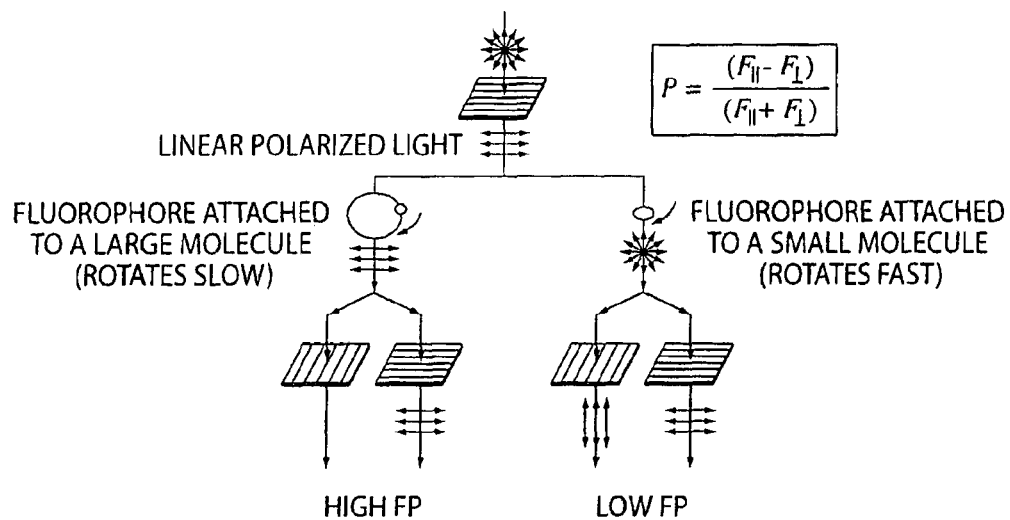
FIG. 16 illustrates that fluorescence polarization (FP) measures the tumbling rate of a compound in solution and is a function of it's volume (in most cases, volume is correlated with MW)

In general, molecules that take up more volume will tumble slower than a smaller molecule coupled to the same fluorophore (see FIG. 16). FP is independent of the concentration of the dye; liquids can have vastly different concentrations of FITC in them yet still have identical FP measurements.

Figure 17:
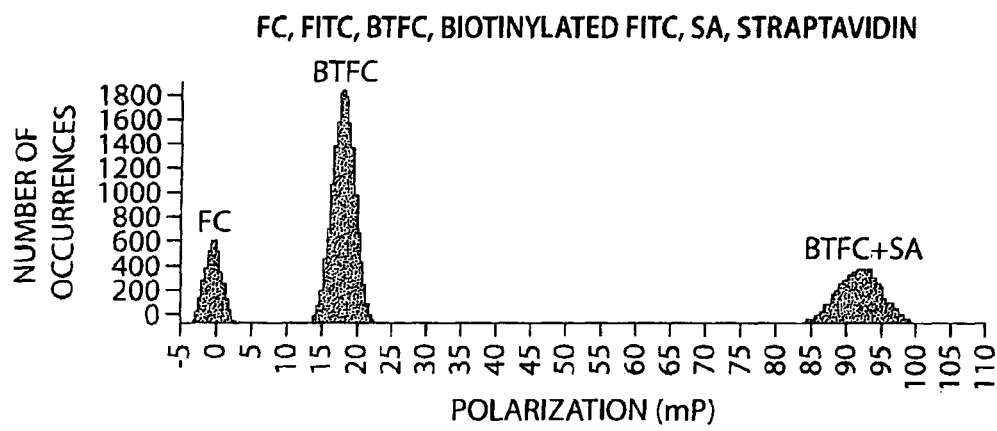
FIG. 17 shows the fluorescence polarization of three different compounds. Results of reading polarization in 18,000 drops containing 3 distinct species (FC, BTFC, and BTFC bound to SA). Ideal for reading results of drug screening assays, protein interactions, or DNA hybridization.

In a preferred embodiment, a FP dye is an organic dye that does not interfere with the assay dye is used. Furthermore, since the total intensity of the FP dye can be quantified, a second dimension in which to label the droplet is provided. Thus, one can exploit the differences in FP to create an encoding scheme of dye within a liquid solution, including droplets. An example is shown in FIG. 17 whereby the droplets are labeled with 3 differently-sized FITC molecules (i.e., three different droplets contain FITC molecules and FITC coupled to either biotin or streptavidin, respectively). Therefore, in a single dimension, FP can be used to create an encoding scheme. However, the present invention can also use Fluorescence Intensity (FI) of the overall solution to create even more labels in a second dimension. An example of labeling droplets in 2 dimensions is shown in FIGS. 18A-B.

Figure 18A:
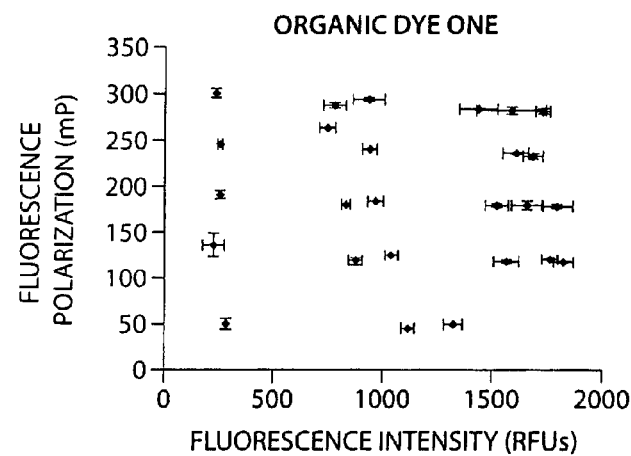
FIG. 18A illustrates encoding a liquid solution using both overall fluorescence polarization and overall dye intensity within droplets.
Figure 18B:
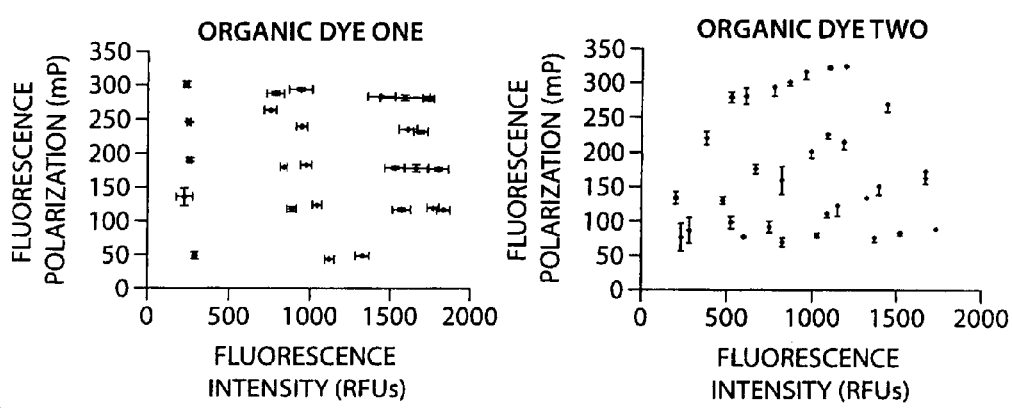
FIG. 18B shows that multiple colors of fluorescence polarization and FI increases the number of possible labels. Ten intensity levels with ten fluorescence polarization levels on two colors yields 10,000 labels
Figure 19:
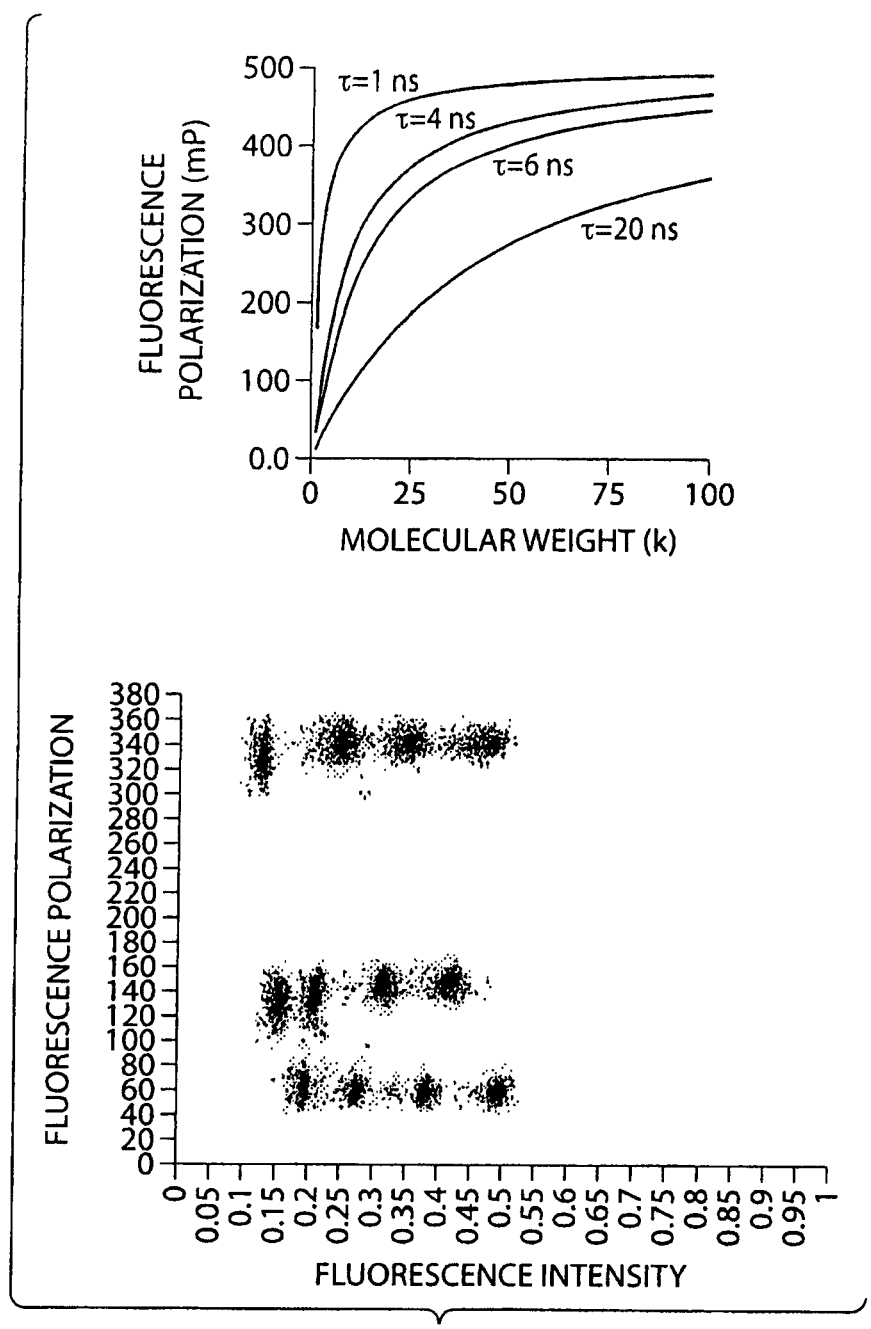
FIG. 19 illustrates FPcoding using dyes having different fluorescence lifetimes. These were made one element at a time, stored in a single syringe overnight and then loaded back on chip. The codes were made by using a ratio of two different dyes, one with a short lifetime and hence high FP and one with a long lifetime and correspondingly low FP. The mixtures have intermediate FP signals. The intensity is tuned by controlling the overall concentration of the two dyes.

Interestingly, the differences of the fluorescence lifetime (FL) of two dyes with spectral overlap in the detected emission wavelength to change the overall FP of the combined solution can also be exploited (see FIGS. 18A-B and 19).

Although FIG. 17 discusses the use of multiple compounds to which a dye molecule is attached to span a range of FP, it is also possible to span the range using a high and low molecular weight compound set. As exemplified by FIG. 19, a dye can be attached to a large compound (for example streptavidin) and kept at a fixed concentration, to which a smaller compound (for example, a free dye molecule) would be titrated into the same solution. The FP of the solution can be adjusted to be in discernable increments from the value of the large molecule to somewhere slightly greater than the FP of the smaller molecule. The [total] dye intensity can be varied by varying the concentration of the mixture of the two dye-attached compounds. By varying total dye concentration and the FP, two dimensions can be used to generate the FP dye codes (FPcodes). Accordingly, many FPcodes can be generated using only two compounds.

This could also include use of large fluorescent proteins such as GFP and the phycobiliproteins combined with a smaller molecule.

Examples of dyes commonly used in biological dyes are listed in the table below.

| Excitation Wavelength | Emission Wavelength | Examples of Compatible Dyes |
| --- | --- | --- |
| 450 | 500 | Cyan 500 |
| 483 | 533 | SYBR Green, FAM |
| 523 | 568 | HEX, VIC |
| 588 | 610 | RED 610 |
| 615 | 640 | RED 640 |
| 650 | 670 | CY5 |

In another aspect, the present invention is directed labeling solids using properties other than dye emission and dye concentration. In one embodiment the solid can include, for example, a bead or location on a solid support or chip. As demonstrated above for liquids, FI and FL can be two of many dimensions of characteristics used as labels. By way of non-limiting example, it is possible to use two dyes with different FL to change the overall FP for a solid such as a bead or other mobile solid support.

In another embodiment, a linker can be used to couple the dye to the bead. The linker can be varied so as to allow the dye to have differing degrees of freedom in which to rotate (i.e., tumble). Varying the linker in this manner can change the FP of the attached dye, which in unique combinations can be used as a label. In some embodiments, the beads can be swollen in organic solvent and the dyes held in place by hydrophobic forces. In this case, the FP, FI, FL methods described above for liquid labeling can also be used as a means for labeling the beads. A quenching molecule can also be used to change the characteristics of a dye. Such quenching can be continuous or brought about through the interaction of a molecule, such as a peptide or nucleic acid linker, with differing means of bringing molecules together depending on the strength of linker-internal interaction (e.g., a nucleotide stem loop structure of varying lengths).

The reactions analyzed on the virtual, random and non-random arrays (discussed briefly below) can be also increased beyond the two (cy3 and cy5 intensities) commonly used for multiplexing. For example, different FP, FI, etc can be used as a read-out.

Random array decoding: Beads of the prior art use one or more pre-attached oligonucleotide-coupled beads that are held in place in a fiber-optic faceplate (for example, those used by Illumina). The oligos on the beads are decoded using sequential hybridization of a labeled complementary oligo. The assay of the prior art uses a separate oligonucleotide complementary zipcode ('Illumacode') attached to each type of bead.

The invention described herein is superior to the methods of the prior art in that the FP, FI, FL-labeled bead or mobile solid support can be placed into a random array (e.g., a chip as manufactured by Illumina) and the FP, FI, FL used to decode the bead. The FP, FI, FL of the bead can be decoded before using the chip and the different beads 'mapped' as to their specific locations. Alternatively, the bead can be decoded during attachment of the assay read-out. Significantly, the methods described by the present invention can be used to pre-determine the location of each bead-type either before, or during analysis.

Virtual array decoding: Methods of the prior art use 2 lasers and 3 detectors to differentiate a set of 100 bead-types. The beads-types are differentiated by the FI of two different dyes present in 1 of 10 concentrations (per dye) contained within the bead, and the assay detector is used to measure fluorescein concentration on the bead. The dyes, which are added to organic-solvent swollen beads, are not directly attached to the beads, but remain held within the bead by hydrophobic forces.

Using the methods of the present invention as described herein, a second detector to the machines of the prior art used to measure FP can be added, thereby adding a third dimension and extending the encoding scheme beyond the 100 available in the prior art.

Non-random array decoding: In chips of the prior art (such as those used by Affymetrix) oligonucleotides are synthesized directly on the chip. Decoding is simply a matter of knowing the location of the assay on the chip.

The methods as described herein can be advantageously used in conjunction with such chips to increase the number of things that can be simultaneously analyzed (i.e., multiplexed) on the chip. By way of non-limiting example, Cy3, Cy5, FL and FP can be used as analysis markers for hybridization reactions.

The present invention also provides methods for labeling micro or nano-sized droplets using Radio Frequency Identification (RFID). RFID tags can improve the identification of the contents within the droplets. Preferably, the droplets are utilized within a microfluidic device.

RFID is an automatic identification method, relying on storing and remotely retrieving data using devices called RFID tags or transponders. An RFID tag is an object that can be attached to or incorporated into a product, animal, or person for the purpose of identification using radio waves. Chip-based RFID tags contain silicon chips and antennae. Passive tags require no internal power source, whereas active tags require a power source. Hitachi has "powder" 0.05 mm×0.05 mm RFID chips. The new chips are 64 times smaller than the previous record holder, the 0.4 mm×0.4 mm mu-chips, and nine times smaller than Hitachi's last year prototype, and have room for a 128-bit ROM that can store a unique 38-digit ID number.

In one embodiment, a solution containing RFID tags are emulsified into droplets and are used as a label for the identification of the material within the droplet solution. Applications include, but are not limited to; genetics, genomics, proteomics, chemical synthesis, biofuels, and others.

Lasers

To detect a reporter or determine whether a molecule, cell or particle has a desired characteristic, the detection module may include an apparatus for stimulating a reporter for that characteristic to emit measurable light energy, e.g., a light source such as a laser, laser diode, light emitting diode (LED), high-intensity lamp, (e.g., mercury lamp), and the like. Where a lamp is used, the channels are preferably shielded from light in all regions except the detection module. Where a laser is used, the laser can be set to scan across a set of detection modules from different analysis units. In addition, laser diodes or LED's may be microfabricated into the same chip that contains the analysis units. Alternatively, laser diodes or LED's may be incorporated into a second chip (i.e., a laser diode chip) that is placed adjacent to the analysis or microchip such that the laser light from the diodes shines on the detection module(s).

An integrated semiconductor laser and/or an integrated photodiode detector can be included on the substrate in the vicinity of the detection module. This design provides the advantages of compactness and a shorter optical path for exciting and/or emitted radiation, thus minimizing distortion and losses.

Fluorescence produced by a reporter is excited using a laser beam focused on molecules (e.g., DNA, protein, enzyme or substrate) or cells passing through a detection region. Fluorescent reporters can include, but are not limited to, rhodamine, fluorescein, Texas red, Cy 3, Cy 5, phycobiliprotein (e.g., phycoerythrin), green fluorescent protein (GFP), YOYO-1 and PicoGreen. In molecular fingerprinting applications, the reporter labels can be fluorescently labeled single nucleotides, such as fluorescein-dNTP, rhodamine-dNTP, Cy3-dNTP, etc.; where dNTP represents dATP, dTTT, dUTP or dCTP. The reporter can also be chemically-modified single nucleotides, such as biotin-dNTP. The reporter can be fluorescently or chemically labeled amino acids or antibodies (which bind to a particular antigen, or fragment thereof, when expressed or displayed by a cell or virus).

The device can analyze and/or sort cells based on the level of expression of selected cell markers, such as cell surface markers, which have a detectable reporter bound thereto, in a manner similar to that currently employed using fluorescence-activated cell sorting (FACS) machines. Proteins or other characteristics within a cell, and which do not necessarily appear on the cell surface, can also be identified and used as a basis for sorting. The device can also determine the size or molecular weight of molecules such as polynucleotides or polypeptides (including enzymes and other proteins) or fragments thereof passing through the detection module. Alternatively, the device can determine the presence or degree of some other characteristic indicated by a reporter. If desired, the cells, particles or molecules can be sorted based on this analysis. The sorted cells, particles or molecules can be collected from the outlet channels in collection modules (or discarded in wasted modules) and used as needed. The collected cells, particles or molecules can be removed from the device or reintroduced to the device for additional coalescence, analysis and sorting.

Processors

As used herein, a "processor" or a "microprocessor" is any component or device able to receive a signal from one or more sensors, store the signal, and/or direct one or more responses (e.g., as described above), for example, by using a mathematical formula or an electronic or computational circuit. The signal may be any suitable signal indicative of the environmental factor determined by the sensor, for example a pneumatic signal, an electronic signal, an optical signal, a mechanical signal, etc.

The device of the present invention can comprise features, such as integrated metal alloy components and/or features patterned in an electrically conductive layer, for detecting droplets by broadcasting a signal around a droplet and picking up an electrical signal in proximity to the droplet.

Parallel Analysis

The droplet content detection can also be achieved by simultaneous detection of contents of multiple droplets in parallel using spectroscopic fluorescence imaging with sensitivity as high as single-molecule limit. One can spatially distribute droplets containing fluorescent entities such as fluorophore biological markers and/or quantum dots in a two-dimensional sheet in a microscopic field-of-view. The filed-of-view of those droplets can then be illuminated by a fluorescence excitation source and the resulting fluorescence can be spectroscopically imaged. Therefore, for a given fluorescence detection sensitivity, the throughput of fluorescence detection compared to a single-drop fluorescence detection method can be increased by a factor of a/b for a given sensitivity, where a is the number of droplets that can be imaged within a given field-of-view, and b is the ratio of the fluorescence sensitivity of a single-drop fluorescence detector compared to that of the multiple drop fluorescence detector. Furthermore, unlike single-drop fluorescent detection method where the drops are flowed through a detection volume so that their residence time in the detection volume, and hence the signal integration time and sensitivity, is limited, the residence time of the droplet in the field-of-view can be unlimited, thereby allowing sensitivity as high as the single-molecule limit.

Beads

The device of the present invention also comprises the use of beads and methods for analyzing and sorting beads (i.e, bead reader device). The device can read and either sort or not sort droplets containing one or more of a set of two or more beads. Each bead can be differentiated from each other bead within a set. Beads can be separated by several tags including, but not limited to, quantum dyes, fluorescent dyes, ratios of fluorescent dyes, radioactivity, radio-tags, etc. For example, a set of beads containing a ratio of two dyes in discrete amounts with an apparatus for detecting and differentiating beads containing one discrete ratio from the other beads in this set having a different ratio of the two dyes. The microfluidic device can include paramagnetic beads. The paramagnetic beads can introduce and remove chemical components from droplets using droplet coalescence and breakup events. The paramagnetic beads can also be used for sorting droplets.

The present invention provides methods of screening molecular libraries on beads through limited-dilusion-loading and then chemical or optical release inside of droplets. Provided are methods for chemical synthesis on a bead and releasing said chemical attached to the bead using a releasing means (chemical, UV light, heat, etc) within a droplet, and then combining a second droplet to the first droplet for further manipulation. For example, tea-bag synthesis of chemicals on a bead simultaneously with a means for identifying said bead (using, for example, a mass spec tag). Using the resulting mixed-chemistry beads in a droplet within a fluid flow, and exposing the beads to UV light to release the chemical synthesized from the bead into the droplet environment. Combining the droplet containing the released chemical with a droplet containing a cell, and performing a cell-based assay. Sorting droplets having the desired characteristics (for example, turn on of a reporter gene), and then analyzing the sorted beads using mass spectroscopy.

The device of the present invention can comprise column separation prior to bead sorting. A device containing a channel loaded with a separating means for chromatographically sorting the sample prior to droplet formation. Such separating means could include size, charge, hydrophobicity, atomic mass, etc. The separating can be done isocratic or by use of a means for generating a gradient chemically, (for example using salt or hydrophobicity), electrically, by pressure, or etc. For example, a channel is preloaded with Sepharose size exclusion media. A sample is loaded at one end, and the droplets are formed at an opposing end. The sample separates by size prior to becoming incorporated within a droplet.

Sorting Module

The microfluidic device of the present invention can further include one or more sorting modules. A 37 sorting module" is a junction of a channel where the flow of molecules, cells, small molecules or particles can change direction to enter one or more other channels, e.g., a branch channel for delivery to an outlet module (i.e., collection or waste module), depending on a signal received in connection with an examination in the detection module. Typically, a sorting module is monitored and/or under the control of a detection module, and therefore a sorting module may "correspond" to such detection module. The sorting region is in communication with and is influenced by one or more sorting apparatuses. A sorting apparatus comprises techniques or control systems, e.g., dielectric, electric, electro-osmotic, (micro-) valve, etc. A control system can employ a variety of sorting techniques to change or direct the flow of molecules, cells, small molecules or particles into a predetermined branch channel. A "branch channel" is a channel which is in communication with a sorting region and a main channel. The main channel can communicate with two or more branch channels at the sorting module or "branch point", forming, for example, a T-shape or a Y-shape. Other shapes and channel geometries may be used as desired. Typically, a branch channel receives molecules, cells, small molecules or particles depending on the molecule, cells, small molecules or particles characteristic of interest as detected by the detection module and sorted at the sorting module. A branch channel can have an outlet module and/or terminate with a well or reservoir to allow collection or disposal (collection module or waste module, respectively) of the molecules, cells, small molecules or particles. Alternatively, a branch channel may be in communication with other channels to permit additional sorting.

The device of the present invention can further include one or more outlet modules. An "outlet module" is an area of the device that collects or dispenses molecules, cells, small molecules or particles after coalescence, detection and/or sorting. The outlet module can include a collection module and/or a waste module. The collection module can be connected to a means for storing a sample. The collection module can be a well or reservoir for collecting and containing droplets detected to have a specific predetermined characteristic in the detection module. The collection module can be temperature controlled. The waste module can be connected to a means for discarding a sample. The waste module can be a well or reservoir for collecting and containing droplets detected to not have a specific predetermined characteristic in the detection module. The outlet module is downstream from a sorting module, if present, or downstream from the detection module if a sorting module is not present. The outlet module may contain branch channels or outlet channels for connection to a collection module or waste module. A device can contain more than one outlet module.

Figure 20A:
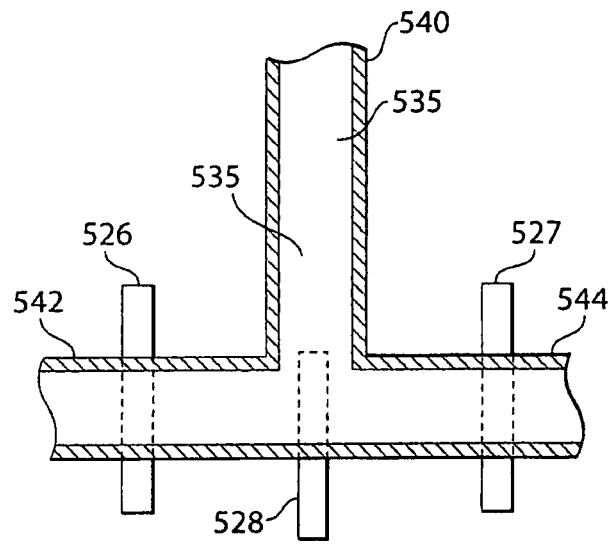
FIGS. 20A-D illustrate the sorting and/or splitting of droplets in accordance with another embodiment of the invention
Figure 20B:
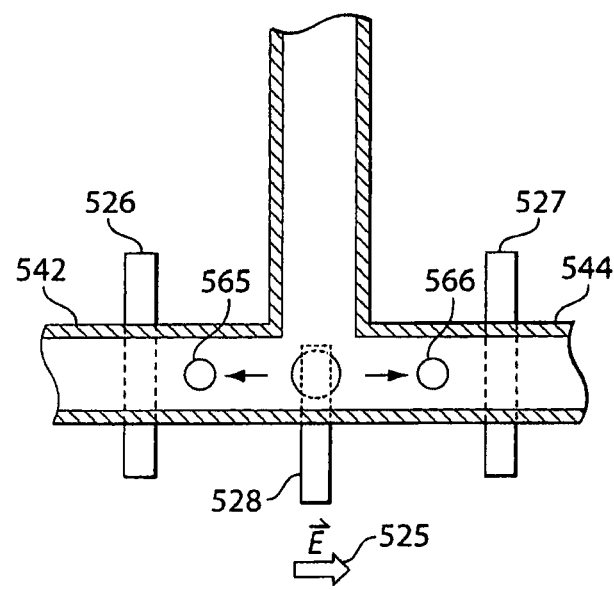
Figure 20C:
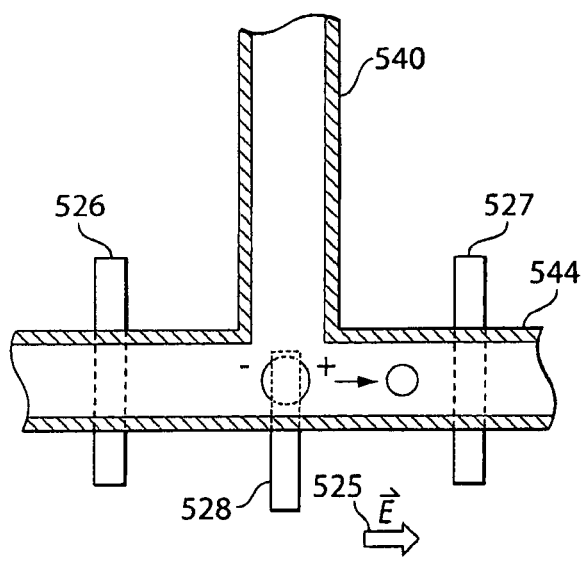
Figure 20D:
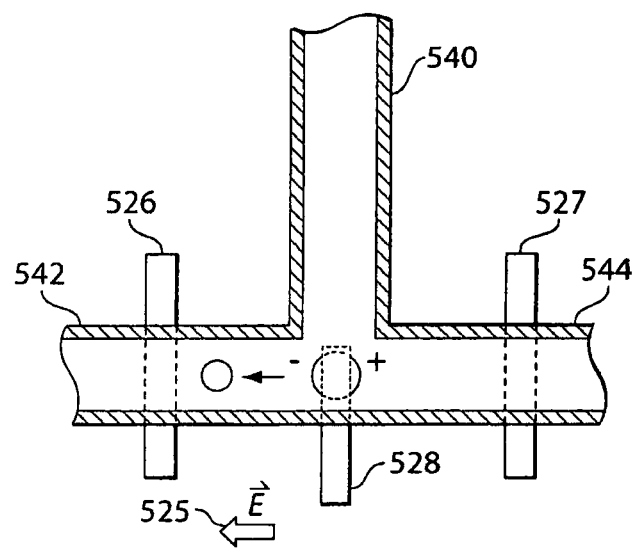

A characteristic of a fluidic droplet may be sensed and/or determined in some fashion, for example, as described herein (e.g., fluorescence of the fluidic droplet may be determined), and, in response, an electric field may be applied or removed from the fluidic droplet to direct the fluidic droplet to a particular region (e.g. a channel). A fluidic droplet is preferably sorted or steered by inducing a dipole in the uncharged fluidic droplet (which may be initially charged or uncharged), and sorting or steering the droplet using an applied electric field. The electric field may be an AC field, a DC field, etc. For example, with reference to FIG. 20A, a channel 540, containing fluidic droplet 530 and liquid 535, divides into channel 542 and 544. Fluidic droplet 530 is uncharged. Electrode 526 is positioned near channel 542, while electrode 527 is positioned near channel 544. Electrode 528 is positioned near the junction of channels 540, 542, and 544. In FIGS. 20C and 20D a dipole is induced in the fluidic droplet using electrodes 526, 527, and/or 528. In FIG. 20C, a dipole is induced in droplet 530 by applying an electric field 525 to the droplet using electrodes 527 and 528. Due to the strength of the electric field, the droplet is strongly attracted to the right, into channel 544. Similarly, in FIG. 20D, a dipole is induced in droplet 530 by applying an electric field 525 to the droplet using electrodes 526 and 528, causing the droplet to be attracted into channel 542. Thus, by applying the proper electric field, droplet 530 can be directed to either channel 542 or 544 as desired.

Figure 21A:
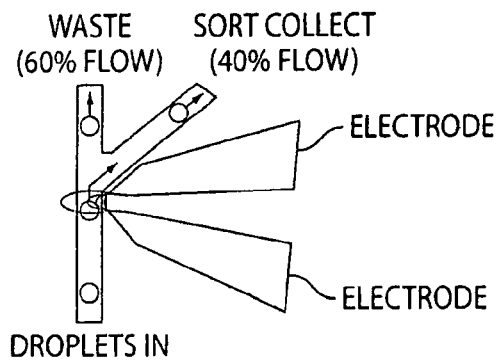
FIGS. 21A-F shows the possible flow geometries used in an asymmetric sorting application.
Figure 21B:
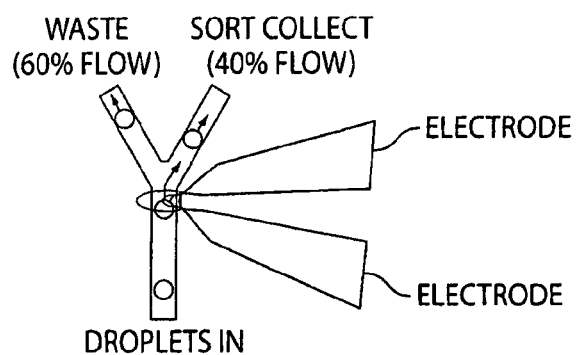
Figure 21C:
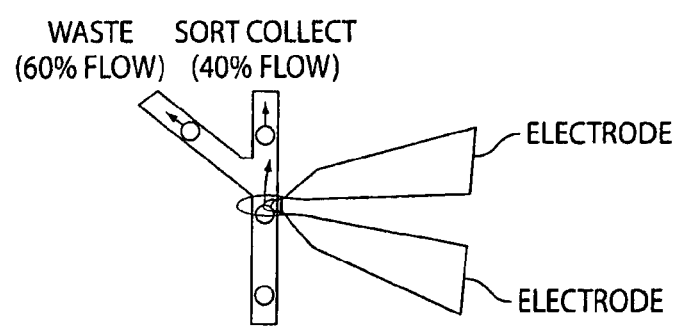
Figure 21D:
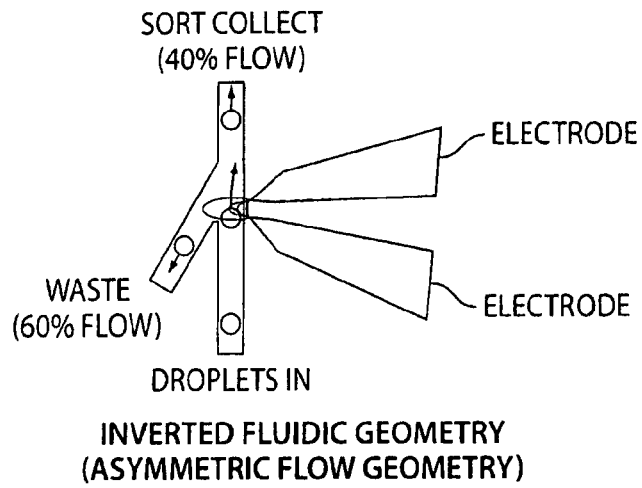
Figure 21E:
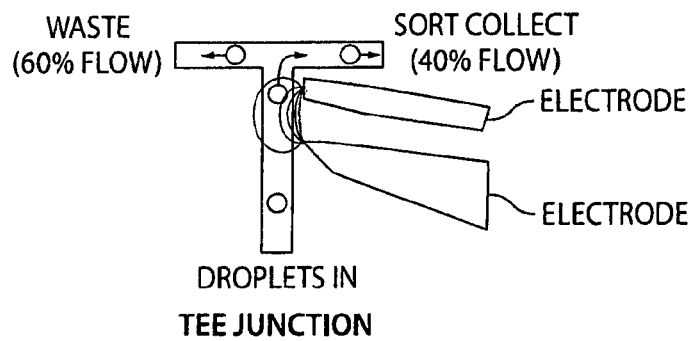
Figure 21F:
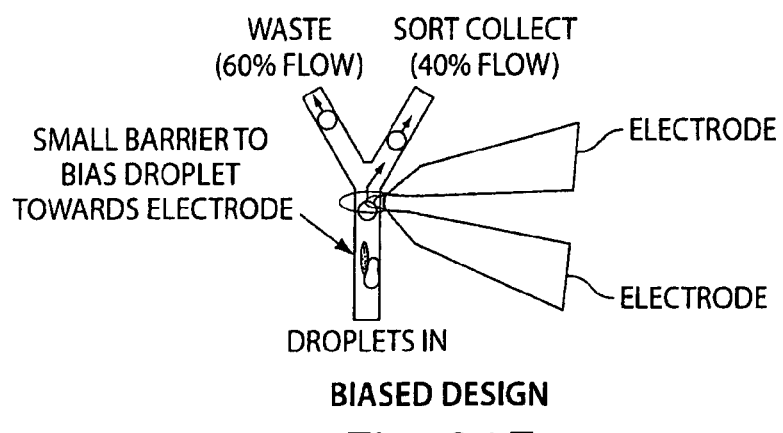

The present invention also provides improvements in the efficiency, accuracy, and reliability of the preferred dielectric droplet sorting technique described above. The single sided dielectric sorting relies on a combination of flow imbalance between the two exhaust legs and a switchable electric field to selectively sort out droplets of interest from the main sample stream. Sorting decisions are made based on some form of real time measurement of the droplet and its contents. FIGS. 21A-F and 22A-E depict many of the various possible fluid and electrode geometries possible for single sided dielectric sorting. FIGS. 21A-D show possible flow channel geometries that can be used in an asymmetric sorting application. FIG. 21F, illustrates the use of a barrier, for example, a barrier where no fluid flow passes on its left side. Note these designs are only conceptual representation of the fluid channels, and actual designs may differ in absolute and relative dimensions as determined by one of ordinary skill in the art.

Figure 22A:
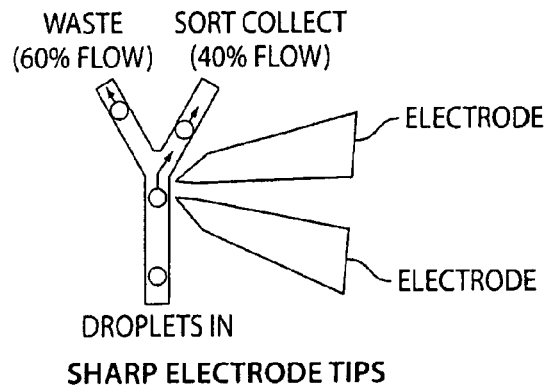
FIGS. 22A-E shows the possible electrode geometries used in an asymmetric sorting application.
Figure 22B:
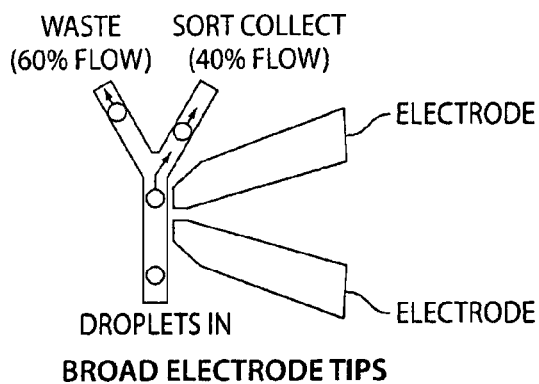
Figure 22C:
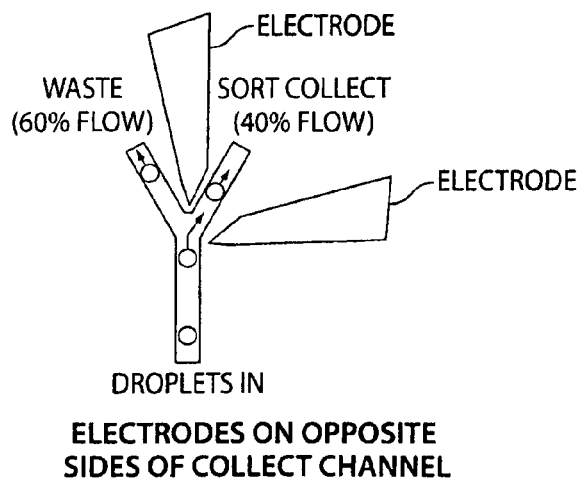
Figure 22D:
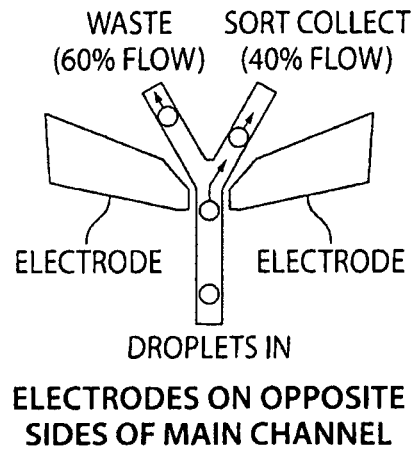
Figure 22E:
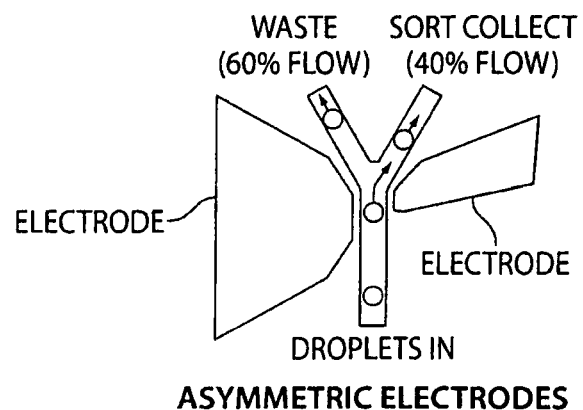

FIGS. 22A-E shows the possible electrode geometries used in an asymmetric sorting application. Panel A shows the use of sharp tipped electrodes. FIG. 22B shows broad tipped electrodes to increase the interaction time between the droplets and the electric field (the tips could be many drop diameters long). FIG. 22C shows electrodes straddling the collection line. FIG. 22D shows electrodes on opposite sides of the main channel. FIG. 22E shows an Asymmetric Electrode Pair (the asymmetry may be present on any of the other electrode pair layouts as well). Note these designs are only conceptual representation of the electrodes, and actual designs may differ in absolute dimensions and electrode shape as determined by one of ordinary skill in the art. Although the fluid channel geometry is drawn as a "Y" junction, any of the channel geometries shown in FIGS. 21A-E could be substituted in these drawings.

Typically, the flow rate of the collection leg is set to a value just below the level required to begin pulling droplets into the collection line (indicated as 40% in the figures, although the actual value may be differ from this and is dependent on the actual fluidic and electrode geometry, total flow, as well as droplet size and composition).

As an alternative design strategy, the collection leg can be operated at a flow rate at which the droplets would normally flow down the Sort collect line (i.e. change the flow splits shown in the diagrams from 40% collect/60% waste to 60% collect/40% waste), and keep the electric field energized until a droplet of interest is detected. At that time, the field would be briefly turned off, and the droplet would be pulled down the collection leg based on fluidic forces instead of electrical forces.

Alternately, a fluidic droplet may be directed by creating an electric charge (e.g., as previously described) on the droplet, and steering the droplet using an applied electric field, which may be an AC field, a DC field, etc. As an example, an electric field maybe selectively applied and removed (or a different electric field may be applied) as needed to direct the fluidic droplet to a particular region. The electric field may be selectively applied and removed as needed, in some embodiments, without substantially altering the flow of the liquid containing the fluidic droplet. For example, a liquid may flow on a substantially steady-state basis (i.e., the average flowrate of the liquid containing the fluidic droplet deviates by less than 20% or less than 15% of the steady-state flow or the expected value of the flow of liquid with respect to time, and in some cases, the average flowrate may deviate less than 10% or less than 5%) or other predetermined basis through a fluidic system of the invention (e.g., through a channel or a microchannel), and fluidic droplets contained within the liquid may be directed to various regions, e.g., using an electric field, without substantially altering the flow of the liquid through the fluidic system.

In other embodiments, however, the fluidic droplets may be screened or sorted within a fluidic system of the invention by altering the flow of the liquid containing the droplets. For instance, in one set of embodiments, a fluidic droplet may be steered or sorted by directing the liquid surrounding the fluidic droplet into a first channel, a second channel, etc.

In another set of embodiments, pressure within a fluidic system, for example, within different channels or within different portions of a channel, can be controlled to direct the flow of fluidic droplets. For example, a droplet can be directed toward a channel junction including multiple options for further direction of flow (e.g., directed toward a branch, or fork, in a channel defining optional downstream flow channels). Pressure within one or more of the optional downstream flow channels can be controlled to direct the droplet selectively into one of the channels, and changes in pressure can be effected on the order of the time required for successive droplets to reach the junction, such that the downstream flow path of each successive droplet can be independently controlled. In one arrangement, the expansion and/or contraction of liquid reservoirs may be used to steer or sort a fluidic droplet into a channel, e.g., by causing directed movement of the liquid containing the fluidic droplet. The liquid reservoirs may be positioned such that, when activated, the movement of liquid caused by the activated reservoirs causes the liquid to flow in a preferred direction, carrying the fluidic droplet in that preferred direction. For instance, the expansion of a liquid reservoir may cause a flow of liquid towards the reservoir, while the contraction of a liquid reservoir may cause a flow of liquid away from the reservoir. In some cases, the expansion and/or contraction of the liquid reservoir may be combined with other flow-controlling devices and methods, e.g., as described herein. Non-limiting examples of devices able to cause the expansion and/or contraction of a liquid reservoir include pistons and piezoelectric components. In some cases, piezoelectric components may be particularly useful due to their relatively rapid response times, e.g., in response to an electrical signal.

In some embodiments, the fluidic droplets may be sorted into more than two channels. Alternately, a fluidic droplet may be sorted and/or split into two or more separate droplets, for example, depending on the particular application. Any of the above-described techniques may be used to spilt and/or sort droplets. As a non-limiting example, by applying (or removing) a first electric field to a device (or a portion thereof), a fluidic droplet may be directed to a first region or channel; by applying (or removing) a second electric field to the device (or a portion thereof), the droplet may be directed to a second region or channel; by applying a third electric field to the device (or a portion thereof), the droplet may be directed to a third region or channel; etc., where the electric fields may differ in some way, for example, in intensity, direction, frequency, duration, etc. In a series of droplets, each droplet may be independently sorted and/or split; for example, some droplets may be directed to one location or another, while other droplets may be split into multiple droplets directed to two or more locations.

In some cases, high sorting speeds may be achievable using certain systems and methods of the invention. For instance, at least about 1 droplet per second may be determined and/or sorted in some cases, and in other cases, at least about 10 droplets per second, at least about 20 droplets per second, at least about 30 droplets per second, at least about 100 droplets per second, at least about 200 droplets per second, at least about 300 droplets per second, at least about 500 droplets per second, at least about 750 droplets per second, at least about 1000 droplets per second, at least about 1500 droplets per second, at least about 2000 droplets per second, at least about 3000 droplets per second, at least about 5000 droplets per second, at least about 7500 droplets per second, at least about 10,000 droplets per second, at least about 15,000 droplets per second, at least about 20,000 droplets per second, at least about 30,000 droplets per second, at least about 50,000 droplets per second, at least about 75,000 droplets per second, at least about 100,000 droplets per second, at least about 150,000 droplets per second, at least about 200,000 droplets per second, at least about 300,000 droplets per second, at least about 500,000 droplets per second, at least about 750,000 droplets per second, at least about 1,000,000 droplets per second may be determined and/or sorted in such a fashion.

Multiple Measurement Sorting

Figure 23:
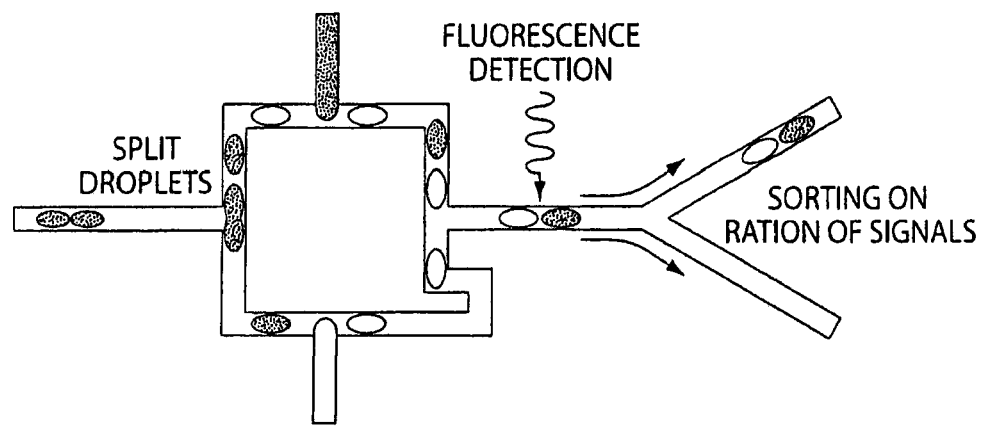
FIG. 23 shows a schematic of a device that split droplets, performs different experiments on the two daughter droplets and then reorders so that they pass sequential through the detector

In some embodiments, it may be useful to sort droplets based on two different measurements. For example, one might want to sort based on the ratio of two signals, sum of two signals, or difference between two signals. Specifically, this would be useful for cases when one would like to optimize an enzyme so that it work one substrate, but not another, or so that it works on two substrates. This is not easy to do using multiple rounds of selection on populations of droplets. To overcome this shortcoming of current sorting technology, the present invention provides a device comprising multiple channels with the appropriate geometry to split droplets, perform different experiments on the two daughter droplets and then reorder so that they pass sequential through the detector. The sums, ratios or differences in the two signals can then be calculated before the droplets enter the sorting bifurcation. An indicator dye or equivalent material may be added to one or both droplets to indicate when each droplet enters and leaves the laser. A representative sketch is shown in FIG. 23.

Sample Recovery

The present invention proposes methods for recovering aqueous phase components from aqueous emulsions that have been collected on a microfluidic device in a minimum number of steps and in a gentle manner so as to minimize potential damage to cell viability.

In one aspect, a stable aqueous sample droplet emulsion containing aqueous phase components in a continuous phase carrier fluid is allowed to cream to the top of the continuous phase carrier oil. By way of nonlimiting example, the continuous phase carrier fluid can include a perfluorocarbon oil that can have one or more stabilizing surfactants. The aqueous emulsion rises to the top or separates from the continuous phase carrier fluid by virtue of the density of the continuous phase fluid being greater than that of the aqueous phase emulsion. For example, the perfluorocarbon oil used in one embodiment of the device is 1.8, compared to the density of the aqueous emulsion, which is 1.0.

The creamed emulsion is then placed onto a second continuous phase carrier fluid which contains a de-stabilizing surfactant, such as a perfluorinated alchohol (e.g., 1H,1H,2H,2H-Perfluoro-1-octanol). The second continuous phase carrier fluid can also be a perfluorocarbon oil. Upon mixing, the aqueous emulsion begins to coalesce, and coalescence is completed by brief centrifugation at low speed (e.g., 1 minute at 2000 rpm in a microcentrifuge). The coalesced aqueous phase can now be removed (cells can be placed in an appropriate environment for further analysis).

Additional destabilizing surfactants and/or oil combinations can be identified or synthesized to be useful with this invention.

Mixing Module

The microfluidic device of the present invention can further include one or more mixing modules. Although coalescence of one or more droplets in one or more coalescence modules can be sufficient to mix the contents of the coalesced droplets (e.g., through rotating vortexes existing within the droplet), it should be noted that when two droplets fuse or coalesce, perfect mixing within the droplet does not instantaneously occur. Instead, for example, the coalesced droplet may initially be formed of a first fluid region (from the first droplet) and a second fluid region (from the second droplet). Thus, in some cases, the fluid regions may remain as separate regions, for example, due to internal "counter-revolutionary" flow within the fluidic droplet, thus resulting in a non-uniform fluidic droplet. A "mixing module" can comprise features for shaking or otherwise manipulate droplets so as to mix their contents. The mixing module is preferably downstream from the coalescing module and upstream from the detection module. The mixing module can include, but is not limited to, the use of channel geometries, acoustic actuators, metal alloy component electrodes or electrically conductive patterned electrodes to mix the contents of droplets and to reduce mixing times for fluids combined into a single droplet in the microfluidic device. For example, the fluidic droplet may be passed through one or more channels or other systems which cause the droplet to change its velocity and/or direction of movement. The change of direction may alter convection patterns within the droplet, causing the fluids to be at least partially mixed.

Combinations are also possible.

For acoustic manipulation, the frequency of the acoustic wave should be fine tuned so as not to cause any damage to the cells. The biological effects of acoustic mixing have been well studied (e.g., in the ink-jet industry) and many published literatures also showed that piezoelectric microfluidic device can deliver intact biological payloads such as live microorganisms and DNA. In an example, the design of the acoustic resonant uses a Piezoelectric bimorph flat plate located on the side of the carved resonant in the PDMS slab. The piezoelectric driving waveform is carefully optimized to select the critical frequencies that can separate cells in fluids. There are five parameters to optimize beyond the frequency parameter. Lab electronics is used to optimize the piezoelectric driving waveform. Afterwards, a low cost circuit can be designed to generate only the optimized waveform in a preferred microfluidic device.

Other examples of fluidic mixing in droplets are described WO 2004/091763, incorporated herein by reference.

Delay Module

The microfluidic device of the present invention can further include one or more delay modules. The "delay module" can be a delay line. The operation of a microfluidics device where a reaction within a droplet is allowed to occur for a non-trivial length of time requires a delay line to increase the residence time within the device. For reactions demanding extensive residence time, longer or larger delay lines are required. Accordingly, the invention provides methods to increase residence times within microfluidic devices.

The delay module is in fluid communication with the main channel or it can be an elongated portion of the main channel itself. The delay module can be located downstream of the coalescence module and upstream of the detection module. The delay module can be a serpentine channel or a buoyant hourglass. The delay module can further comprise heating and cooling regions. The heating and cooling regions can be used for performing on-chip, flow-through PCR as further described herein.

The channel dimensions and configurations can be designed to accommodate the required residence time with minimum pressure drops across the device. For example, to accommodate very long delay lines within the microfluidic device, the device can comprise a multilayered PDMS slab which is composed of several patterned PDMS slabs.

The channel dimensions can also be designed so as to allow for required flow, residence time and pressure drop. Some channels may be required to be very large in width and height. In order to avoid collapse of the channels, the device includes support posts within the channel design. In order to reduce dead volume behind posts and further improve droplet stability, the support posts are designed to optimize a streamlined flow within the channel. These designs can include curved features as opposed to sharp edges.

To allow for longer period of device operation, delay lines can also be extended to the outside of the chip. The off-chip delay lines can be tubes within micron-sized internal diameter.

In order to allow more efficient use of available space and faster operation, in methods where droplets are charged, after charging, asymmetric splitting of oil and drops can be accommodated by siphoning off oil from channels after droplets are charged.

The delay lines can be in the form of a tower (i.e., a structure which is vertical with respect to the ambient gravitational field) as to allow buoyant forces to assist controlled droplet transport. Known delay lines involve transporting droplets by emulsifying them in a carrier fluid flowing in a channel and/or tube. Because the velocity profile of the carrier fluid through the cross-section of the channel and/or tube is not uniform, the velocity distribution of the droplets will not be narrow, which causes the delay time distribution of the droplets to not be narrow (i.e., some droplets will be delayed more or less than others).

The devices of the present invention can also include buoyancy-assisted microfluidic delay lines. In buoyancy-assisted microfluidic delay lines, buoyant forces act on droplets emulsified in a fluid in one or more towers. This can include allowing the tower to fill for the desired delay time, and then releasing the droplets. The tower can or can not continue to fill and release droplets as needed. In this example, one may desire to have a cylindrical tower section that is capped by a pyramidal funnel section. The tower can effectively functions as an hourglass. Droplets that have a density less than their carrier fluid are fed into the base of the tower, buoyantly rise to the top of the tower with a substantially uniform velocity distribution, and are funneled into a functional component of the microfluidic device (such as a y-branch). Carrier fluid is exhausted at the base of the tower at the same rate as it is introduced at the apex so that the net flow of carrier fluid through the delay line is zero. The tower and funnel sections can have any cross-sectional shape, such as circular, elliptical, or polygonal. The microfluidic device can include a tower with adjustable length.

The device can also include a switching network of twenty towers to guarantee a delay time dispersion of 5% (because 1/20=0.05). The capacity of each tower is 0.05*T, where T is the delay time. The concept includes, for example: (a) upon device start-up, filling the first tower for 0.05*T, but stop-cock its exhaust, and also have the other nineteen towers closed; (b) after 0.05*T, closing the first tower and filling the second between 0.05*T and 0.10*T; (c) repeating step (b) for the remaining eighteen towers; (d) at time T, allowing the first tower to exhaust; (e) at time 1.05*T, stop-cocking the exhaust of the first tower, allowing the second tower to exhaust, and allowing the first tower to fill; (f) at time 1.10*T, stop-cocking the exhaust of the second tower, allowing the third tower to exhaust, closing the first tower, and allowing the second tower to fill, and (g) repeating step (f) ad infinitum. More than twenty towers may provide an even tighter control over the width of the delay time dispersion. This scheme may require a valve network. This network of towers can be outside the microfluidic device.

The delay module can also include channels (e.g. the main channel) which has an altered geometry which permits the "parking" (e.g., slowing or stopping) of droplets within the microfluidic device.

In the methods provided herein, droplets are able to be parked in wells or channels at predefined locations. This can be done by creating discrete well-like indentions in the channel whereby a droplet 'falls' into the well and remains there as the fluid flows over it, or by using a technique entitled 'by-pass pots' whereby a droplet is used to block a small outlet in a well, thereby causing the flow to by-pass that droplet-containing well.

The instant invention is to use either of these techniques or any related technique, for example just stopping the drops in a channel, to position droplets at either random or predefined places within a microfluidics device. These random or predefined locations can then be queried at a later time-point for a reaction to have occurred, or for removal of the droplets using another means such as resuspension followed by aspiration.

In one example, a rolling circle amplification reaction is initiated in droplets, the droplets are then parked within the chip, and the amplification reaction allowed to proceed for a set period of time prior to stopping the reaction through the use of heat. The parked droplets are then dried in situ and the covering of the chip disassembled from the chip. One or a set of needle-like devices that are able to be lined up with the droplet parking space are then placed adjacent to or on top of the dried droplets and a liquid solution used to resuspend the material in the dried droplet that has been deposited into the chip, for further downstream processing. In another example, to avoid possible diffusion of reactant contents from a first and a second set of reactions in droplets, the first reactions are created in 10 µm droplets, the droplets are dried within a channel parking space or by-pass pot which is able to hold a droplet of size larger than 10 µm, and the droplets are dried in situ. A second set of droplets that are larger than 10 µm are then allowed to proceed down said channel and when caught in said parking space or by-pass pot are able to resuspend the material from the first droplets that are dried along the walls of the first parking space or by-pass pot. In doing so, the second droplet is slightly larger than the first and that ensures that the material along the walls is 'captured' by the second droplet, and not allowed to diffuse away from the first droplet wall by diffusion. By doing so, use of surfactants becomes optional in either the first or second droplet formulations.

The instant invention also provides the following devices and methods for use in practicing the methods described herein. The PDMS substrate which comprises a portion of the microfluidic device can be covered or coated with an adhesive tape or strip that can be removed by peeling. The PDMS substrate can also be bonded by an ultra-thin silica that can be pierced by a set of needles. The silica may be spin coated or electro-plated onto a thin backing. Droplets can be dried onto a piece of paper such that can be detected by a second device to determine the Ncode within the droplet and to determine whether an amplification reaction has occurred within the droplet. A plate read comprising dried and undried spots using either an optical array device, such as found in high-end cameras or fiber, optic device is also contemplated. Dry Nitrogen can be utilized to dry the spots by either flowing it through the channel or placing the device into a dry-$N_2$ chamber. Channels can be filled with dried nitrogen or salt run underneath or adjacent to the parking space channels to allow chemical or physical-type gradients to be set up in the chip. The channel walls can be coated with Steptavidin and the produced reactants, for example, DNA biotinylated so that it adheres in situ. Porous beads deposited into the wells can be used in combination with solutions without oils to wash the beads by flow, followed by re-depositing droplets with surfactants to recoat the beads. The wells within the substrate can be filled with many small beads by loading small beads into droplets, storing the droplets into individual wells containing apertures that are slightly smaller than the beads, breaking the droplets by drying or flow of aqueous solutions with or without surfactants into the channels and past the beads, and then re-encapsulating the beads in situ. A set of electrodes within or adjacent to the microfluidic substrate can be used to fuse two droplets in a storage/holding space. The electrodes may be perpendicular to the plane of the channels and either the electrodes or channels moved so as to allow droplet fusions to occur.

UV-Release Module

The microfluidic device of the present invention can further include one or more UV-release modules. The "UV-release module" is in fluid communication with the main channel. The UV-release module is located downstream of the inlet module and upstream of the coalescence module. The UV-module can be a used in bead assays. Compounds from encapsulated beads can be cleaved in a UV-releasing module using UV light. Photolabile linkers can be broken down on demand after a single bead has been encapsulated thus releasing multiple copies of a single compound into solution. In the cell based assay disclosed herein the chemical compound assayed is desired to be in solution in order to penetrate the cell membrane. Furthermore, to ensure compartmentalization of a single compound with a cell the cleavage of the compound from the solid support can only be done after the bead has been encapsulated. Photocleavable linkers can be utilized to cleave the compounds of the bead after drop formation by passing the drop through a UV-release module (i.e., laser of the appropriate wavelength). The present invention also provides methods for chemical synthesis on a bead and releasing said chemical attached to the bead using a releasing means (chemical, Lw light, heat, etc) within a droplet, and then combining a second droplet to the first droplet for further manipulation. Preferably, the releasing means is a UV-module. For example, tea-bag synthesis of chemicals on a bead simultaneously with a means for identifying said bead (using, for example, a mass spec tag). Using the resulting mixed-chemistry beads in a droplet within a fluid flow, and exposing the beads to UV light to release the chemical synthesized from the bead into the droplet environment. Combining the droplet containing the released chemical with a droplet containing a cell, and performing a cell-based assay. Sorting droplets having the desired characteristics (for example, turn on of a reporter gene), and then analyzing the sorted beads using mass spectroscopy.

Methods and Assemblies for Droplet Handling

The methods and assemblies provided herein are particularly useful for reducing potential contamination associated with sample handing, especially when performing an amplification reaction. When conducting an amplification, there is a risk that non-target nucleic acid will be inadvertently introduced into the sample during handling and subsequently amplified. The methods and assemblies described herein use immiscible fluids of certain densities to displace sample droplets from one location to another without the need for operator handling. Accordingly, the risk of contamination associated with such handling is eliminated.

In certain embodiments, the provided assembly includes at least one droplet formation module, in which the module is configured to form droplets surrounded by an immiscible fluid. In certain aspects, the droplet forming module includes an inlet module to generate droplets. The inlet module typically includes a junction between a sample inlet channel in which a sample in aqueous solution is introduced and a main channel in which an immiscible fluid flows. When the sample solution is introduced to the main channel, a plurality of droplets is formed by segmenting the aqueous solution with the immiscible fluid.

The newly formed droplets and surrounding immiscible fluid are then directed or flowed towards a chamber. Methods of controlling the flow of fluids have been described throughout the present disclosure. For example, valves and pumps can be used to manipulate the flow of introduced sample or immiscible fluid. Other methods for controlling flow include the use of electro-osmotic flow control, electrophoresis, and dielectrophoresis, all previously described.

Any fluid that is immiscible with the droplet can be used in accordance with the invention. The droplet forming liquid is typically an aqueous buffer solution, such as ultrapure water, 10 mM Tris HCl and 1 mM EDTA buffer, PBS, or acetate buffer. Any liquid or buffer, however, that is physiologically compatible with the population of molecules, cells, or particles to be analyzed, can be used.

Accordingly, the immiscible fluid is typically an oil or non-polar solvent, both of which are immiscible with aqueous buffers. Suitable immiscible fluids have already been described throughout the present disclosure but include, without limitation, fluorocarbon oil, silicon oil, or mineral oil. In certain embodiments of the invention, the oil is a fluorinated oil or a perfluorcarbon oil.

In certain embodiments, the oil may also include a surfactant, which assists in controlling droplet size, flow, and uniformity. Suitable surfactants include, but are not limited to, Tween, Span, fluorosurfactants, and other agents that are soluble in oil relative to water. Additional surfactants are described throughout the present disclosure.

Suitable immiscible fluids will also have a density different than that of the droplets. The density differential between the selected oil and the droplets results in the displacement of the droplets in an upward or downward direction. For example, droplets of aqueous solution placed in a vessel containing fluorinated oil will tend to rise due to the comparatively lower density of the droplets. On the other hand, droplets of aqueous solution placed in a vessel of mineral oil will tend to sink due to the comparatively greater density of the droplets. The appropriate immiscible fluid can be selected based on the desired direction of droplet movement.

The droplet formation module is connected via a channel to at least one chamber comprising an outlet. The chamber is configured to receive droplets and an immiscible fluid from the droplet formation module. The chamber outlet is configured to receive substantially only droplets. As immiscible fluid continues to flow into the chamber, the immiscible fluid displaces the droplet from the chamber into the outlet due to the difference in density. The outlet can be positioned accordingly to collect the droplets. For example, the outlet can be positioned at an upper portion of the chamber to collect rising droplets or at a lower position of the chamber to collect sinking droplets. As the immiscible fluid displaces the droplets towards the outlet, the majority of the immiscible fluid remains inside the chamber, leaving substantially only droplets to exit the chamber. It is to be understood that the chamber can include any vessel suitable for holding droplets, for example, test tubes, vials, beakers, jars, and PCR tubes. In addition, the outlet may be connected to a second vessel, such that the continued flowing of the immiscible fluid eventually displaces the droplets from the chamber into the vessel.

In certain embodiments, the outlet is connected to a channel. The continued flowing of the immiscible fluid into the vessel directs the droplets towards the outlet and subsequently into the connected channel where the droplets may be collected in the vessel.

Figure 38:
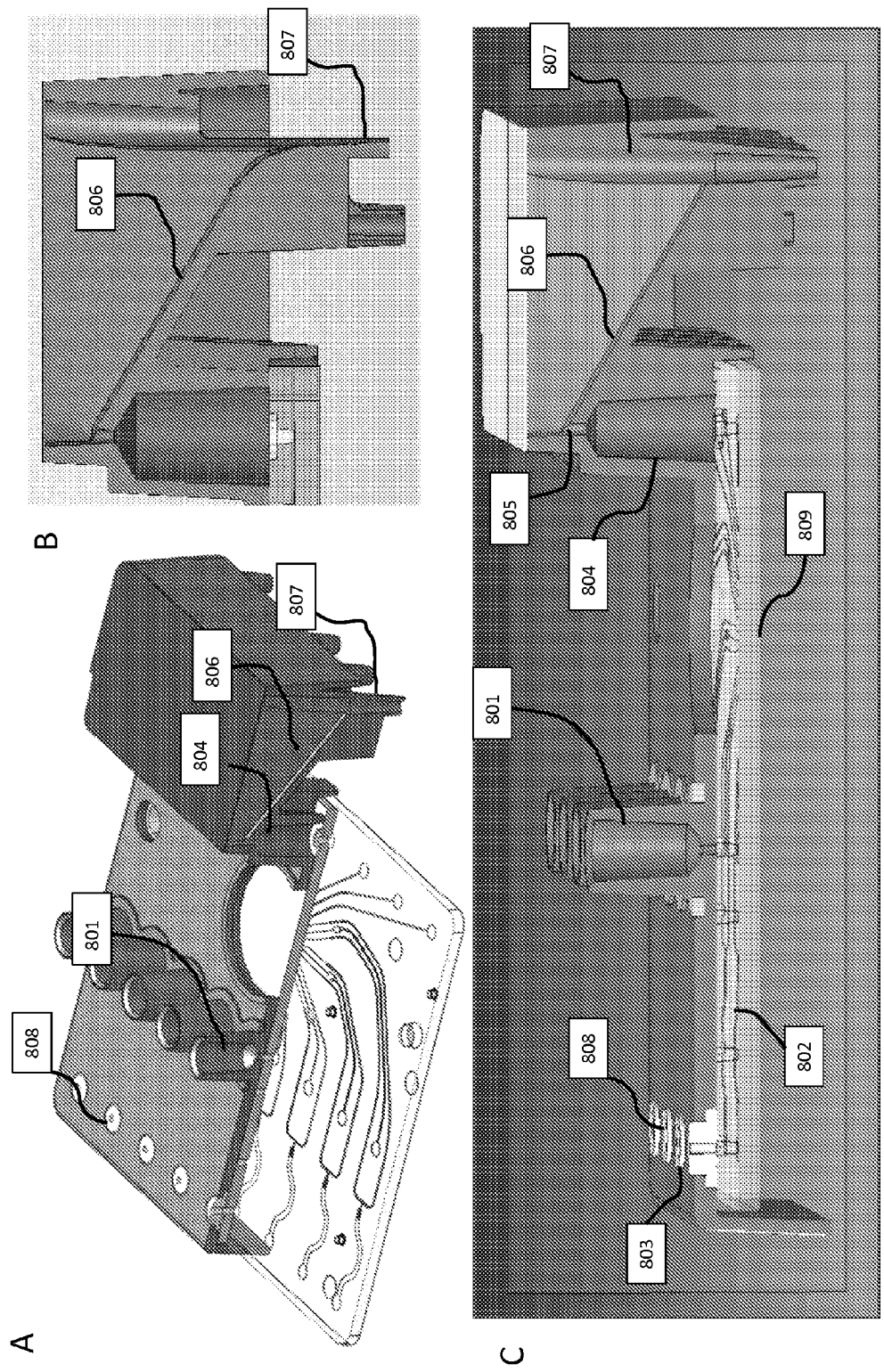
FIG. 38 panels A-C show different views of a microfluidic assembly.

An exemplary assembly in accordance with the invention is provided in FIG. 38 panels A-C. Samples prepared in aqueous solution enter the assembly at sample input 801 into a connected channel 802. In certain embodiments, the bottom of the sample input 801 is shaped to prevent a pipette from fully occluding the port. This is a useful design feature that prevents accidental driving of a sample into the chip during the sample loading step. Once introduced, the sample solution flows from the sample input 803 along the channel 802. Methods of making the channel 802 as well as methods for achieving the flow of solutions in the channel 802 have already been described throughout the present disclosure.

An immiscible fluid, such as an oil, is introduced in a second channel 803. The oil and aqueous buffer meet at a junction in the channel 802 such that the aqueous solution in segmented by the oil, thereby forming droplets. Together, the sample input 801, oil input 803, and connected channel 802 comprise the droplet formation module, which is configured to form droplets surrounded by an immiscible fluid.

In the same manner, a second set of droplets can be generated containing the necessary reagents, i.e., the appropriate primers, probes, polymerase, and dNTPs for conducting the amplification step. Suitable probes for use with the invention are described in detail in U.S. patent application Ser. No. 13/026,120. Reagents prepared in aqueous solution can be introduced at reagent input 808 which will also lead into a connected channel 802. Oil is introduced in a second channel 803, whereupon the oil and aqueous buffer meet at a junction in the channel 802 such that the aqueous solution in segmented by the oil, thereby forming reagent droplets. In other embodiments, a fluid stream of reagents is prepared rather than reagent droplets. More detail on the use of fluid reagent streams is provided in U.S. patent application Ser. No. 13/371,222, herein incorporated by reference in its entirety.

Whether contained in a fluid stream or in droplet, amplification reagents are introduced to the sample droplet via the application of an electric field, which ruptures the interface between the sample droplet and the reagent fluid or droplet, thereby fusing the contents. In some embodiments, the assembly includes a coalescence module 809 which facilitates the merger of the sample droplets and either the reagent droplets or fluid through the application of an electric field. The coalescence module 809 is within or coincident with at least a portion of the connected channel or downstream of the sample and reagent inputs 801 and 808 wherein the contents of the sample droplets and the contents of the reagent stream/droplets are brought within proximity of one another and wherein the droplets and/streams fuse, coalesce, or combine their contents. The coalescence module 809 can also include an apparatus for generating electric force. Further detail regarding the coalescence module 809 and the application of electric fields is provided throughout the current disclosure.

Figure 39:
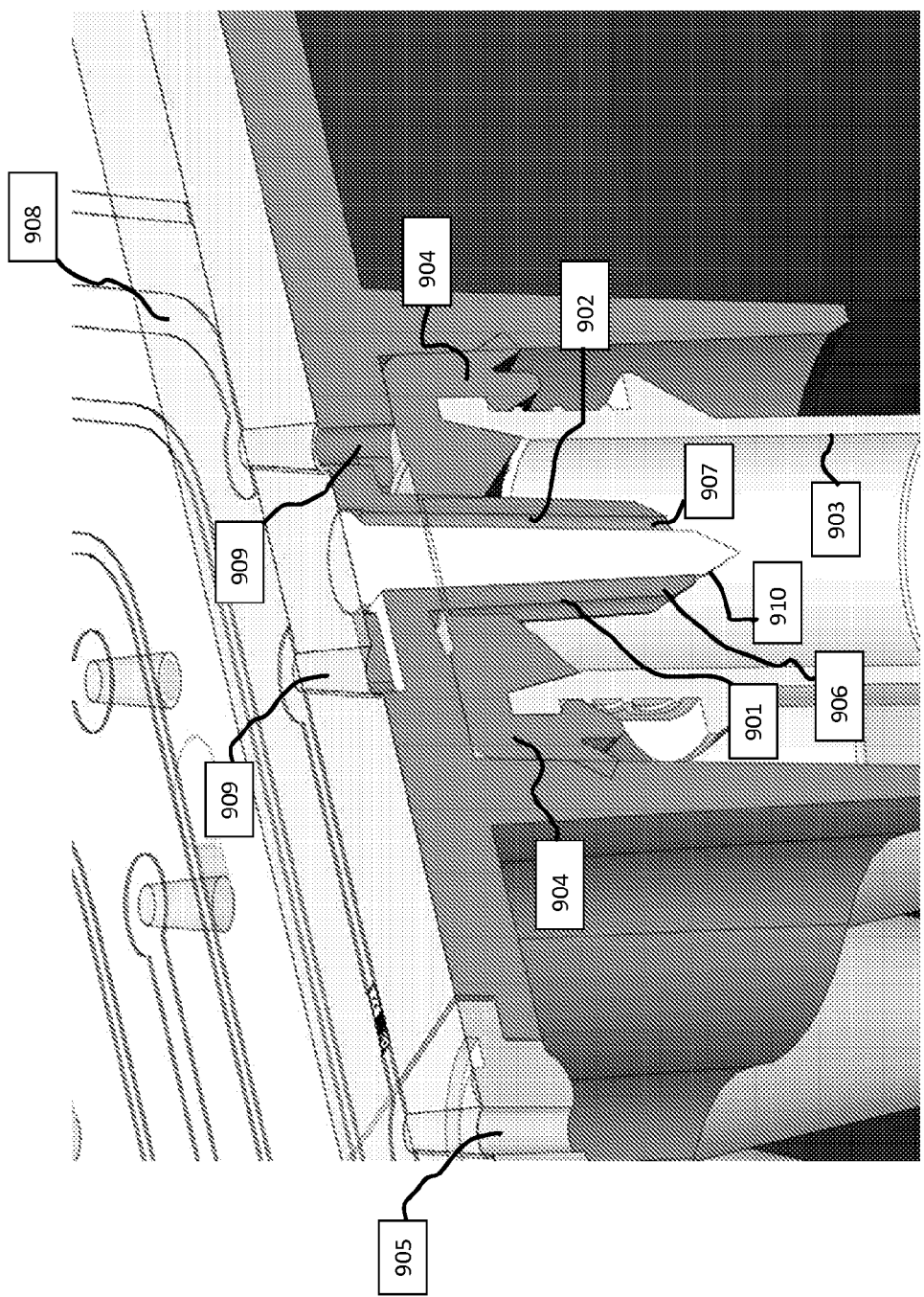
FIG. 39 shows different views of another microfluidic assembly.

The assembly also includes a chamber 804 equipped with an outlet 805. The chamber 804 is in fluid communication with the droplet formation module through the channel 802. As the oil containing the droplets moves along the assembly through the channel 802, the oil and droplets begin to enter the chamber 804. Due to the difference in their respective densities, the oil and droplets separate from each other in the chamber 804. As shown in FIG. 39, the outlet 805 can be positioned at an upper portion of the chamber 804 where the rising droplet will exit the chamber 804 into the outlet 805 leaving a large part of the oil behind. In other embodiments, the outlet 805 is positioned at a lower portion of the chamber 804.

In certain embodiments, the outlet is connected to a slide 806. The slide 806 includes a proximal end connected to the outlet 805 and a distal end. In certain embodiments, the proximal end of the slide 806 is higher than the distal end. The outlet 805 is in fluid communication with the slide 806 such that droplets exiting the chamber 804 through the outlet 805 will enter into the slide 806. The droplets travel from the higher positioned proximal end of the slide 806 to the lower distal end where they are collected. To further facilitate the collection of droplets, the slide may be connected to an output nozzle 807. The opening of the nozzle 807 may lead to a vessel or container for collecting the droplets, for example, a PCR tube or a test tube. Other vessels or containers known in the art can be used in accordance with the contemplated assemblies without limitation. In certain embodiments, slide 806 may curve continuously into the exit port 807. A preferred geometry has a curved and increasing slope for slide 806, an exit port 807 that is open on one side, and a taper to the exit port to help facilitate emulsion detaching from the feature and improve emulsion recover.

In certain embodiments, the outlet 805 may be sealably coupled to the vessel. Sealably coupling the outlet 805 to the vessel prevents contamination from outside sources as the droplets are transferred to the vessel. Any means known in the art can be used to effect the seal. For example, the assembly may include devices that bring the rim of the vessel and the outlet 805 into tight contact such that fluid loss is prevented during transfer to the vessel. In other embodiments, the assembly may include a device that surrounds both the outlet and at least the rim of the vessel such that fluid loss is prevented when droplets enter the vessel. In further embodiments, the outlet 805 itself may be configured in such manner to allow for sealable coupling of the vessel. For example, the outlet 805 may configured so that a vessel can lock into a position connected to the outlet 805. The outlet 805 may be configured to allow the vessel to be screwed into position. The outlet 805 can also be configured to allow the vessel to be snapped into position. In other embodiments of the invention, the aforementioned slide 806 or output nozzle 807 is configured for sealable coupling to a vessel.

While the assembly depicted in FIG. 38 facilitates the generation of droplets and their collection in a manner that mitigates the risk of contamination, additional assemblies encompassed by the invention facilitate the analysis of droplets while also mitigating the risk of contamination. As described throughout the present disclosure, analysis may include, without limitation, the detection, identification, measurement, or interrogation of molecules, cells, small molecules, and particles. In certain embodiments, the channel is connected to an analysis module which analyzes the droplets and their contents as they pass through the channel. The analysis module may include optical or electrical sensors or combinations thereof. Further examples of suitable detection devices include optical waveguides, microscopes, diodes, light stimulating devices, photomultiplier tubes, processors, or any combination of these devices.

In certain aspects, the second assembly includes a plurality of hollow members which act as channels. The members are configured to interact with a vessel, in which a first hollow member is configured to expel an immiscible fluid into the vessel and the second hollow member is configured to receive substantially only droplets from the vessel. The assembly further includes a main channel connected to the second hollow member. In certain aspects, the assembly also includes at least one analysis module connected to the main channel.

An exemplary embodiment of the second assembly is provided in FIG. 39. As shown, the assembly includes a plurality of hollow members. The hollow members are channels through which fluids can flow. The hollow members are configured to interact with a vessel. As depicted in FIG. 39, the hollow members 901 and 902 run along a member 910 into a vessel 903 in order to displace droplets from the vessel 903. In addition, the assembly may include devices configured to sealably connect the vessel 903 to the assembly. The sealable connection and the resultant seal minimize potential contamination as the droplets are displaced from the vessel 903. Any means can be used to sealably connect the vessel. In certain embodiments, the assembly includes a PCR tube cap 904 that lock the vessel 903 into a sealed position. The tube cap 904 may include a barb that helps prevent accidental removal. That ensures that the system stays sealed. In certain embodiments, there is a slope on the inside of the tube cap 904.

During use of the assembly, the vessel 903 contains the desired droplets. A first hollow member 901 is configured to expel an immiscible fluid, such as an oil, into the vessel 903. In certain embodiments, the oil is introduced to the assembly via a drive oil input 905, which send the oil to angular connector 909, wherein the oil travels through the first hollow member 901 to reach the vessel 903. In certain embodiments, the first hollow member 901 includes a drive oil output 906 which facilitates the transfer of oil into the vessel 903. As the oil fills the vessel 903, the oil displaces the droplets inside the vessel due to the density difference between the droplets and the oil.

A second hollow member 902 facilitates the collection of the droplets from the vessel 903. As the droplets rise, they enter the second hollow member 902 and are separated substantially from the oil. Assemblies encompassed by the invention also include second hollow members configured to receive droplets that sink to the bottom of the vessel. In either configuration, contamination is minimized by avoiding handling the sample. In some embodiments, the second hollow member 902 includes a droplet outlet groove 907 that facilitates collection of the droplets. The second hollow member 902 is in fluid communication with a main channel 908. As the oil expelled from the first hollow member 901 displaces the droplets contained in the vessel 903, the droplets enter the second hollow member 902 and flow into the main channel 908. In some embodiments, an angular connector 909 is positioned between the main channel and the second hollow member 902. The angular collector 909 provides a location for the displaced droplets to accumulate prior to transfer into the main channel 908. The connector 909 is a gap that connects to the main channel 908 where the emulsion enters the chip. The connector 909 is a flow chamber that is shallower on the left and deeper on the right with a sloped top to help direct the flow out. There is a path along the outside of member 901 that connects the inside of the tube to the angular connector 909 allowing flow of emulsion out of the tube.

Since avoiding contamination is important, vessels for use with the invention may be sealed. For example, the lid to a PCR tube containing PCR reaction droplets may be closed to prevent contamination from the extraneous environment. Accordingly, the assembly may include a member 910 in which the distal end of the member is configured to pierce a vessel surface, such as the tube lid. In certain embodiments, for example, the piercing member is a spike. Use of the piercing member 910 allows the lid to remain closed and reduces unnecessary exposure. As depicted, the distal end of the member 910 pierces the lid of the PCR tube 903 and extends to a distance suitable for collecting droplets that have gathered on top of the oil. In some embodiments, either the first hollow member 901, the second hollow member 902, or both hollow members 901 and 902 are configured to run adjacent to the piercing member 910. Once the piercing member pierces the lid of the vessel 903, the first hollow member 901 can expel an immiscible fluid into the vessel 903 and the second hollow member 902 can collect the droplets from the vessel 903 that are displaced by the incoming oil, whereupon the droplets flow into the aforementioned main channel 908.

Figure 40:
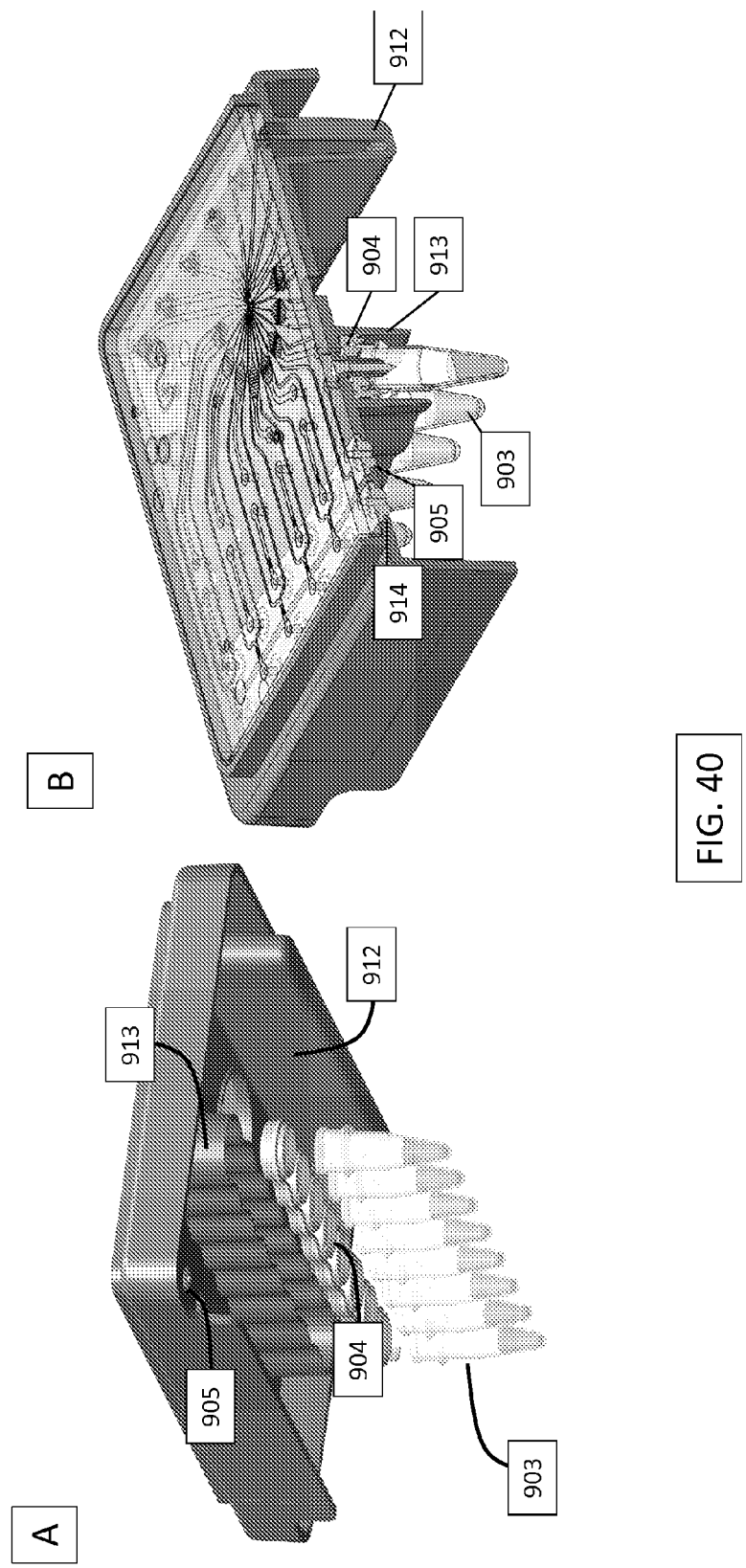
FIG. 40 panels A-B show different views of the second assembly.

FIG. 40 panels A-B show different views of the second assembly. Panel A shows an exploded view. 904 is the PCR tube cap. 905 is the drive oil port. 903 are the PCR tubes. 912 is a waste reservoir. 913 is a carrier tube-cap flange. Panel B shows a cross-sectional view. 904 is a PCR tube cap. 905 is a drive oil port. 903 is a PCR tube. 912 is a waste reservoir. 913 is a carrier tube-cap flange. 914 is a spacer oil port.

Figure 41:
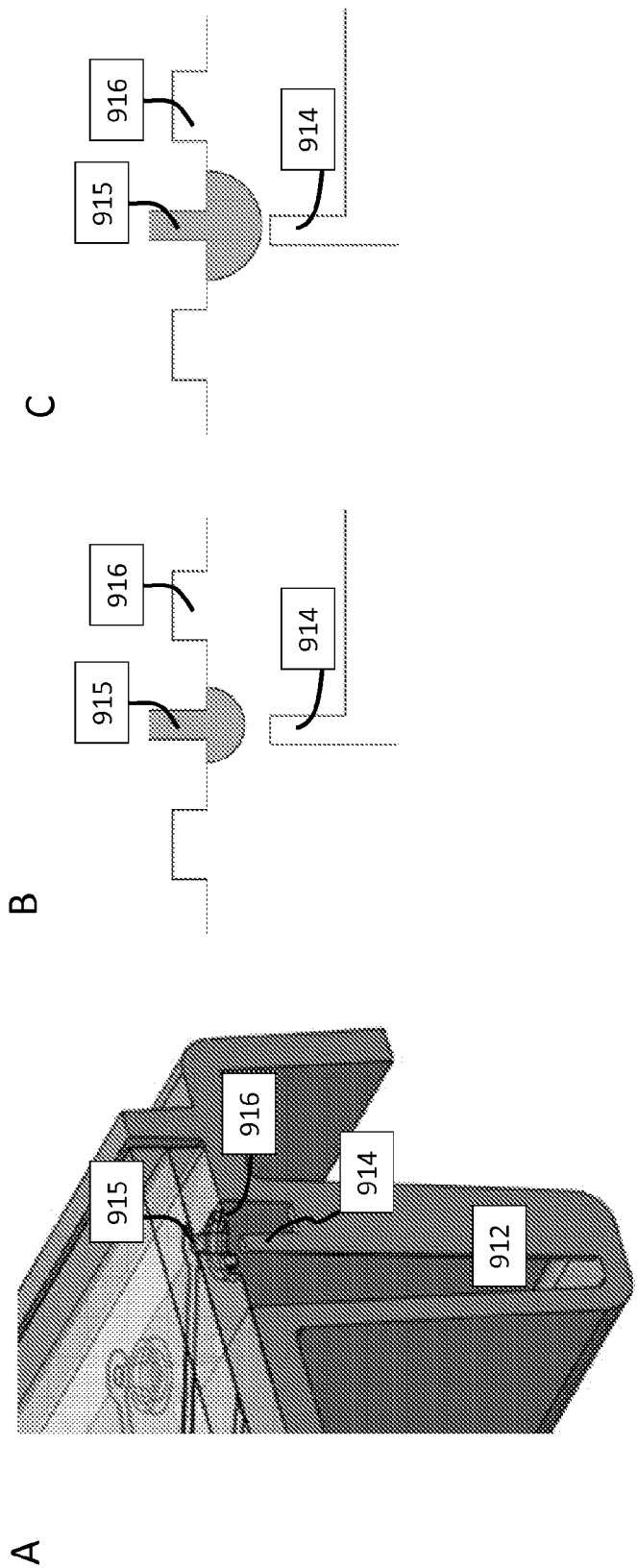
FIG. 41 panels A-C show a magnified view of the waste reservoir.

FIG. 41 panels A-C provide a magnified view of the waste reservoir. 912 is the waste reservoir. 914 is a drip collection finger. 915 is an exit port. 916 is a channel relief. The channel relief may be a moat around the exit 915 that prevents droplets from spreading and ensures that they make contact with the finger 914 first. The purpose of the feature is to prevent any opportunity for there to be contamination between the channels.

Assemblies of the invention also include an analysis module connected to the main channel 908. The analysis module is able to analyze contents within the droplets or the droplets themselves. Analysis modules have already been described extensively throughout the present disclosure but can include optical detectors, electrical detectors, or any combination of these detectors. In more specific embodiments, the analysis module may include an optical waveguide, a microscope, a diode, a light stimulating device, a photomultiplier tube, a processor, or any combination of these elements. Additional detail on the use of these devices has also been provided throughout the present disclosure.

Droplet Displacement and Amplification Reactions

The methods and assemblies described herein are particularly amenable for use with amplification reactions. Any amplification reaction known in the art may be conducted on the released nucleic acid. Exemplary amplification techniques include polymerase chain reaction (PCR), reverse transcription-PCR, real-time PCR, quantitative real-time PCR, digital PCR (dPCR), digital emulsion PCR (dePCR), clonal PCR, amplified fragment length polymorphism PCR (AFLP PCR), allele specific PCR, assembly PCR, asymmetric PCR (in which a great excess of primers for a chosen strand is used), colony PCR, helicase-dependent amplification (HDA), Hot Start PCR, inverse PCR (IPCR), in situ PCR, long PCR (extension of DNA greater than about 5 kilobases), multiplex PCR, nested PCR (uses more than one pair of primers), single-cell PCR, touchdown PCR, loop-mediated isothermal PCR (LAMP), and nucleic acid sequence based amplification (NASBA). Other amplification schemes include: Ligase Chain Reaction, Branch DNA Amplification, Rolling Circle Amplification, Circle to Circle Amplification, SPIA amplification, Target Amplification by Capture and Ligation (TACL) amplification, and RACE amplification.

In certain embodiments, the reaction is QPCR or digital PCR. Digital PCR is an amplification reaction in which dilute samples are divided into many separate reactions. See for example, Brown et al. (U.S. Pat. Nos. 6,143,496 and 6,391,559), Vogelstein et al. (U.S. Pat. Nos. 6,440,706, 6,753,147, and 7,824,889), as well as Larson et al (U.S. patent application Ser. No. 13/026,120), Link et al. (U.S. patent application Ser. Nos. 11/803,101, 11/803,104, and 12/087,713), and Anderson et al (U.S. Pat. No. 7,041,481, which reissued as RE41,780), the content of each of which is incorporated by reference herein in its entirety. The distribution from background of target DNA molecules among the reactions follows Poisson statistics and at a terminal or limiting dilution, the vast majority of reactions contain either one or zero target DNA molecules. Because the amount of target DNA in each reaction volume is so small, contamination by non-target nucleic acid is an especially significant problem. The non-target nucleic acid introduced during contamination is also amplified during PCR along with the target. However, because the amount of target nucleic acid is so small, the contaminant nucleic acid may easily out-compete the target nucleic acid during amplification. Contamination may be introduced inadvertently when the sample is handled by an operator, such as when a PCR tube is opened in order to transfer the sample from one location to another. The methods and assemblies described herein can be used to efficiently collect the droplets utilized in dPCR while minimizing contamination.

Methods of conducting dPCR are described in U.S. patent application Ser. No. 13/026,120, herein incorporated by reference. Such methods encompass the manipulation of nucleic acid in droplets, and in particular, nucleic acid amplification and detection. In one aspect, a droplet that contains a single nucleic acid template and a plurality of primer pairs specific for multiple target sites on the template is provided. The single nucleic acid template can be DNA (e.g., genomic DNA, cDNA, etc.) or RNA. The template is amplified in the droplet for detection; and may preferably be amplified using a plurality of primer pairs. These methods of conducting dPCR can be integrated into the assemblies provided in FIGS. 38 and 39 as follows.

Sample nucleic acid prepared in aqueous solution enters the assembly through the sample input 801. Once introduced, the aqueous solution flows from the sample input 801 into a connected channel 802. An oil is introduced in a second channel 803. The oil and aqueous solution meet at a junction in the channel 802, whereupon the oil segments the aqueous solution, thereby forming droplets containing the appropriate amount of sample nucleic acid. In the same manner, a second set of droplets can be generated containing the necessary reagents, i.e., the appropriate primers, probes, polymerase, and dNTPs for conducting the amplification step. Suitable probes for use with the invention are described in detail in U.S. patent application Ser. No. 13/026,120.

In certain embodiments, the probes are optically labeled probes, such as fluorescently labeled probes. Exemplary fluorescent labels include, but are not limited to, Atto dyes, 4-acetamido-4'-isothiocyanatostilbene-2,2'disulfonic acid; acridine and derivatives: acridine, acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; BODIPY; Brilliant Yellow; coumarin and derivatives; coumarin, 7-amino-4-methylcoumarin (AMC, Coumarin 120), 7-amino-4-trifluoromethylcouluarin (Coumaran 151); cyanine dyes; cyanosine; 4',6-diaminidino-2-phenylindole (DAPI); 5'5"-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansylchloride); 4-dimethylaminophenylazophenyl-4'-isothiocyanate (DABITC); eosin and derivatives; eosin, eosin isothiocyanate, erythrosin and derivatives; erythrosin B, erythrosin, isothiocyanate; ethidium; fluorescein and derivatives; 5-carboxyfluorescein (FAM), 5-(4,6-dichlorotriazin-2-yl)aminofluorescein (DTAF), 2',7'-dimethoxy-4'5'-dichloro-6-carboxyfluorescein, fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red;

B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N' tetramethyl-6-carboxyrhodamine (TAMRA); tetramethyl rhodamine; tetramethyl rhodamine isothiocyanate (TRITC); riboflavin; rosolic acid; terbium chelate derivatives; Cy3; Cy5; Cy5.5; Cy7; IRD 700; IRD 800; La Jolta Blue; phthalo cyanine; and naphthalo cyanine. Preferred fluorescent labels are FAM and VIC™ (from Applied Biosystems). Labels other than fluorescent labels are contemplated by the invention, including other optically-detectable labels.

Primers can be prepared by a variety of methods including but not limited to cloning of appropriate sequences and direct chemical synthesis using methods well known in the art (Narang et al., Methods Enzymol., 68:90 (1979); Brown et al., Methods Enzymol., 68:109 (1979)). Primers can also be obtained from commercial sources such as Operon Technologies, Amersham Pharmacia Biotech, Sigma, and Life Technologies. The primers can have an identical melting temperature. The lengths of the primers can be extended or shortened at the 5' end or the 3' end to produce primers with desired melting temperatures. Also, the annealing position of each primer pair can be designed such that the sequence and, length of the primer pairs yield the desired melting temperature. The simplest equation for determining the melting temperature of primers smaller than 25 base pairs is the Wallace Rule ($Td=2(A+T)+4(G+C)$). Computer programs can also be used to design primers, including but not limited to Array Designer Software (Arrayit Inc.), Oligonucleotide Probe Sequence Design Software for Genetic Analysis (Olympus Optical Co.), NetPrimer, and DNAsis from Hitachi Software Engineering. The TM (melting or annealing temperature) of each primer is calculated using software programs such as Oligo Design, available from Invitrogen Corp.

Once formed, the sample droplets and reagent droplets can be merged to form single droplets containing the single nucleic acid template and heterogenous mixture of primer pairs and probes. Suitable methods for merging the droplets have already been described throughout the present disclosure. Alternatively, single droplets containing the target nucleic acid and PCR reagents can be generated from the start.

In certain embodiments, the droplet containing the sample is contacted with a fluid stream containing the PCR reagents, thereby forming mixed droplets containing both the sample and reagents. In certain aspects, the droplets are flowed through a first channel and the fluid stream through a second channel. The two channels are oriented such that they intersect one another. An electric field is then applied to the droplet and fluid stream, which assists in rupturing the interface separating the two fluids. Further detail on such methods can be found in U.S. patent application Ser. No. 13/371,222, incorporated by reference herein in its entirety.

The droplets then move along the channel 802 to enter the chamber 804. Oil continues to flow into the chamber 804, whereupon the density difference between the oil and aqueous droplets results in the displacement of the droplets. In the embodiment shown in FIG. 38, the droplets are expected to be less dense than the oil and will therefore, rise to the top of the chamber. Accordingly, the chamber outlet 805 is positioned at the top of the chamber 804 to collect the displaced droplets.

The displaced droplets travel out the outlet 805 and down the slide 806 for collection into a vial, such as a PCR tube. The PCR tube can be sealably coupled to the assembly to further prevent entry of outside contaminants as the droplets travel through the assembly and into the PCR tube. Upon collection, the lid of the PCR tube can be sealed prior to amplification.

The vessel is then transferred to a thermocycler for conducting the amplification reaction. The nucleic acid in each of the formed droplets is amplified, e.g., by thermocycling the droplets under temperatures/conditions sufficient to conduct a PCR reaction. Any method known in the art may be used to amplify the target nucleic acids either linearly or exponentially. A preferred method is the polymerase chain reaction (PCR). For purposes of the invention, any amplification technique commonly known in the art may be implemented such as rolling circle amplification, isothermal amplification, or any combination of amplification methods using loci specific primers, nested-primers, or random primers (such primers, and/or primers used for PCR, are included in the term "amplification reagents"). In some embodiments, droplets containing amplicon from the target and amplicon from a variant of the target are excluded after amplification. Further detail on such methods is described in U.S. patent application Ser. No. 13/026,120.

The resulting amplicons in the droplets can then be analyzed. The assemblies provided herein allow for the analysis of the amplicons while avoiding potential contamination due to sample exposure during analysis. As noted above, the lid of the PCR tube is sealed after droplet collection to prevent outside contaminants from entering the tube. Opening the lid in order to conduct the analysis step would destroy much of the benefit obtained by sealing the lid in the first place.

As depicted in FIG. 39, a piercing member 910 is used to pierce the lid of the closed PCR tube, thereby obviating the need to open the tube. The lid is pierced just enough to allow the extraction of the sample and avoid unnecessary exposure to outside contaminants. A first hollow member 901 adjacent to the piercing member 910 flows oil into the vessel which then displaces the droplets containing the amplified target nucleic acid. A second hollow member 902 collects the droplets as they rise and enter the second hollow member 902. The droplets then flow into a main channel 908 where in certain embodiments, an analysis module connected to the main channel analyzes the PCR products contained within the droplets as they pass through the channel 908.

Any analytical technique known in the art may be used to analyze the droplets. For example, the target nucleic acid could be analyzed for the presence of polymerase methods that occur during PCR reactions. Methods for conducting such analyses are described further in U.S. patent application Ser. No. 13/026,120. In addition, certain aspects include the detection of multiple targets with the same optical color, also described in U.S. patent application Ser. No. 13/026, 120. These methods are particularly useful in digital PCR where it is desirable to identify multiple different target molecules that may be present in the starting test fluid.

Further analytical techniques may include determining a number of droplets that contain only wild-type target, and determining a number of droplets that contain only a variant of the target. The variant may be indicative of cancer. The variant may be an allelic variant. The variant may also be a specific haplotype. Haplotypes refer to the presence of two or more variants on the same nucleic acid strand. Because each droplet contains only one template strand it is an ideal vessel for the determination of haplotypes. The detection of two or more variants in a single droplet that contains a single intact nucleic acid strand identifies the haplotype of the variants on that strand. The presence of two or more markers in the same droplet can be identified by such methods as the presence of dyes of multiple colors or the increase in the intensity of a single dye or a combination of both. Any method that allows the identification of multiple variants in a single droplet enables the determination of a samples haplotype.

In general, the methods and assemblies described above facilitate the collection and analysis of PCR reaction droplets associated with dPCR while mitigating contamination. Droplets can be generated with each droplet containing a single nucleic acid template and the necessary amplification reagents. The droplets can then be collected for amplification in a manner that reduces exposure of the droplets to outside contaminants, and after amplification is complete, the droplets can also be analyzed in a manner that reduces exposure of the droplets to outside contaminants. Accordingly, the provided methods and assemblies are especially amenable for use with dPCR.

Kits

As a matter of convenience, predetermined amounts of the reagents, compound libraries, and/or emulsions described herein and employed in the present invention can be optionally provided in a kit in packaged combination to facilitate the application of the various assays and methods described herein. Such kits also typically include instructions for carrying out the subject assay, and may optionally include the fluid receptacle, e.g., the cuvette, multiwell plate, microfluidic device, etc. in which the reaction is to be carried out.

Typically, reagents included within the kit are uniquely labeled emulsions containing tissues, cells, particles, proteins, antibodies, amino acids, nucleotides, small molecules, substrates, and/or pharmaceuticals. These reagents may be provided in pre-measured container (e.g., vials or ampoules) which are co-packaged in a single box, pouch or the like that is ready for use. The container holding the reagents can be configured so as to readily attach to the fluid receptacle of the device in which the reaction is to be carried out (e.g., the inlet module of the microfluidic device as described herein). In one embodiment, the kit can include an RNAi kit. In another embodiment, the kit can include a chemical synthesis kit. It will be appreciated by persons of ordinary skill in the art that these embodiments are merely illustrative and that other kits are also within the scope of the present invention.

Methods

The microfluidic device of the present invention can be utilized to conduct numerous chemical and biological assays, including but not limited to, creating emulsion libraries, flow cytometry, gene amplification, isothermal gene amplification, DNA sequencing, SNP analysis, drug screening, RNAi analysis, karyotyping, creating microbial strains with improved biomass conversion, moving cells using optical tweezer/cell trapping, transformation of cells by electroporation, μTAS, and DNA hybridization.

Definitions

The terms used in this specification generally have their ordinary meanings in the art, within the context of this invention and in the specific context where each term is used. Certain terms are discussed below, or elsewhere in the specification, to provide additional guidance to the practitioner in describing the devices and methods of the invention and how to make and use them. It will be appreciated that the same thing can typically be described in more than one way. Consequently, alternative language and synonyms may be used for any one or more of the terms discussed herein. Synonyms for certain terms are provided. However, a recital of one or more synonyms does not exclude the use of other synonyms, nor is any special significance to be placed upon whether or not a term is elaborated or discussed herein. All publications, patent applications, patents, and other references mentioned herein are incorporated by reference. In the case of conflict, the present specification, including definitions, will control. In addition, the materials, methods, and examples are illustrative only and are not intended to be limiting.

The invention is also described by means of particular examples. However, the use of such examples anywhere in the specification, including examples of any terms discussed herein, is illustrative only and in no way limits the scope and meaning of the invention or of any exemplified term. Likewise, the invention is not limited to any particular preferred embodiments described herein. Indeed, many modifications and variations of the invention will be apparent to those skilled in the art upon reading this specification and can be made without departing from its spirit and scope. The invention is therefore to be limited only by the terms of the appended claims along with the full scope of equivalents to which the claims are entitled.

As used herein, "about" or "approximately" shall generally mean within 20 percent, preferably within 10 percent, and more preferably within 5 percent of a given value or range.

The term "molecule" means any distinct or distinguishable structural unit of matter comprising one or more atoms, and includes for example polypeptides and polynucleotides.

The term "polymer" means any substance or compound that is composed of two or more building blocks ('mers') that are repetitively linked to each other. For example, a "dimer" is a compound in which two building blocks have been joined together.

The term "polynucleotide" as used herein refers to a polymeric molecule having a backbone that supports bases capable of hydrogen bonding to typical polynucleotides, where the polymer backbone presents the bases in a manner to permit such hydrogen bonding in a sequence specific fashion between the polymeric molecule and a typical polynucleotide (e.g., single-stranded DNA). Such bases are typically inosine, adenosine, guanosine, cytosine, uracil and thymidine. Polymeric molecules include double and single stranded RNA and DNA, and backbone modifications thereof, for example, methylphosphonate linkages.

Thus, a "polynucleotide" or "nucleotide sequence" is a series of nucleotide bases (also called "nucleotides") generally in DNA and RNA, and means any chain of two or more nucleotides. A nucleotide sequence typically carries genetic information, including the information used by cellular machinery to make proteins and enzymes. These terms include double or single stranded genomic and cDNA, RNA, any synthetic and genetically manipulated polynucleotide, and both sense and anti-sense polynucleotide (although only sense stands are being represented herein). This includes single- and double-stranded molecules, i.e., DNA-DNA, DNA-RNA and RNA-RNA hybrids, as well as "protein nucleic acids" (PNA) formed by conjugating bases to an amino acid backbone. This also includes nucleic acids containing modified bases, for example thio-uracil, thio-guanine and fluoro-uracil.

The polynucleotides herein may be flanked by natural regulatory sequences, or may be associated with heterologous sequences, including promoters, enhancers, response elements, signal sequences, polyadenylation sequences, introns, 5'- and 3'-non-coding regions, and the like. The nucleic acids may also be modified by many means known in the art. Non-limiting examples of such modifications include methylation, "caps", substitution of one or more of the naturally occurring nucleotides with an analog, and internucleotide modifications such as, for example, those with uncharged linkages (e.g., methyl phosphonates, phosphotriesters, phosphoroamidates, carbamates, etc.) and with charged linkages (e.g., phosphorothioates, phosphorodithioates, etc.). Polynucleotides may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. The polynucleotides may be derivatized by formation of a methyl or ethyl phosphotriester or an alkyl phosphoramidate linkage. Furthermore, the polynucleotides herein may also be modified with a label capable of providing a detectable signal, either directly or indirectly. Exemplary labels include radioisotopes, fluorescent molecules, biotin, and the like.

The term "dielectrophoretic force gradient" means a dielectrophoretic force is exerted on an object in an electric field provided that the object has a different dielectric constant than the surrounding media. This force can either pull the object into the region of larger field or push it out of the region of larger field. The force is attractive or repulsive depending respectively on whether the object or the surrounding media has the larger dielectric constant.

"DNA" (deoxyribonucleic acid) means any chain or sequence of the chemical building blocks adenine (A), guanine (G), cytosine (C) and thymine (T), called nucleotide bases, that are linked together on a deoxyribose sugar backbone. DNA can have one strand of nucleotide bases, or two complimentary strands which may form a double helix structure. "RNA" (ribonucleic acid) means any chain or sequence of the chemical building blocks adenine (A), guanine (G), cytosine (C) and uracil (U), called nucleotide bases, that are linked together on a ribose sugar backbone. RNA typically has one strand of nucleotide bases.

A "polypeptide" (one or more peptides) is a chain of chemical building blocks called amino acids that are linked together by chemical bonds called peptide bonds. A "protein" is a polypeptide produced by a living organism. A protein or polypeptide may be "native" or "wild-type", meaning that it occurs in nature; or it may be a "mutant", "variant" or "modified", meaning that it has been made, altered, derived, or is in some way different or changed from a native protein, or from another mutant.

An "enzyme" is a polypeptide molecule, usually a protein produced by a living organism, that catalyzes chemical reactions of other substances. The enzyme is not itself altered or destroyed upon completion of the reaction, and can therefore be used repeatedly to catalyze reactions. A "substrate" refers to any substance upon which an enzyme acts.

As used herein, "particles" means any substance that may be encapsulated within a droplet for analysis, reaction, sorting, or any operation according to the invention. Particles are not only objects such as microscopic beads (e.g., chromatographic and fluorescent beads), latex, glass, silica or paramagnetic beads, but also includes other encapsulating porous and/or biomaterials such as liposomes, vesicles and other emulsions. Beads ranging in size from 0.1 micron to 1 mm can be used in the devices and methods of the invention and are therefore encompassed with the term "particle" as used herein. The term particle also encompasses biological cells, as well as beads and other microscopic objects of similar size (e.g., from about 0.1 to 120 microns, and typically from about 1 to 50 microns) or smaller (e.g., from about 0.1 to 150 nm). The devices and methods of the invention are also directed to sorting and/or analyzing molecules of any kind, including polynucleotides, polypeptides and proteins (including enzymes) and their substrates and small molecules (organic or inorganic). Thus, the term particle further encompasses these materials.

The particles (including, e.g., cells and molecules) are sorted and/or analyzed by encapsulating the particles into individual droplets (e.g., droplets of aqueous solution in oil), and these droplets are then sorted, combined and/or analyzed in a microfabricated device. Accordingly, the term "droplet" generally includes anything that is or can be contained within a droplet.

A "small molecule" as used herein, is meant to refer to a composition that has a molecular weight of less than about 5 kD and most preferably less than about 4 kD. Small molecules can be, e.g., nucleic acids, peptides, polypeptides, peptidomimetics, carbohydrates, lipids or other organic or inorganic molecules. Libraries of chemical and/or biological mixtures, such as fungal, bacterial, or algal extracts, are known in the art.

As used herein, "cell" means any cell or cells, as well as viruses or any other particles having a microscopic size, e.g. a size that is similar to or smaller than that of a biological cell, and includes any prokaryotic or eukaryotic cell, e.g., bacteria, fungi, plant and animal cells. Cells are typically spherical, but can also be elongated, flattened, deformable and asymmetrical, i.e., non-spherical. The size or diameter of a cell typically ranges from about 0.1 to 120 microns, and typically is from about 1 to 50 microns. A cell may be living or dead. Since the microfabricated device of the invention is directed to sorting materials having a size similar to a biological cell (e.g. about 0.1 to 120 microns) or smaller (e.g., about 0.1 to 150 nm) any material having a size similar to or smaller than a biological cell can be characterized and sorted using the microfabricated device of the invention. Thus, the term cell shall further include microscopic beads (such as chromatographic and fluorescent beads), liposomes, emulsions, or any other encapsulating biomaterials and porous materials. Non-limiting examples include latex, glass, orparamagnetic beads; and vesicles such as emulsions and liposomes, and other porous materials such as silica beads. Beads ranging in size from 0.1 micron to 1 mm can also be used, for example in sorting a library of compounds produced by combinatorial chemistry. As used herein, a cell may be charged or uncharged. For example, charged beads may be used to facilitate flow or detection, or as a reporter. Biological cells, living or dead, may be charged for example by using a surfactant, such as SDS (sodium dodecyl sulfate). The term cell further encompasses "virions", whether or not virions are expressly mentioned.

A "virion", "virus particle" is the complete particle of a virus. Viruses typically comprise a nucleic acid core (comprising DNA or RNA) and, in certain viruses, a protein coat or "capsid". Certain viruses may have an outer protein covering called an "envelope". A virion may be either living (i.e., "viable") or dead (i.e., "non-viable"). A living or "viable" virus is one capable of infecting a living cell. Viruses are generally smaller than biological cells and typically range in size from about 20-25 nm diameter or less (parvoviridae, picornoviridae) to approximately 200-450 nm (poxviridae). However, some filamentous viruses may reach lengths of 2000 nm (closterviruses) and are therefore larger than some bacterial cells. Since the microfabricated device of the invention is particularly suited for sorting materials having a size similar to a virus (i.e., about 0.1 to 150 nm), any material having a size similar to a virion can be characterized and sorted using the microfabricated device of the invention. Non-limiting examples include latex, glass or paramagnetic beads; vesicles such as emulsions and liposomes; and other porous materials such as silica beads. Beads ranging in size from 0.1 to 150 nm can also be used, for example, in sorting a library of compounds produced by combinatorial chemistry. As used herein, a virion may be charged or uncharged. For example, charged beads may be used to facilitate flow or detection, or as a reporter. Biological viruses, whether viable or non-viable, may be charged, for example, by using a surfactant, such as SDS.

A "reporter" is any molecule, or a portion thereof, that is detectable, or measurable, for example, by optical detection. In addition, the reporter associates with a molecule, cell or virion or with a particular marker or characteristic of the molecule, cell or virion, or is itself detectable to permit identification of the molecule, cell or virion's, or the presence or absence of a characteristic of the molecule, cell or virion. In the case of molecules such as polynucleotides such characteristics include size, molecular weight, the presence or absence of particular constituents or moieties (such as particular nucleotide sequences or restrictions sites). In the case of cells, characteristics which may be marked by a reporter includes antibodies, proteins and sugar moieties, receptors, polynucleotides, and fragments thereof. The term "label" can be used interchangeably with "reporter". The reporter is typically a dye, fluorescent, ultraviolet, or chemiluminescent agent, chromophore, or radio-label, any of which may be detected with or without some kind of stimulatory event, e.g., fluoresce with or without a reagent. In one embodiment, the reporter is a protein that is optically detectable without a device, e.g. a laser, to stimulate the reporter, such as horseradish peroxidase (HRP). A protein reporter can be expressed in the cell that is to be detected, and such expression may be indicative of the presence of the protein or it can indicate the presence of another protein that may or may not be coexpressed with the reporter. A reporter may also include any substance on or in a cell that causes a detectable reaction, for example by acting as a starting material, reactant or a catalyst for a reaction which produces a detectable product. Cells may be sorted, for example, based on the presence of the substance, or on the ability of the cell to produce the detectable product when the reporter substance is provided.

A "marker" is a characteristic of a molecule, cell or virion that is detectable or is made detectable by a reporter, or which may be coexpressed with a reporter. For molecules, a marker can be particular constituents or moieties, such as restrictions sites or particular nucleic acid sequences in the case of polynucleotides. For cells and virions, characteristics may include a protein, including enzyme, receptor and ligand proteins, saccharides, polynucleotides, and combinations thereof, or any biological material associated with a cell or virion. The product of an enzymatic reaction may also be used as a marker. The marker may be directly or indirectly associated with the reporter or can itself be a reporter. Thus, a marker is generally a distinguishing feature of a molecule, cell or virion, and a reporter is generally an agent which directly or indirectly identifies or permits measurement of a marker. These terms may, however, be used interchangeably.

The invention is further described below, by way of the following examples. The examples also illustrate useful methodology for practicing the invention. These examples do not limit the claimed invention.

EXAMPLES

Example 1

The present invention provides methods for preparing a library of droplet emulsions, where each of the droplets is of the same, predetermined size (monodisperse). Further, present invention provides methods for deterministic lateral displacement for continuous particle separation, which can occur within droplets on a microfluidic device.

Particles in solution are usually separated according to size by exclusion or hydrodynamic chromatography. In the former, a sample mixture is injected at one end of a tube packed with porous beads and then washed through the tube. Particles smaller than the pore sizes enter the beads, which lengthen their migration path, and so they are on average eluted later than larger particles. Zones of particles of a given size broaden, however, because particles in each zone take many different paths, leading to different retention times. This multipath effect reduces the resolution of size-exclusion chromatography. In hydrodynamic chromatography, a sample mixture is driven through a capillary by hydrodynamic flow, which has a parabolic flow profile. Large particles cannot intercept the low-velocity fluid near the capillary wall, and thus on average move faster and become separated from small particles. Multipath effects also limit the resolution of hydrodynamic chromatography, because each migration path samples different velocities in the parabolic flow.

Recently, Huang et al. Science 304(5673):987-90, 2004 and Davis et al. Proc Natl Acad Sci USA. 103(40):14779-84, 2006 demonstrate a separation process that creates equivalent migration paths for each particle in a mixture, thereby eliminating multipath zone broadening. They describe a 'lateral displacement' means for separation of particles in solution based on particle size.

Lateral displacement means for sizing and separating droplets in solution (based on droplet size) can be utilized. The present invention relates to the generation of a microfluidic device consisting of raised pillars in both columns and rows that are designed for lateral diffusion. The pillars can be adjusted so as to be a means for separating droplets of similar sizes from a fluid containing various sized droplets.

In an example, a fluid containing oil, water and a surfactant is mixed so as to create a bulk emulsion. The bulk emulsion is injected into beginning of a microfluidic lateral diffusion device and various fractions are collected at the ending of the device at positions corresponding to specific sizes. Advantages to this lateral diffusion separation means would be the isolation of similarly-sized droplets off-line in a fast and facile manner. Bulk emulsions could be size-selected and then the resulting emulsions, if desired, combined to create sized libraries for re-introduction into a microfluidic device. In a further example, the lateral diffusion microfluidic devices could be rolled-up into a syringe or designed for parallel processing.

Recently, devices that exploit both techniques have been miniaturized with the use of microfabrication technology.

Microfabricated devices have also been designed that inherently rely on diffusion for separation. Particle mixtures are either repeatedly subject to spatially asymmetric potentials created by microelectrodes or driven through arrays of micrometer-scale asymmetric obstacles to exploit differences in diffusion lengths. In all of the devices discussed so far, particles in a given zone have many different migration paths, and diffusion is required for separation.

Figure 24A:
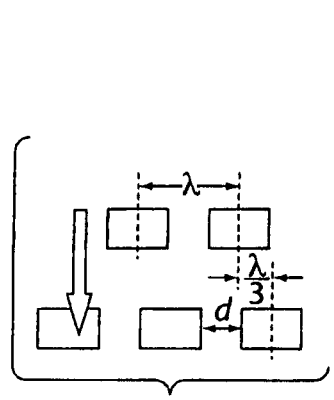
FIG. 24A shows geometric parameters defining the obstacle matrix.
Figure 24B:
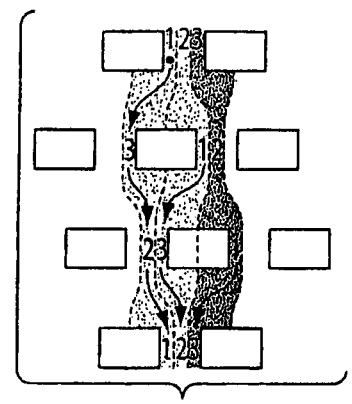
FIG. 24B shows three fluid streams.
Figure 24C:
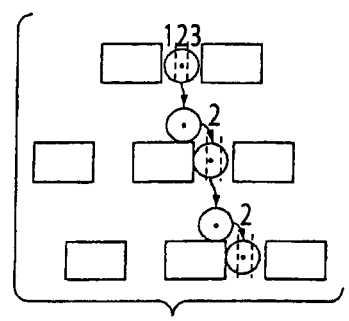
FIG. 24C shows a particle with a radius that is larger than lane 1 follows a streamline passing through the particle's center (black dot).

The present invention describes a separation process that creates equivalent migration paths for each particle in a mixture, thereby eliminating multipath zone broadening (FIGS. 24A-C). FIG. 24A Geometric parameters defining the obstacle matrix. A fluid flow is applied in the vertical direction (orange arrow). (FIG. 24B) Three fluid streams (red, yellow, and blue) in a gap do not mix as they flow through the matrix. Lane 1 at the first obstacle row becomes lane 3 at the second row, lane 3 becomes lane 2 at the third row, and so on. Small particles following streamlines will thus stay in the same lane. (FIG. 24C) A particle with a radius that is larger than lane 1 follows a streamline passing through the particle's center (black dot), moving toward lane 1. The particle is physically displaced as it enters the next gap. Black dotted lines mark the lanes.

The separation process uses laminar flow through a periodic array of micrometer-scale obstacles. Each row of obstacles is shifted horizontally with respect to the previous row by $\delta\lambda$, where $\lambda$ is the center-to-center distance between the obstacles (FIGS. 24A-C). For convenience, let $\delta\lambda/\lambda$ be ⅓. Fluid emerging from a gap between two obstacles will encounter an obstacle in the next row and will bifurcate as it moves around the obstacle. Let the flow diverted to the left of the obstacle be $\delta\varphi$, where $\varphi$ is the total fluid flux going through the gap. If the fluid is confined to move straight down through the array, $\delta$ must equal $\delta\lambda/\lambda$. Let us then consider the flow through a gap to be made up of three lanes, each of which by definition has a flux of $\varphi/3$. Because the Reynolds number is low (<10−3 in micrometer-scale environments) and flows are laminar, the streams in each lane do not cross or mix (FIG. 24B). Notably, as the lanes go through gaps, their positions relative to the gaps change. The lanes are represented in each gap by 1, 2, and 3, from left to right, respectively. Lane 1 becomes lane 3 in the next gap, lane 2 becomes lane 1, and lane 3 becomes lane 2 (FIGS. 24A-C). After three rows, the three lanes rejoin in their original configuration.

Particles that are smaller than the lane width will follow the streamlines. A particle starting in lane 1 will go through lane 3 (right lane with respect to the gap) in the second row, lane 2 (middle lane) in the third row, and back to lane 1 (left lane) in the fourth row (FIG. 24B). In fact, particles starting from any of the three lanes will go back to the original lane assignment after three rows, so that net migration is in the average flow direction. This motion is called the "zigzag mode." In practice, particles can diffuse into an adjacent lane. However, the microscopic path for all lanes is equivalent, unlike the multiple paths particles take when moving through a column of porous beads. In contrast to the smaller particles, a particle with a radius larger than the width of lane 1 at a gap will behave differently in the array. This is because the center of the particle cannot "fit" into lane 1 in a gap. As such a particle from lane 2 in one gap moves into the subsequent gap, expecting to move through the gap in lane 1, the particle will be "bumped" and its center will thus be displaced into lane 2 (FIG. 24C). The particle will then flow with the fluid in lane 2. This process is repeated every time a large particle approaches a row of obstacles, so that the particle remains in lane 2 as it moves down through the array. This transport pattern is called the "displacement mode." This is also applicable to electrophoresis by considering ion flows instead of fluid flows.

Figure 25:
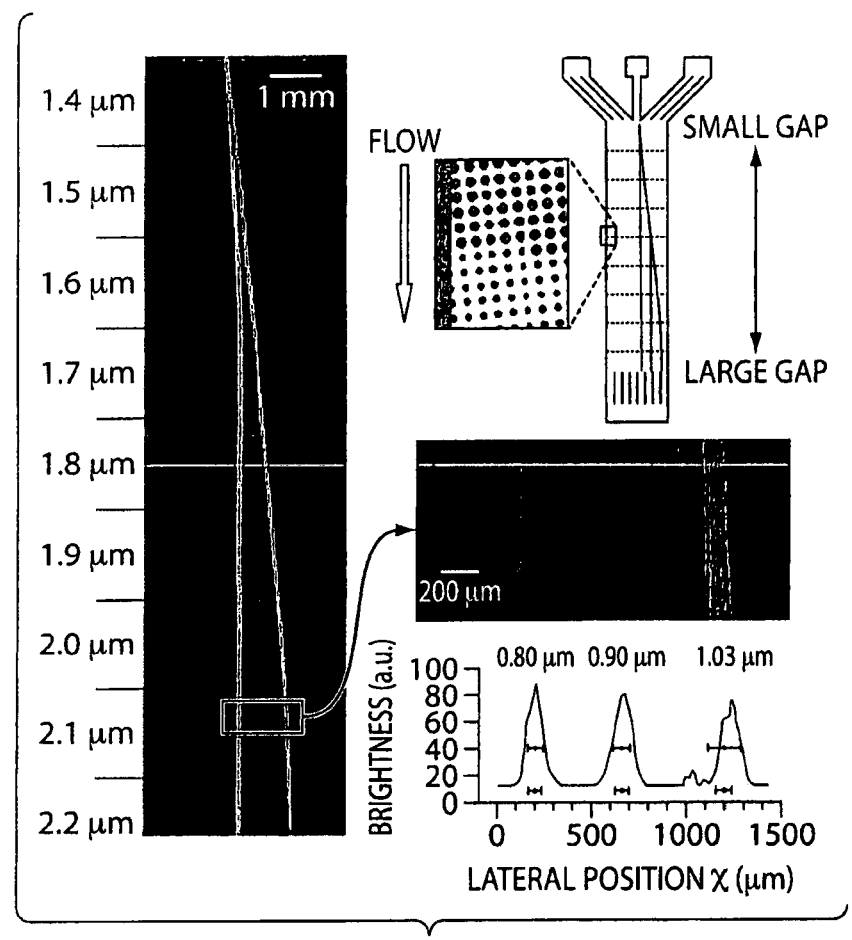
FIG. 25 shows high-resolution separation of fluorescent microspheres with diameters of 0.80 um (green), 0.90 um (red), and 1.03 um (yellow), with a matrix of varying gap size.

FIG. 25 shows High-resolution separation of fluorescent microspheres with diameters of 0.80 um (green), 0.90 um (red), and 1.03 um (yellow), with a matrix of varying gap size. Whereas the shift in registry and the lattice constants of the matrix remain the same, the obstacle diameters are changed to create gaps, d, of different sizes, which are labeled on the left side of the fluorescent image. The red bars on the fluorescence profile represent the width of the peaks (SD), and the black bars label the 1% inhomogeneity in the bead population. a.u., arbitrary units.

Figure 26:
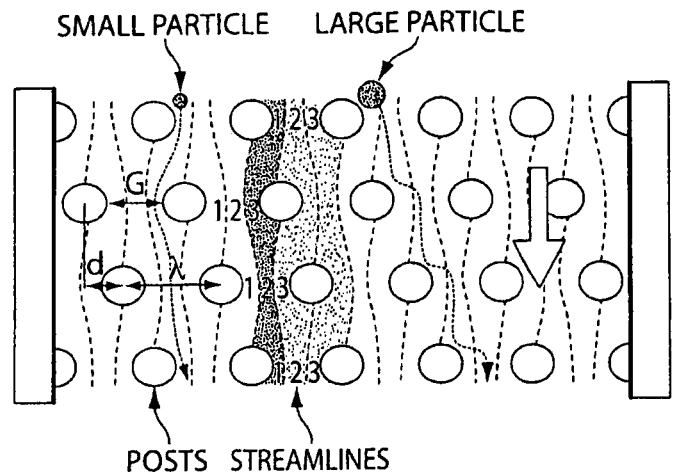
FIG. 26 is a schematic illustrating the separation by deterministic lateral displacement in an array of microposts, with an example row shift fraction of one-third.

FIG. 26 is a schematic illustrating the separation by deterministic lateral displacement in an array of microposts, with an example row shift fraction of one-third. This shift creates three equal flux streamlines. The dashed lines are the boundaries between the streamlines, which are assigned an index in the gaps between the posts. Paths of particles both smaller and larger than the critical threshold are depicted with green and red dotted lines respectively. Small particles stay within a flow stream and large particles are displaced at each obstacle. G is the clear spacing between the gap, is the center-to-center post separation, and d is the relative shift of the post centers in adjacent rows.

These described methods allow for the quick and efficient formation of uniformed sized droplet emulsion libraries for further use on a microfluidic device of the present invention.

Example 2

The present invention provides methods for performing polymerase chain reaction (PCR). PCR can be performed on a drop-by-drop basis in a microfluidic device according to the present invention. A monolithic chip can be provided wherein the heating and cooling lines are built into the chip and a sorting means is provided. Advantages of performing PCR in droplets on such a chip are that the chip is disposable and the reaction can be repeated without cleaning the device between reactions. Furthermore, the chip provides a convenient way of getting all the components to perform PCR in the droplets in the right concentration. Additionally, the PCR is more efficient because the heat transfer is more efficient due to the small volume. This provides for shorter incubation/residence times. Droplets containing the nucleic acids, all PCR primers, and, if present, beads are generated one at a time at rates between 100 and 20,000 droplets per second. The droplets can then be sent through a serpentine path between heating and cooling lines to amplify the genetic material inside the droplets. Upon exiting the device the droplets may be sent for further on-chip or off-chip processing, directed into another chip, or the emulsion may be broken to release the PCR product. If present, beads may be harvested by passing the emulsion through a filtration device, sedimentation, or centrifugation.

The width and depth of the channel can be adjusted to set the residence time at each temperature, which can be controlled to anywhere between less than a second and minutes. At a typical rate of 1000 drops per second, 1 million strands of DNA can be amplified in approximately 20 minutes on one device. A typical flow rate of 250 μL/hour would correspond to 1000 drops of 50 microns in diameter being generated every second. Flow rates and droplet sizes can be adjusted as needed by controlling the nozzle geometry.

The present invention also provides methods for performing dideoxynucleotide sequencing reactions on a microfluidic device. Chain terminator sequencing (Sanger sequencing) is well known to those of ordinary skill in the art. DNA template preparation, cycling sequencing and preparing extension products for electrophoresis are related techniques and also well known to those of skill in the art. Applied Biosystems' "Automated DNA Sequencing: Chemistry Guide" 2000 is an excellent resource covering these techniques and is incorporated herein by reference in its entirety.

One method is to sequencing PCR templates which can include single amplification PCR or nested and semi-nested PCR strategies. In the simplest PCR sequencing case, the target DNA is amplified with a single set of primers and then sequenced using the same primers. For many samples, this works well. For the samples that do not work well with this method, optimization of the PCR amplification may be required. Optimizing the PCR minimizes the presence of non-specific product bands and ensures adequate yield. A single PCR amplification is also compatible with the use of a sequencing primer that binds internally (semi-nested or nested) to one or both of the PCR primers. This can be helpful if primer-dimer (primer oligomerization) artifacts are a problem.

If difficulty with more complex samples, such as bacterial genomic DNA, is encountered a nested or semi-nested PCR can be used. These techniques are useful when the target is present in small quantity. They offer more specificity, which provides superior sequencing data with reduced background signal. Both nested and semi-nested PCR require two amplifications. The first amplification is identical for nested and semi-nested, but the second amplification differs as described below. Amplify with one set of PCR primers, which converts a complex sample (such as bacterial genomic DNA) into a non-complex sample consisting of the first PCR product and some side products. Nested PCR: Amplify 1% or less of the first PCR reaction product using a second set of PCR primers that hybridize at positions internal to the first set. Semi-nested PCR: Only one primer of the second set of PCR primers is internal. The other primer is one of the original PCR primers.

A PCR primer can be synthesized with a universal sequencing primer binding site added to the 5' end (e.g., see Appendix E in Applied Biosystems' "Automated DNA Sequencing: Chemistry Guide" for universal primer sequences). This allows any PCR product to be sequenced with universal primers. Universal-tailed PCR primers enable the use of commercially available dye-labeled sequencing primers. This technique is also useful with dye terminator chemistries, because universal sequencing primers have good annealing characteristics. However, the longer PCR primers add to the overall cost of the reactions. Using universal-tailed primers sometimes results in primer oligomerization. As these products have priming sites present, they can result in noisy data for the first 20-100 bases. Redesigning the PCR primer, optimizing the PCR amplification further, and employing Hot Start methods can help overcome this situation.

After PCR amplification, the resulting PCR product is in solution along with PCR primers, dNTPs, enzyme, and buffer components. The method used to prepare the PCR product for sequencing depends on the amounts of these components that are carried over and on the chemistry used for sequencing. Excess PCR primers carried over from the amplification reaction compete with the sequencing primer for binding sites and reagents in the sequencing reaction. This carryover of PCR primers presents more of a problem in dye terminator chemistries because the dye label is incorporated into the extension product after the primer anneals to the template. If more than one primer is present, multiple dye-labeled sequence ladders are generated, resulting in noisy data. Excess dNTPs from the amplification reaction can affect the balance of the sequencing reaction, resulting in decreased termination in shorter extension fragments. Nonspecific PCR products include primer-dimer artifacts and secondary PCR products. The presence of any significant quantity of either in a PCR product can result in poor quality sequencing data. Nonspecific PCR products behave as templates in the sequencing reaction and produce extension products, which results in noisy data. These products often can be visualized on an agarose gel before sequencing. If they are present, the PCR amplification should be optimized and repeated before sequencing. Use of a nested or semi-nested sequencing primer can also allow good sequence data to be obtained. Alternatively, the PCR product of interest can be purified by agarose gel electrophoresis.

There are several ways to minimize contaminants in a PCR amplification: PCR optimization (Innis and Gelfand, 1990): (1) Amount of starting DNA; (2) Careful primer design; (3) Primer concentration, (4) Enzyme concentration, (5) Magnesium ion (Mg2+) concentration, (6) Nucleotide concentration; (7) Buffer composition; (8) Number of cycles; (9) pH; (10) Manual Hot Start method; (11) AmpliTa Gold® DNA Polymerase as an automatic Hot Start and/or (12) Limiting dNTPs and primers. All of these methods increase the specificity of the PCR amplification and decrease the amount of contaminants that can interfere with a sequencing reaction.

There are several methods for purifying PCR products: (1) Column purification; (2) Ethanol precipitation; and/or (3) Gel purification.

An alternative to one of the more stringent purification methods listed above is treatment of PCR products with shrimp alkaline phosphatase (SAP) and exonuclease I (Exo I) before sequencing. The SAP/Exo I procedure degrades nucleotides and single-stranded DNA (primers) remaining after PCR (Werle et al., 1994). This procedure is particularly useful in cases where limiting concentrations of primers and nucleotides cannot be used for direct PCR sequencing.

Figure 27:
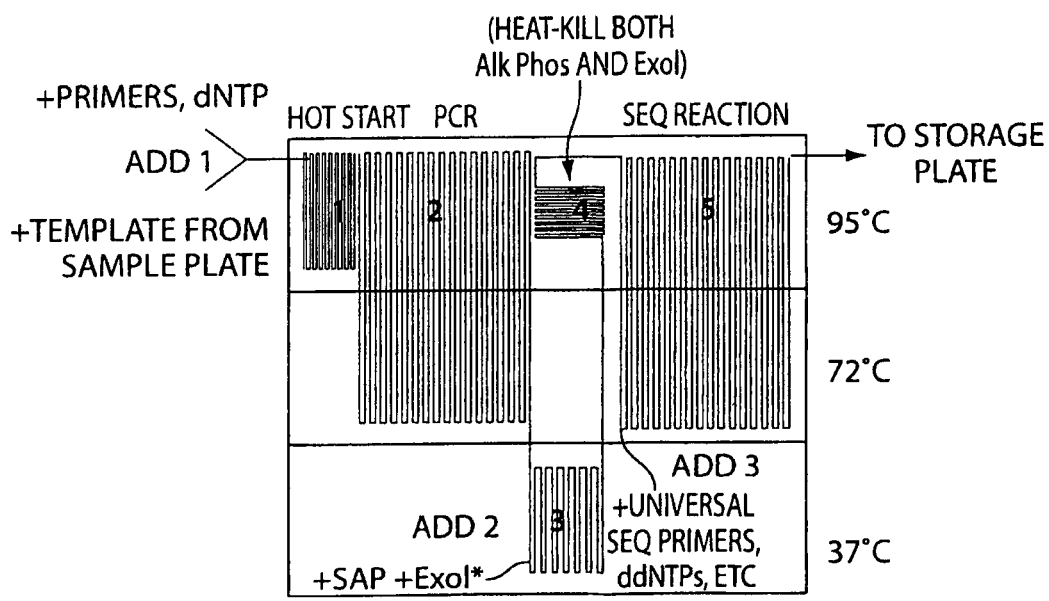
FIG. 27 shows a dideoxynucleotide sequencing on a microfabricated chip. Shown is one embodiment for a DNA sequencing chip design. Template DNA and primers are combined at step 'add 1' and the reaction is incubated at 95° C. for a hot start (position 1). The reaction then cycles 20-30 times (position 2) before the addition of SAP and ExoI at 'add 2.' The reaction is incubated at 37° C. for a pre-defined time-period and then the SAP and ExoI enzymes are inactivated at 95° C. (position '4'). The SAP/ExoI procedure degrades nucleotides and single-stranded DNA (primers) remaining after PCR. The universal sequencing primers, ddNTPs and buffers are added at 'add 3,' and the PCR sequencing reaction is allowed to proceed at position '5.' The final reaction product is collected and can be stored off-chip.
Figure 28A:
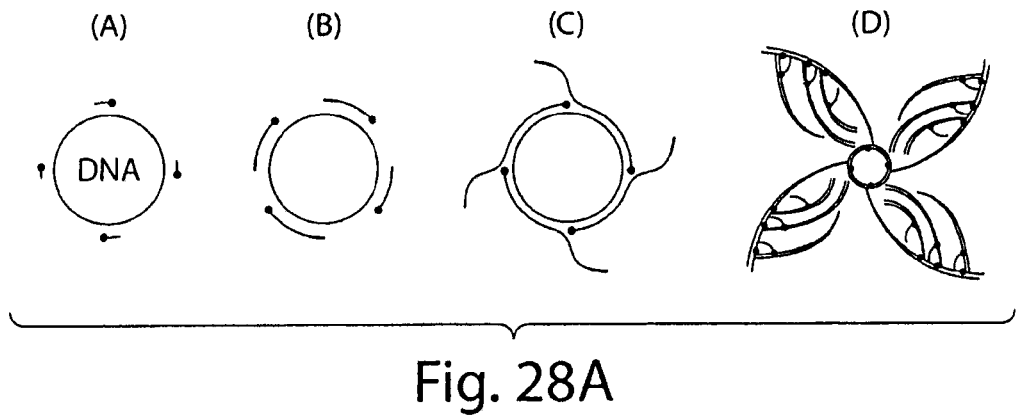
FIG. 28A shows a schematic of the TempliPhi amplification process using rolling circle amplification.
Figure 28B:
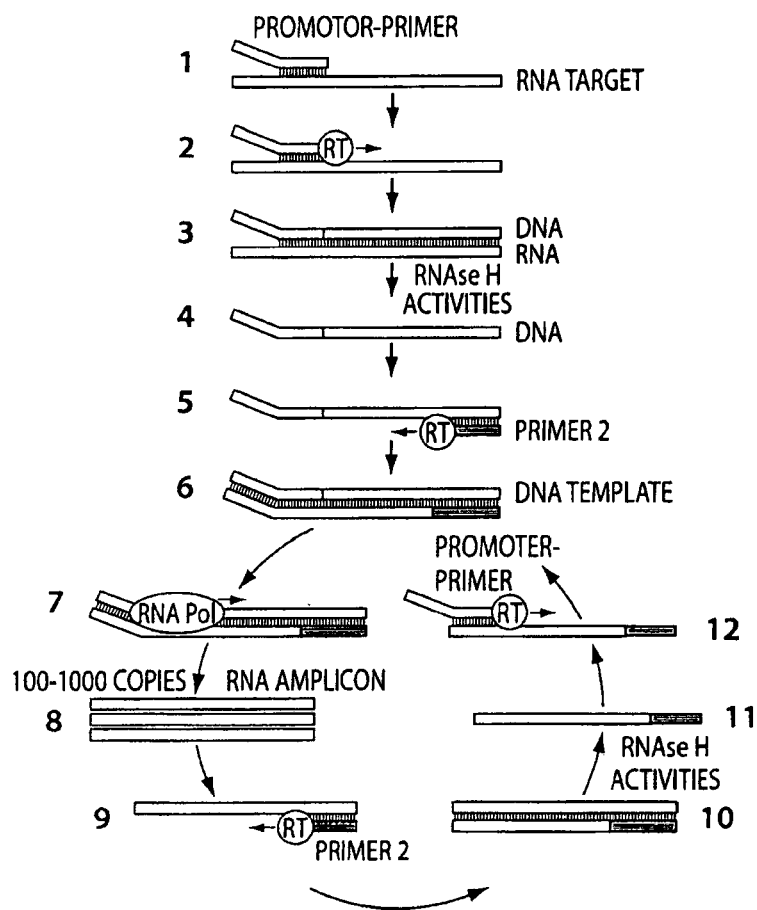
FIG. 28B illustrates a transcription mediated reaction.
Figure 28C:
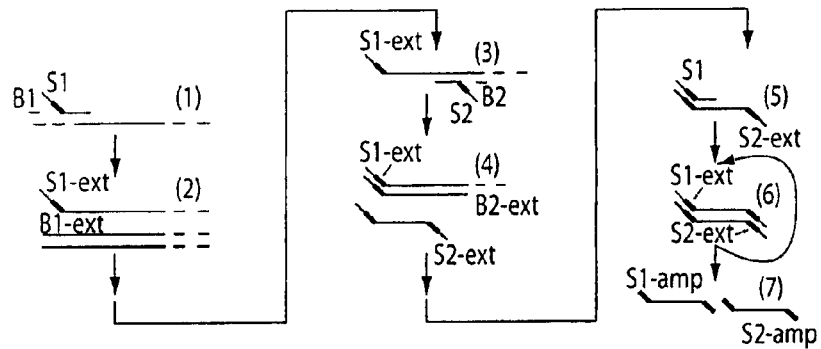
FIG. 28C illustrates strand-displacement amplification.
Figure 28D:
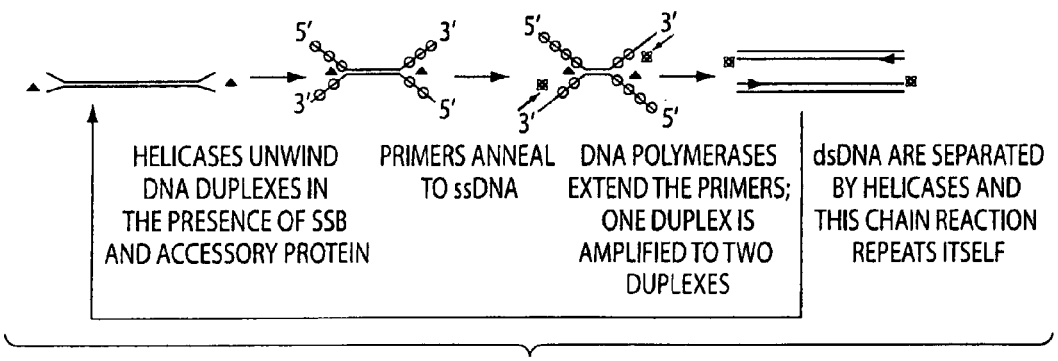
FIG. 28D shows a schematic diagram of helicase-dependent amplification.

FIG. 27 shows one embodiment for a DNA sequencing chip design. Template DNA and primers are combined at step 'add 1' and the reaction is incubated at 95° C. for a hot start (position 1). The reaction then cycles 20-30 times (position 2) before the addition of SAP and ExoI at 'add 2.' The reaction is incubated at 37° C. for a pre-defined time-period and then the SAP and ExoI enzymes are inactivated at 95° C. (position '4'). The SAP/ExoI procedure degrades nucleotides and single-stranded DNA (primers) remaining after PCR. The universal sequencing primers, ddNTPs and buffers are added at 'add 3,' and the PCR sequencing reaction is allowed to proceed at position '5' The final reaction product is collected and can be stored off-chip.

Step Action

1. For each sample, combine the following:
SAP (1 Unit/µL), 2 µL
Exo I (10 Units/µL), 0.2 µL
Deionized water, 6.0 µL
Note In general this procedure works well using 0.5 units of each enzyme per microliter of PCR products used. The procedure seems to work equally well with or without the use of SAP buffer, so this has been excluded in this protocol.
2. Add 4.0 µL of PCR product to the above mix.
3. Incubate at 37° C. for 1 hour.
4. Incubate at 72° C. for 15 minutes to inactivate the enzymes.

The recommended DNA quantities for sequencing reactions are shown in Table 3-1 below.

TABLE 3-1

Recommended Ranges of DNA Template Quantity for Each Chemistry

| Template | Cycle Sequencing Chemistry | | | | |
|---|---|---|---|---|---|
| | Rhodamine Dye Terminator | dRhodamine Terminator | BigDye Terminator | Fluorescien/Rhodamine Dye Primer | BigDye Primer |
| PCR product: | | | | | |
| 100-200 bp | 1-3 ng | 1-3 ng | 1-3 ng | 2-5 ng | 2-5 ng |
| 200-500 bp | 3-10 ng | 3-10 ng | 3-10 ng | 5-10 ng | 5-10 ng |
| 500-1000 bp | 5-20 ng | 5-20 ng | 5-20 ng | 10-20 ng | 10-20 ng |
| 1000-2000 bp | 10-40 ng | 10-40 ng | 10-40 ng | 20-50 ng | 20-50 ng |
| >2000 bp | 40-100 ng | 40-100 ng | 40-100 ng | 50-150 ng | 50-150 ng |
| single-stranded | 100-250 ng | 50-100 ng | 50-100 ng | 150-300 ng | 150-400 ng |
| double-stranded | 200-500 ng | 200-500 ng | 200-500 ng | 300-600 ng | 200-800 ng |
| cosmid, BAC | 0.5-2.0 µg | not recommended | 0.5-1.0 µg | 0.5-2.0 µg | 0.5-1.0 µg |
| bacterial genomic DNA | not recommended | | 2-3 µg | not recommended | |

PCR protocols that limit amounts of primers and dNTPs allow the product of the reaction to be used for sequencing with no purification. This is usually carried out by setting up the PCR amplification with 5-10 pmol of primers and 20-40 µM dNTPs, so that most of the primers and dNTPs are exhausted during amplification. If the yield of the desired PCR product is high and the product is specific, i.e., it produces a single band when analyzed by agarose gel electrophoresis, the sample can be diluted before sequencing and will give good results. The dilution ratio depends on the concentration of your PCR product and needs to be determined empirically (start with 1:2 and 1:10 dilutions with deionized water). When you limit concentrations of primers and dNTPs and dilute the PCR products, the PCR parameters have to be robust. Direct PCR sequencing is most useful in applications where the same target is being amplified and sequenced repeatedly and PCR conditions have been optimized. Direct PCR sequencing can be done with dye primer chemistries. With dye terminator chemistries, it is much more critical that the PCR primers be consumed. Excess PCR primers will be extended and labeled by the cycle sequencing reaction, resulting in noisy data. Direct PCR sequencing does not work for XL PCR because limiting amounts of primers and dNTPs cannot be used. The PCR product should be purified or the excess primers and nucleotides should be degraded by SAP/Exo I treatment.

Example 3

The present invention provides methods for performing isothermal-type amplification methods on a microfluidic device. Isothermal amplification is an alternative to the standard PCR techniques described herein. Isothermal amplification is used to reduce the relative amount of background DNA in a sample. Primers are generally used in a constant temperature means of amplification. Isothermal amplification is applicable for SNP detection. Once the DNA is amplified by isothermal amplification there are several well-known means for detecting which nucleotide polymorphism is present. These include, but are not limited to; allele specific primer extension, oligonucleotide ligation assay, mini-sequencing, fluorescence polarization, etc. Isothermal amplification is also applicable for DNA sequencing preparation. The isothermally-amplified DNA can be attached to a solid phase within a droplet or placed within a parking space on chip. The beads or parking spaces can be accessed and the amplified DNA used for a DNA sequencing reaction. Further, isothermal amplification is applicable for gene expression analysis. Isothermal amplification can be used to monitor gene expression by the measurement of the amount of cDNA produced in a quantitative fashion. Many methods for isothermal amplification are known in the art, including but not limited to the following examples.

Rolling circle amplification (RCA). A DNA polymerase extends a primer on a circular template, generating tandemly linked copies of the complementary sequence of the template (Fire & Xu, 1995). The TempliPhi amplification process using rolling circle amplification is known in the art. In the process, random hexamer primers anneal to the circular template DNA at multiple sites. Phi29 DNA polymerase extends each of these primers. When the DNA polymerase reaches a downstream-extended primer, strand displacement synthesis occurs. The displaced strand is rendered single-stranded and available to be primed by more hexamer primer. The process continues, resulting in exponential, isothermal amplification.

Transcription mediated amplification (TMA). An RNA polymerase is used to make RNA from a promoter engineered in the primer region, a reverse transcriptase to produce complementary DNA from the RNA templates and RNase H to remove the RNA from cDNA (Guatelli et al, 1990).

Strand-displacement amplification (SDA). A restriction endonuclease is used to nick the unmodified strand of its target DNA and the action of an exonuclease-deficient DNA polymerase to extend the 30 end at the nick and displace the downstream DNA strand (Walker et al, 1992). Strand-displacement amplification is known in the art.

Helicase-dependent amplification (HDA). A DNA helicase is used to generate single-stranded templates for primer hybridization and subsequent primer extension by a DNA polymerase. Schematic diagram of HAD is shown in FIGS.

Figure 29A:
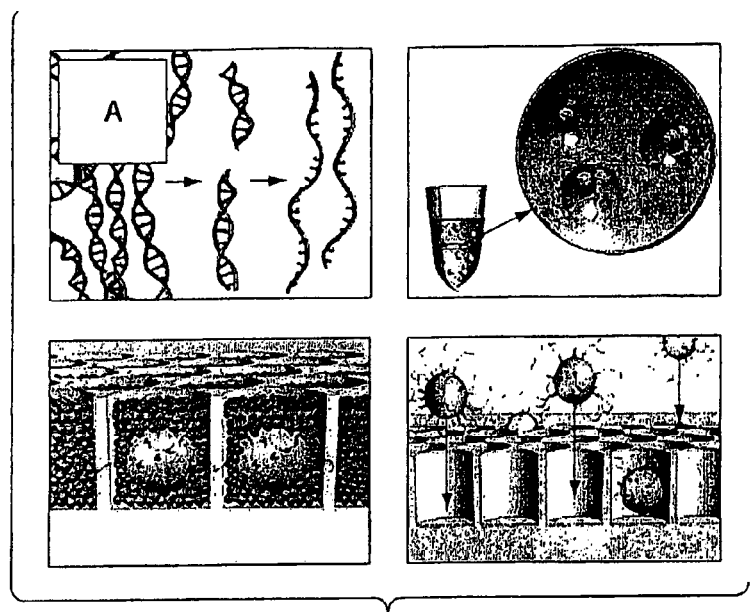
FIGS. 29A-D illustrate emulsion-based sample preparation, sample preparation and DNA sequencing. Random libraries of DNA fragments are generated by shearing an entire genome and isolating single DNA molecules by limiting dilution.
Figure 29B:
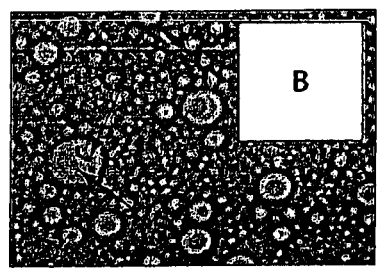

28A-D. Two complementary DNA strands are shown as two lines: the thick one is the top strand and the thin one is the bottom strand. 1: A helicase (black triangle) separates the two complementary DNA strands, which are bound by SSB (grey circles). 2: Primers (lines with arrow heads) hybridize to the target region on the ssDNA template. 3: A DNA polymerase (squares with mosaic patterns) extends the primers hybridized on the template DNA. 4: Amplified products enter the next round of amplification. One example is emulsion-based sample preparation. Random libraries of DNA fragments are generated by shearing an entire genome and isolating single DNA molecules by limiting dilution. See, FIGS. 29A-D. Specifically, sequencing reactions such as those performed by Solexa, 454 Life Sciences and others involve randomly fragmenting the entire genome, adding specialized common adapters to the fragments, capturing the individual fragments on their own beads and, within the droplets of an emulsion, clonally amplifying the individual fragment (FIGS. 29a, 29b). Unlike in current sequencing technology, their approach does not require subcloning or the handling of individual clones; the templates are handled in bulk within the emulsions. Typically, about 30% of the beads will have DNA, producing 450,000 template-carrying beads per emulsion reaction.

Figure 29C:
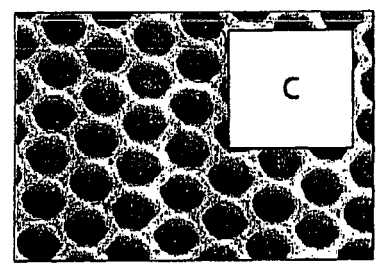
Figure 29D:
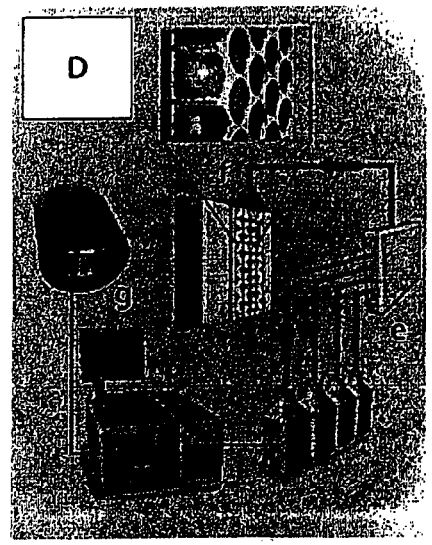

Sample preparation and DNA sequencing is shown in FIGS. 29A-D. FIG. 29A, Genomic DNA is isolated, fragmented, ligated to adapters and separated into single strands (top left). Fragments are bound to beads under conditions that favor one fragment per bead, the beads are captured in the droplets of a PCR-reaction-mixture-in-oil emulsion and PCR amplification occurs within each droplet, resulting in beads each carrying ten million copies of a unique DNA template (top, second from the left). The emulsion is broken, the DNA strands are denatured, and beads carrying single-stranded DNA clones are deposited into wells of a fiber-optic slide (bottom left). Smaller beads carrying immobilized enzymes required for pyrophosphate sequencing are deposited into each well (bottom, second from the left). FIG. 29B, Microscope photograph of emulsion showing droplets containing a bead and empty droplets. The thin arrow points to a 28-mm bead; the thick arrow points to an approximately 100-mm droplet. FIG. 29C, Scanning electron micrograph of a portion of a fiber-optic slide, showing fiber-optic cladding and wells before bead deposition. FIG. 29D, The sequencing instrument consists of the following major subsystems: a fluidic assembly, a flow chamber that includes the well-containing fiber-optic slide, a CCD camera-based imaging assembly, and a computer that provides the necessary user interface and instrument control.

Another example is sequencing in fabricated picoliter-sized reaction vessels. One method uses sequencing by synthesis simultaneously in open wells of a fiber-optic slide using a modified pyrosequencing protocol that is designed to take advantage of the small scale of the wells. The fiber optic slides are manufactured by slicing of a fiber-optic block that is obtained by repeated drawing and fusing of optic fibers. At each iteration, the diameters of the individual fibers decrease as they are hexagonally packed into bundles of increasing cross-sectional sizes. Each fiber-optic core is 44 µm in diameter and surrounded by 2-3 µm of cladding; etching of each core creates reaction wells approximately 55 µm in depth with a centre-to-centre distance of 50 µm (FIG. 29c), resulting in a calculated well size of 75 pl and a well density of 480 wells per square mm. The slide, containing approximately 1.6 million wells, is loaded with beads and mounted in a flow chamber designed to create a 300-µm high channel, above the well openings, through which the sequencing reagents flow (FIG. 29d). The unetched base of the slide is in optical contact with a second fiber optic imaging bundle bonded to a charge-coupled device (CCD) sensor, allowing the capture of emitted photons from the bottom of each individual well (FIG. 29d). A three-bead system has been developed and the components optimized to achieve high efficiency on solid support. The combination of picoliter-sized wells, enzyme loading uniformity allowed by the small beads and enhanced solid support chemistry enabled users to develop a method that extends the useful read length of sequencing-by-synthesis to 100 bases.

In the flow chamber cyclically delivered reagents flow perpendicularly to the wells. This configuration allows simultaneous extension reactions on template-carrying beads within the open wells and relies on convective and diffusive transport to control the addition or removal of reagents and by-products. The timescale for diffusion into and out of the wells is on the order of 10 s in the current configuration and is dependent on well depth and flow channel height. The timescales for the signal-generating enzymatic reactions are on the order of 0.02-1.5 s. The current reaction is dominated by mass transport effects, and improvements based on faster delivery of reagents are possible. Well depth was selected on the basis of a number of competing requirements: (1) wells need to be deep enough for the DNA-carrying beads to remain in the wells in the presence of convective transport past the wells; (2) they must be sufficiently deep to provide adequate isolation against diffusion of by-products from a well in which incorporation is taking place to a well where no incorporation is occurring; and (3) they must be shallow enough to allow rapid diffusion of nucleotides into the wells and rapid washing out of remaining nucleotides at the end of each flow cycle to enable high sequencing throughput and reduced reagent use. After the flow of each nucleotide, a wash containing a pyrase is used to ensure that nucleotides do not remain in any well before the next nucleotide being introduced.

Another example is base calling of individual reads. Nucleotide incorporation is detected by the associated release of inorganic pyrophosphate and the generation of photons. Wells containing template-carrying beads are identified by detecting a known four-nucleotide 'key' sequence at the beginning of the read. Raw signals are background-subtracted, normalized and corrected. The normalized signal intensity at each nucleotide flow, for a particular well, indicates the number of nucleotides, if any, that were incorporated. This linearity in signal is preserved to at least homopolymers of length eight. In sequencing by synthesis a very small number of templates on each bead lose synchronism (that is, either get ahead of, or fall behind, all other templates in sequence). The effect is primarily due to leftover nucleotides in a well (creating 'carry forward') or to incomplete extension. Typically, a carry forward rate of 1-2% and an incomplete extension rate of 0.1-0.3% is seen. Correction of these shifts is essential because the loss of synchronism is a cumulative effect that degrades the quality of sequencing at longer read lengths.

Methods have demonstrated the simultaneous acquisition of hundreds of thousands of sequence reads, 80-120 bases long, at 96% average accuracy in a single run of the instrument using a newly developed in vitro sample preparation methodology and sequencing technology. With Phred 20 as a cutoff, they are able to show that their instrument is able to produce over 47 million bases from test fragments and 25 million bases from genomic libraries. Recent work on the sequencing chemistry and algorithms that correct for crosstalk between wells suggests that the signal distributions will narrow, with an attendant reduction in errors and increase in read lengths. In preliminary experiments with genomic libraries that also include improvements in the emulsion protocol, one is able to achieve, using 84 cycles, read lengths of 200 bases with accuracies similar to those demonstrated here for 100 bases. On occasion, at 168 cycles, individual reads that are 100% accurate over greater than 400 bases have been generated.

Isothermal amplification reactions, as described above, have shown great promise generating high yields with great fidelity. However, an associated drawback arises from the tendency of the polymerase to generate spurious, non-template amplification products when reactions are conducted in the absence of template DNA. Additionally, our application utilizes high microfluidic throughput in conjunction with limiting DNA template dilutions to amplify single template molecules. As a result, the number of empty reaction droplets increases considerably, comprising 90% or more of the total droplet population following Poisson distributions. Non-template amplification (hereafter NTA) in even a small fraction of the total droplets can confound amplification detection strategies based on laser interrogation of intercalating dyes, thus this issue must be resolved. To address this problem in the art, the present invention provides the use of mixed modified and standard hexamer primers in microfluidic reactions to retard NTA while allowing template-based amplification to proceed.

Previous work has attempted to reduce NTA through incorporation of nitroindole bases (Loakes and Brown 1994; Loakes, Hill et al. 1997) in the random primers (Lage, Leamon et al. 2003) or reducing reaction volumes to 600 nL (Hutchison, Smith et al. 2005). Unfortunately, modified nitroindole primers have proven difficult to replicate, and often have the effect of significantly reducing the overall rate and yield of the amplifications in which they are incorporated. Low volume reactions conducted in multiplate wells have encountered difficulties stemming from dispensation of low volumes, and associated issues of sample evaporation, well to well contamination, etc.

The modified primers of the present invention containing nitroindoles and C3 non-replicable elements were studied in an effort to reduce NTA both in bulk and microfluidic reactions. Both nitroindoles and C3 non-replicable elements were found to be effective in reducing NTA, with primers containing two 5' nitroindoles most effective in NTA suppression. However, increased NTA suppression was tightly linked with reduced yield in template amplification reactions. Amplifications using a ratio of nitroindole to random hexamer primers generated a range of both template and non-template amplification yields, with a 15:85 ratio of nitroindole to random hexamers generating template yields commensurate with random hexamers primers alone, but generating little if any spurious product in the absence of template.

Example 4

The PCR and isothermal amplifications described herein can be very useful in performing single nucleotide polymorphism analysis. A Single Nucleotide Polymorphism, or SNP, is a small genetic change, or variation, that can occur within a person's DNA sequence. The genetic code is specified by the four nucleotide "letters" A (adenine), C (cytosine), T (thymine), and G (guanine). SNP variation occurs when a single nucleotide, such as an A, replaces one of the other three nucleotide letters—C, G, or T.

An example of a SNP is the alteration of the DNA segment AAGGTTA to ATGGTTA, where the second "A" in the first snippet is replaced with a "T". On average, SNPs occur in the human population more than 0.1 percent of the time. Because only about 3 to 5 percent of a person's DNA sequence codes for the production of proteins, most SNPs are found outside of "coding sequences". SNPs found within a coding sequence are of particular interest to researchers because they are more likely to alter the biological function of a protein. Because of the recent advances in technology, coupled with the unique ability of these genetic variations to facilitate gene identification, there has been a recent flurry of SNP discovery and detection.

Although many SNPs do not produce physical changes in people, scientists believe that other SNPs may predispose people to disease and even influence their response to drug regimens. Currently, there is no simple way to determine how a patient will respond to a particular medication. A treatment proven effective in one patient may be ineffective in others. Worse yet, some patients may experience an adverse immunologic reaction to a particular drug. Today, pharmaceutical companies are limited to developing agents to which the "average" patient will respond. As a result, many drugs that might benefit a small number of patients never make it to market.

In the future, the most appropriate drug for an individual could be determined in advance of treatment by analyzing a patient's SNP profile. The ability to target a drug to those individuals most likely to benefit, referred to as "personalized medicine", would allow pharmaceutical companies to bring many more drugs to market and allow doctors to prescribe individualized therapies specific to a patient's needs.

Finding single nucleotide changes in the human genome seems like a daunting prospect, but over the last 20 years, biomedical researchers have developed a number of techniques that make it possible to do just that. Each technique uses a different method to compare selected regions of a DNA sequence obtained from multiple individuals who share a common trait. In each test, the result shows a physical difference in the DNA samples only when a SNP is detected in one individual and not in the other. Currently, existing SNPs are most easily studied using microarrays. Microarrays allow the simultaneous testing of up to hundreds of thousands of separate SNPs and are quickly screened by computer.

The race among pharmaceutical companies today is to apply new system genomics approach to identify novel targets and validate these targets in the most efficient fashion. SNP research will provide fundamental understanding of many polygenic diseases, thus providing new therapeutic targets. As groups have performed genome-wide scans and other large studies that require the genotyping of thousands of SNPs and samples, a need for high-throughput SNP genotyping has become essential.

The microfluidic device of the present invention is capable of performing at least 10,000 SNP analysis per second, such that a full genome scan (i.e., 100K SNPs) with 10× overrepresentation can be performed in less than an hour. The speed and efficiency permitted using the devices and methods of the present invention will significantly lower the associated costs and reagent consumption for performing SNP analysis.

Example 5

The PCR and isothermal amplifications described herein can be very useful in providing necessary sample preparation processes for commercial available DNA sequencers, such as the Solexa's 1G sequencer, which relies upon immobilized DNA for a substrate. In one embodiment, single molecules can be amplified using PCR primers treated with moieties used for surface immobliziation, then flow the PCR positive droplets across the surface of the slide, forming a packed emulsion. The emulsion can then be broken, and the primers allowed to bind to the slide due the presence of the appropriate coating to bind the PCR products.

The Solexa 1G sequencer currently sequences amplified material that has been amplified in place, on primers bound to the slide, by bridge amplification. In this process, template DNA is flowed across the slide surface at very low concentrations, and adapters previously ligated to each template hybridize to complimentary primers attached to the slide in any one of eight lanes. Once hybridized, the primers are subjected to bridge amplification, a version of PCR amplification that utilizes immobilized primers—the product of the reaction is a patch of DNA immobilized to the slide. Several risks are encountered when amplifying DNA in this matter—the process is exquisitely sensitive to DNA concentration—if too much DNA is used, the DNA patches will be generated too closely, or even overlap, generating mixed signals during subsequent sequencing. If too little DNA is used, the DNA patches will be present at a very low density, and insufficient sequence may be generated during the run. As the sequencing reactions take 72 hours, and no titration runs are conducted to test the DNA concentrations prior to amplification, the potential loss of time and money is considerable. Additionally, neither single molecule amplification nor bridge amplification are very efficient, and bridge amplification has an upper and lower size limitation, generating products only within a particular length range.

The present invention provides methods to overcome this limitation. In one embodiment, a Solexa slide can be coated with any of the compounds commonly used to permit binding and immobilization (e.g., carboxy-esters, streptavidin, Igg, gold, etc). PCR reactions could be performed as described in the instant microfluidic device using primers modified with the appropriate binding moiety (5' amines, 5' biotins, 5' DNPs or 5' Thiols, respectively) to efficiently amplify PCR products in solution which could then be efficiently and easily bound to the Solexa slide for subsequent sequencing. The amplification is quite straight forward, conducted with a limiting dilution of template and a set of primer pairs compatible with the adapters ligated to the Solexa templates through their standard sample preparation process. One of the primer pairs would possess a 5' binding moiety as described earlier, only one of the pair as this will permit removal of the opposing strand and the generation of single stranded immobilized templates on the slide. Once amplification has been conducted, and the positive droplets sorted, the droplets can be flowed onto each of the lanes of the Solexa slide. Proper spacing between the droplets can be obtained by mixing droplets containing only buffer or immiscible oil in with the PCR positive droplets at a ratio sufficient to ensure that the PCR positive droplets are rarely proximal to each other. Once each lane has been packed with droplets, the droplets can be broken through the application of electrical field and the PCR products allowed to bind to the slide in the same geographic area that the droplet had occupied. The immobilized templates can be rendered single stranded through the application of basic washes, temperature etc. This will permit the rapid amplification of PCR fragments and their subsequent density-controlled deposition onto the Solexa chip for sequencing.

Example 6

The present invention provides methods for detecting the presence and/or sequence of nucleic acids in low copy number in droplets on a microfluidic device. The detection of a specific nucleic acid sequence present in a sample by probing the sample with a complementary sequence of nucleic acids is a well-known technique. Nucleic acids are highly specific in binding to complementary nucleic acids and are thus useful to determine whether a specific nucleic acid is present in a sample. One must know the sequence of the specific nucleic acid to be detected and then construct a probe having a complementary nucleic acid sequence to the specific nucleic acid sequence.

Since nucleic acid probes are highly specific, it is preferable in some situations to probe the nucleic acid sequence itself rather than the protein produced by the nucleic acid sequence. As a particular example, a diagnostic method based solely on protein detection would be unreliable for determining the presence of infectious particles of hepatitis B virus, due to the presence of significant levels of non-infectious antigen particles which lack the DNA genome. In another example, the various subtypes of human papilloma virus found in either pre-cancerous or benign cervical tumors can be distinguished only by the use of nucleic acid probe hybridization. Also, the specific genetic makeup of an AIDS virus makes it certain that an assay based on the presence of an AIDS virus specific nucleic acid sequence would be superior as a diagnostic.

The naturally-occurring high number of ribosomal RNA, up to 100,000 copies per cell, has been used by GenProbe to facilitate diagnosis of certain bacterial pathogens, such as Legionella and Mycoplasma, using nucleic acid probes. However, this strategy cannot be used with non-cellular pathogens, such as viruses, or with probed nucleic acid sequences with low copy numbers. Copy number is a particular problem with the development of a nucleic acid probe method for the detection of AIDS virus, where the integrated provirus may be present in less than one of ten thousand peripheral blood lymphocytes. Thus, if the particular nucleic acid sequence suspected to be present in a sample could be amplified, the copy number problem could be circumvented and probe assays could be more readily used.

In a normal biological sample, containing only a few cells, and consequently only a few copies of a particular gene, it is necessary to utilize an amplification process in order to overcome the copy number problem.

One method to amplify is to 'grow out' the sample, that is, to arrange conditions so that the living biological material present in the sample can replicate itself. Replication could increase the quantity of nucleic acid sequences to detectable levels. In the food industry, for example, in order to test processed food for the food-poisoning bacteria Salmonella, food samples must be incubated for a number of days to increase the quantity of nucleic acid copy numbers. In clinical samples, pathogens must also be allowed to increase their number by growing out over some considerable time.

Current methods utilize a process in which a sample suspected of containing a target DNA sequence is treated with oligonucleotide primers such that a primer extension product is synthesized which in turn serves as a template, resulting in amplification of the target a DNA sequence. The primer extension product is separated from the template using heat denaturation. Current methods also include a process for amplifying a target DNA sequence having two separate complementary strands. The process includes treating the strands with primers to synthesize extension products, separating the primer extension products from the templates, and in turn using the primer extension products as templates.

Both of the above methods require either manual or mechanical participation and multi-step operations by the user in the amplification process and are restricted to amplifying DNA only. The steps involved in these methods require the user to heat the sample, cool the sample, add appropriate enzymes and then repeat the steps. The temperature changes cause the enzymes to lose their activity. Hence, the user is required to repeatedly supplement the amplification mixture with aliquots of appropriate enzymes during the amplification process.

The present invention provides methods for detecting the presence and/or sequence of nucleic acids in low copy number in droplets on a microfluidic device. In one embodiment of the invention, a nucleotide/peptide nucleic acid (pna) probe (oligo probe) can be tethered such that when it binds to a template DNA molecule in low copy number located inside an aqueous emulsion (i.e., droplet) it turns on or activates an enzyme. By way of nonlimiting example, an alkaline phosphatase conjugate can be placed on one and of the low copy number nucleotide, and an inhibitor to alkaline phosphatase on the other end (like a molecular beacon). When the oligo probe binds to the low copy number template the inhibitor is removed from the enzyme and the enzyme turns over the substrate. The tethers can be a protein complementation assay wherein the binding of the oligo probe to the low copy number template causes the enzyme to be active.

Various other embodiments are described herein and should not be considered as limiting to the invention. Example 1: Taqman chews a beta-gal alpha protein attached at the 3' end of an oligo probe thereby releasing free alpha subunit to bind to omega fragment in solution. Example 2: Two oligo probes sit down on the low copy number template adjacent to each other, thereby bringing two subunits of a protein complementing assay reagent together. Example 3: A Taqman-like enzyme that releases an active moiety can also be used. The active moiety can include, for example, an enzyme that becomes activated upon release from the oligo probe, or a fluorescent group that is quenched while tethered to the oligo probe. The use of a double-strand specific nuclease that will chew up the probe only when the probe is bound, thereby releasing active enzyme or fluorescent substrates. Example 4: The probe has a fluorescent group attached such that the detected hybridization causes the release of the fluorescent group a la Taqman. Example 5: The probe has an inactive enzyme attached such that the detected hybridization causes the release of the active enzyme by a Taqman-type release. Example 6: The probe has an inactive complementing enzyme attached such that the detected hybridization causes the release of the active moiety of the enzyme to be able to complement. Example 7: Two probes have inactive enzyme moieties attached such that the detected hybridization causes the complementation and activation of the enzyme. Example 8: Two probes come together and allow a Fluorescence Resonance Energy Transfer (FRET) reaction to occur. This would require a FRET-oligo library. Almost all SNP or transcriptional profiling method may be amenable to this concept.

Many assays are conducted on microfluidic devices including, but not limited to, protein-protein, antibody-antigen, nucleic acid-protein, nucleic acid-nucleic acid, ligand-protein, ligand-nucleic acid, ligand-ligand, eukaryotic or prokaryotic cell surface moiety-second moiety, the measurement of two or more receptors on the surface of an eukaryotic or prokaryotic cell, the development of three-hybrid type systems using tandem fusions, interactor-cofactor, etc. Many other types of interactions are also known that can be adapted to the system. Assays incorporating complementation assays can be used in both proteomics and genomics.

Currently, these assay methods require methods require >10K fluorescein molecules to detect interaction/binding. In an embodiment, the present invention provides methods which reduce the number of interacting proteins by amplifying the signal of molecules that do interact. In preferred embodiments of some assays, stable emulsions may not be needed. An advantage is that we can eliminate surfactants and stabilizing additives which can affect protein activity within droplets.

Likewise, one could conceivably look for loss of complementation in any of the above assays. This loss or gain of complementation can be a function of physical (e.g., heat, light) or chemical additions to, or formulation of the droplets. These interactions include, but are not limited to, protein-protein, antibody-antigen, nucleic acid-protein, nucleic acid-nucleic acid, ligand-protein, ligand-nucleic acid, ligand-ligand, eukaryotic or prokaryotic cell surface moiety-second moiety, the measurement of two or more receptors on the surface of an eukaryotic or prokaryotic cell, the development of three-hybrid type systems using tandem fusions, interactor-cofactor, etc. Many other types of interactions are also known that can be adapted to the system. Assays incorporating complementation assays can be used in both proteomics and genomics.

The amount of each interacting partner may be with-in drop quantifiable by genetically or chemically coupling a reporter molecule (e.g., a dye or quantum dot, GFP protein) to one and or the other. Similarly, the complementation assay described for enzymatic amplification can use one of several different complementing proteins such that the concentration of each partner can be calculated within the droplet by using different enzyme substrates added to the droplets at the same or differing time. Timing of substrate addition is not critical and one of skill in the art would readily recognize that addition can be done at different times. 'Killing' by various denaturants, protease, etc is also within the purview of the skilled artisan.

In an embodiment, complementation assays can be used to add a specific addition to, for example, an IVT synthesized protein. As an example, the s-peptide of RNaseA and the S protein wherein the S peptide is genetically fused to the IVT-generated Ab and the S protein, upon binding to the S peptide activates the RNaseA activity and thereby stops further IVT synthesis. Similarly, any two complementing interactrs can be used to generate an activity.

By quantifying the amount of interactors in a droplet it may be possible to derive interaction kinetics (affinity and disassociation constants as examples). In an embodiment, the present invention provides methods which can allow the quantification of proteins below that which can be seen by fluorescent spectroscopy in the absence of amplification. Alternatively, amplification may also not be needed if one can genetically add a quantified number of reporters to the end of a molecule. For example, genetically fusing 10 GFP proteins onto the end of a protein would thereby increase the fluorescence intensity 10-fold. Similarly, a series of small complementing moieties can be fused onto the end of a protein and there obviate the need for long genetic fusions. As an example, a series of 10 s peptides spaced apart by a linker would be able to each 'grab hold' of an S protein to generate an increased signal over that which can be achieved by a single enzyme. Other examples include either biotin or biotin-binding protein mimetic and streptavidin or avidin, FLAG tags, poly histidines, complementing GFP, etc. Another example includes Qcoding the droplets.

Figure 30:
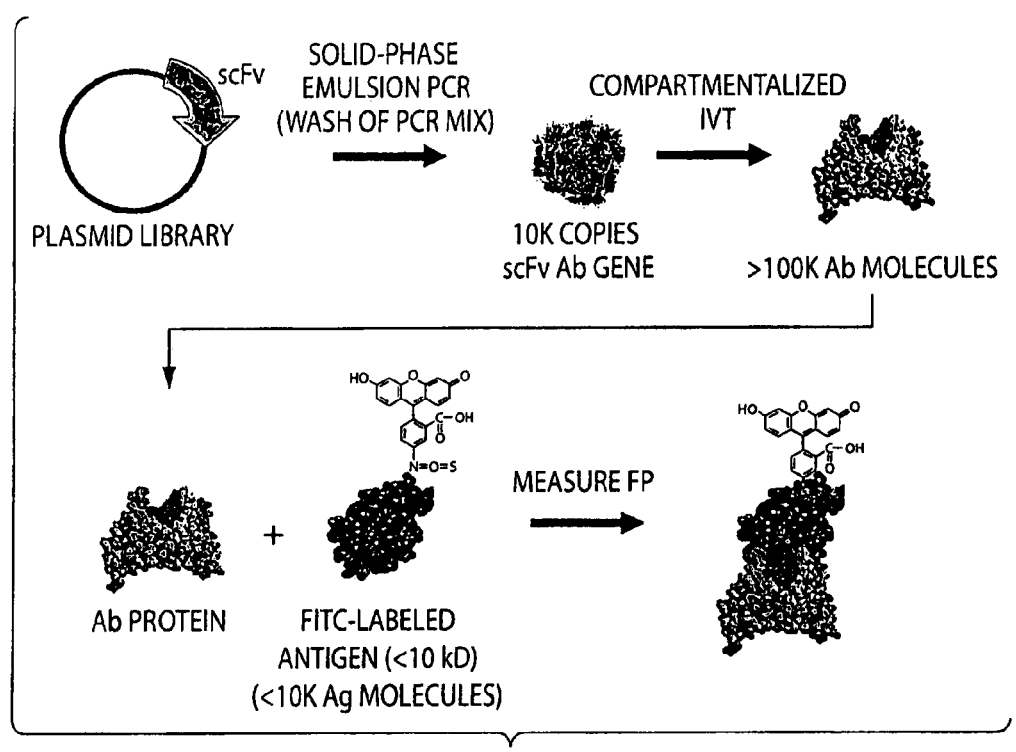
FIG. 30 shows one method for isolating antibodies on a microfluidic device.
Figure 31:
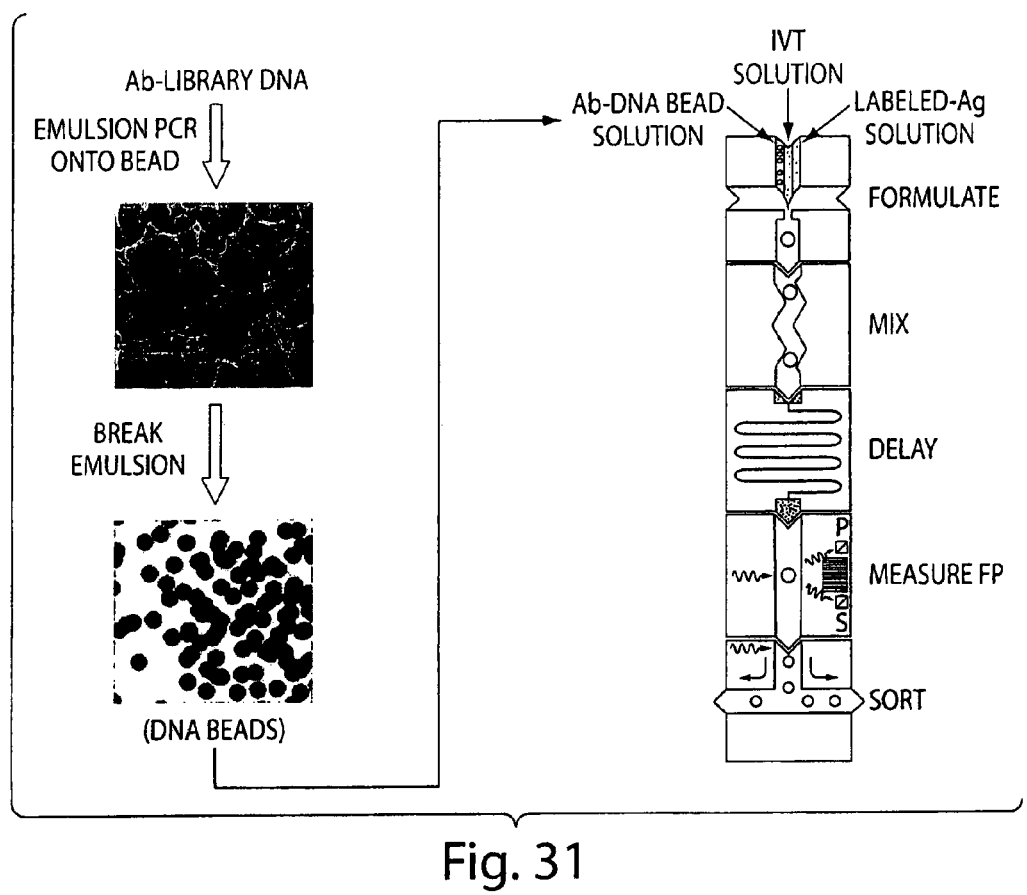
FIG. 31 shows an alternate method for isolating antibodies on a microfluidic device.

FIGS. 30 and 31 show the current method for isolating antibodies on a microfluidic device. In the current method, DNA beads are made using bulk emulsion PCR; DNA-containing beads preferably isolated before loading onto a microfluidic device. The antigen can be <20 kD, (preferably <10 kD) and labeled with an appropriate dye, (preferably with several dye-molecules). It may even be preferable to put a poly-lysine tail onto the antigen to increase signal (but be concerned about quenching). The antigen is formulated into the bead-containing droplets at a concentration of 100 nm to allow proper sensitivity in the droplet (use of multiple/different dyes may allow this concentration to drop). In some situations it is possible to add antigen at the same time as the IVT solution.

Figure 32:
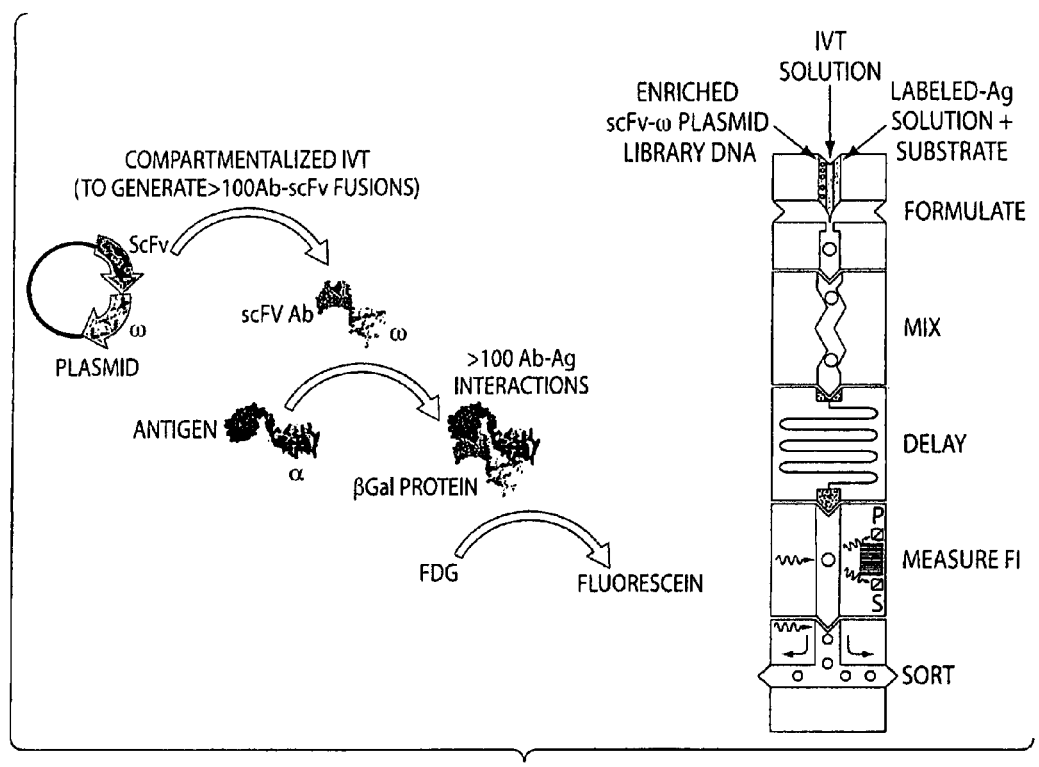
FIG. 32 shows the method of the present invention for isolating antibodies on the microfluidic device. The right panel is a diagram of individual steps proposed to amplify signal of interacting antibody and antigen. The left panel is a schematic as would be designed for a chip to be used on microfluidic device.

FIG. 32 shows the method of the present invention for isolating antibodies on the microfluidic device. The right panel is a diagram of individual steps proposed to amplify signal of interacting antibody and antigen. The left panel is a schematic as would be designed for a chip to be used on microfluidic device.

Figure 33:
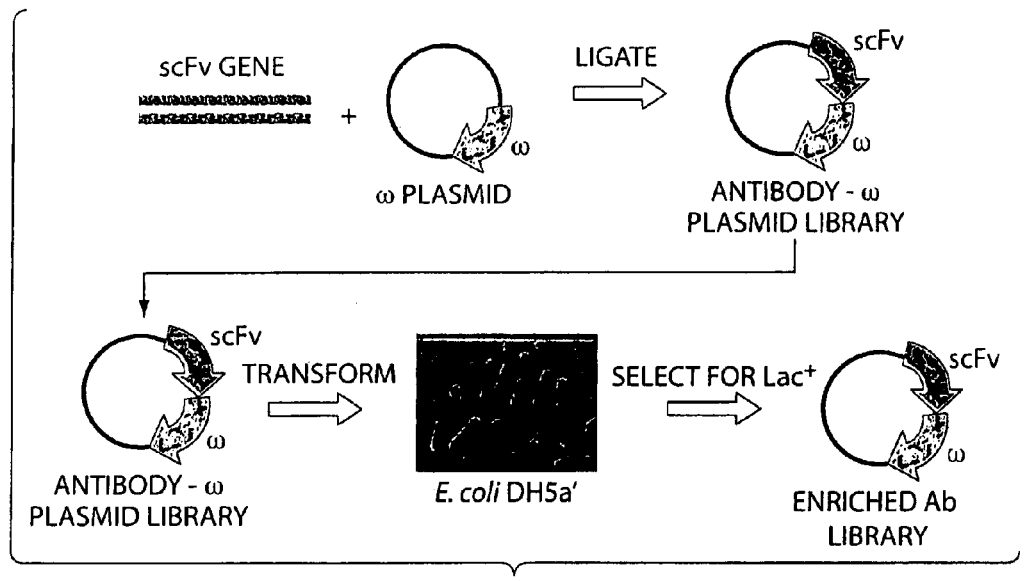
FIG. 33 shows the genetic selection for full length antibody clones. A genetic selection can be used to enrich for full-length antibody clones by transforming *E. coli* and selecting for clones able to grow on medium in which a suitable sugar is the only carbon source.

FIG. 33 shows the genetic selection for full length antibody clones. A genetic selection can be used to enrich for full-length antibody clones by transforming *E. coli* and selecting for clones able to grow on medium in which a suitable sugar is the only carbon source.

Example 7

The present invention provides a microfluidic device topology and implementation that merges the functionality of a first microfluidic substrate with that of a second microfluidic substrate by using forced withdrawal and reinjection into the same fluidic port. In current multi-step assays, the following steps must be performed to complete a "two step" experiment: (1) Installation of the first microfluidic substrate; (2) Installation of all first stage reagents; (3) Priming of all fluid lines and stabilization of the device operation; (4) Passive connection of a storage container to the instrument after device has been stabilized; (5) Disconnection of the storage container from the first device when collection complete; (6) Incubation of the collected emulsion; (7) Removal of the first device from the instrument; (8) Cleaning of the fluid lines needed for the second step of the experiment; (9) Installation of a second device to the instrument; (10) Connection of all second stage reagents, including the emulsion collected during the first stage; (11) Priming of the fluidic connections to the second device prior to running the second half of the measurement; and (12) Collection/readout of the second stage.

Figure 34:
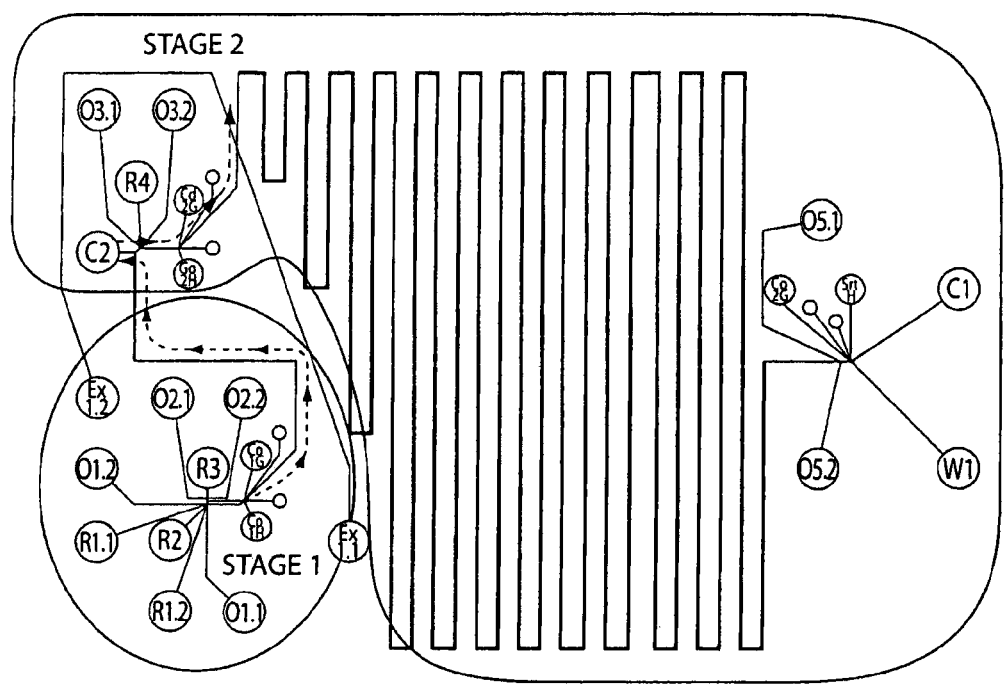
FIG. 34 is a schematic representation of a multi-step chip according to the invention. 1st stage: droplets are sent into C2, the collection port; 2nd stage: 1st stage emulsion collected into C2 is reinjected back into the chip and merged with the droplets formed in the second stage nozzle.

The methods of the present invention replaces current methodology of multi-step assays with the following: (1) Installation of the first microfluidic substrate; (2) Installation of all first and second stage reagents, including the first stage storage container (if it is not already connected); (3) Priming and stabilization of the fluidic lines and device; (4) Controlled collection of the first stage combined droplets by actively withdrawing some fraction of the oil and all of the generated emulsion into the storage container; (5) Incubation of the collected emulsion; (6) Startup and reinjection of the collected droplets back into the second half of the device; and (8) Collection/readout of the second stage. FIG. 34 depicts a schematic representation of this device topology.

Elimination of the handling of the collected emulsion has significant benefits beyond simplifying the user interaction with the instrument. Contaminants have the potential to ruin the experiment, and any extra handling and connection/disconnection increase the probability that contaminants will be introduced into the instrument.

Example 8

Gene silencing through RNAi (RNA-interference) by use of short interfering RNA (siRNA) has emerged as a powerful tool for molecular biology and holds the potential to be used for therapeutic gene silencing. Short hairpin RNA (shRNA) transcribed from small DNA plasmids within the target cell has also been shown to mediate stable gene silencing and achieve gene knockdown at levels comparable to those obtained by transfection with chemically synthesized siRNA (T. R. Brummelkamp, R. Bernards, R. Agami, Science 296, 550 (2002), P. J. Paddison, A. A. Caudiy, G. J. Hannon, PNAS 99, 1443 (2002)). Possible applications of RNAi for therapeutic purposes are extensive and include silencing and knockdown of disease genes such as oncogenes or viral genes.

Many assays are conducted on microfluidic devices are including, but not limited to, protein-protein, antibody-antigen, nucleic acid-protein, nucleic acid-nucleic acid, ligand-protein, ligand-nucleic acid, ligand-ligand, eukaryotic or prokaryotic cell surface moiety-second moiety, the measurement of two or more receptors on the surface of an eukaryotic or prokaryotic cell, the development of three-hybrid type systems using tandem fusions, interactor-cofactor, etc. Many other types of interactions are also known that can be adapted to the system. However, there is a need in the art for improved methods of RNAi screening, quickly and accurately.

The present invention provides methods for the screening of lethal and synthetic lethal RNAi-induced phenotype on a microfluidic device. The present invention utilizes a lentiviral library of RNAi where each virus has a unique 60-nt identifying barcode bracketed on either side with nucleotide sequences common to all vectors.

The analysis of lethal and synthetic lethal RNAi-induced phenotypes occurs in two steps. In the first step, the viral library is combined in bulk and infected, also in bulk, into an appropriate host strain. The molar amount of each of the different lentivirus in the library is pre-determined by sequencing on, for example, an appropriate instrument or by gene expression analysis on a microfluidic device. Post infection, the treated cells are collected and the 60-nt barcode is amplified from chromosomal DNA using PCR primers based on the bracketing sequence. In the second step, the PCR amplification product is added to a microfluidic device and analyzed against a labeled droplet library wherein the labeled droplets contain lentiviral-barcode-quantification reagents (e.g., molecular beacons, Taqman probes, etc.) against each of said lentiviral barcodes. A gene-expression analysis-like analysis is performed to quantify the amount of each lentiviral barcode-type in the treated cells. An absence or significant decrease of any lentiviral barcode in the amplified product can be assumed to be due to the death of that barcode-containing lentivirus in the treated cells. In an embodiment, the products within the droplets can also be amplified.

GFP or additional transcription analysis can also occur in two steps. In step one, the viral library is combined in bulk and infected, also in bulk, into an appropriate host strain. The molar amount of each of the different lentivirus in the library is pre-determined by sequencing on, for example, an appropriate instrument or by gene expression analysis on a microfluidic device. Post infection, the treated cells are i) collected in bulk, ii) sorted using a phenotype able to be sorted in a microfluidic device (e.g, GFP expression, cell-surface marker, low-copy cell-surface marker, etc) and iii) the 60-nt barcode is amplified from chromosomal DNA using PCR primers based on the bracketing sequence. In the second step, the PCR amplification product is added to a microfludic device and analyzed against a labeled droplet library wherein the labeled droplets contain lentiviral-barcode-quantification reagents (e.g., molecular beacons, Taqman probes, etc.) against each of said lentiviral barcodes. A gene-expression analysis-like analysis is performed to quantify the amount of each lentiviral barcode-type in the treated cells. An absence or significant decrease of any lentiviral barcode in the amplified product can be assumed to be due to the death of that barcode-containing lentivirus in the treated cells.

Example 9

Many diseases are associated with particular chromosomal abnormalities. For example, chromosomes in cancerous cells frequently exhibit aberrations called translocations, where a piece of one chromosome breaks off and attaches to the end of another chromosome. Identifying such chromosome abnormalities and determining their role in disease is an important step in developing new methods for diagnosing many genetic disorders. Traditional karyotyping using Giemsa staining allows scientists to view the full set of human chromosomes in black and white, a technique that is useful for observing the number and size of the chromosomes. However, there is a need in the art for improved methods of karyotyping, quickly and accurately.

The present invention provides methods for karyotyping. Preferably, the karyotyping screens occur within droplets on a microfluidic device. Currently, scientists cannot accurately identify many translocations or other abnormalities using only a black and white karyotype. Spectral karyotyping (SKY) is a laboratory technique that allows scientists to visualize all 23 pairs of human chromosomes at one time, with each pair of chromosomes painted in a different fluorescent color. By using SKY, they can easily see instances where a chromosome, painted in one color, has a small piece of a different chromosome, painted in another color, attached to it.

Through the use of droplet-based methods, chromosomes can be captured within droplets without having to worry about shear-forces. The chromosomes can then be passed through a 'neck-down' to stretch them out. Labeling prior to loading, with either Giemsa stain or oligonucleotide probes, can be used to karyotype the DNA as it flows.

The present invention provides methods of using SKY probes to 'paint' individual chromosomes. Also provided is a method used by flow cytometrists for the preparation of chromosomes prior to flow analysis, including flow sorting. The present invention provides methods which allow the adaptation of these methods for use on a microfluidic device.

Figure 35:
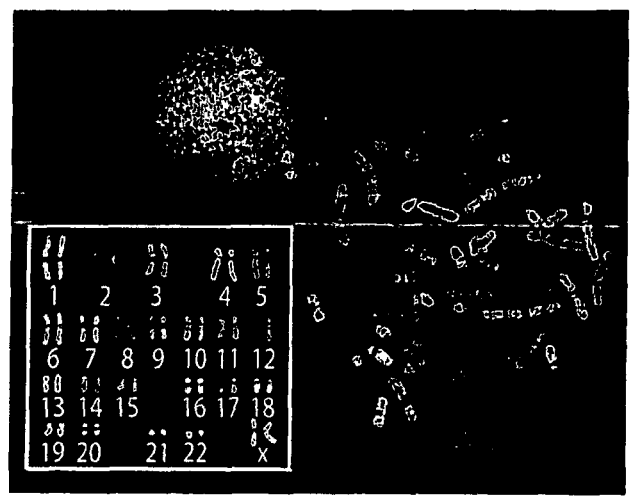
FIG. 35 shows karyotyping using spectral probes that allow all 23 pairs of human chromosomes to be seen at one time, with each pair of chromosomes painted in a difference fluorescent color.

SKY involves the preparation of a large collection of short sequences of single-stranded DNA called probes. Each of the individual probes in this DNA library is complementary to a unique region of one chromosome; together, all of the probes make up a network of DNA that is complementary to all of the chromosomes within the human genome. Each probe is labeled with a fluorescent molecule that corresponds to the chromosome to which it is complementary. For example, probes that are complementary to chromosome 1 are labeled with yellow molecules, while those that are complementary to chromosome 2 are labeled with red molecules, and so on. When these probes are mixed with the chromosomes from a human cell, the probes hybridize, or bind, to the DNA in the chromosomes. As they hybridize, the fluorescent probes essentially paint the set of chromosomes in a rainbow of colors. Scientists can then use computers to analyze the painted chromosomes to determine whether any of them exhibit translocations or other structural abnormalities. See, FIG. 35.

Prior to analysis chromosomes can be prepared as described in Bee Ling Ng and Nigel P. Carter "Factors Affecting Flow Karyotype Resolution. Cytometry" Part A 69A: 1028-1036 (2006) as follows:

1. Arrest cells at metaphase using 0.1 lg/ml demecolcine for optimal amount of time, dependent on the cell cycle time of the cell lines. (Approximately 5 h for suspension, 16 h for adherent cell lines and 4 h for LPS stimulated B lymphocyte culture).
2. Harvest cells and centrifuge at 289 g for 5 min. Remove supernatant.
3. Resuspend cell pellet in 5 ml of hypotonic solution (75 mM KCl, 10 mM MgSO4, 0.2 mM spermine, 0.5 mM spermidine, pH 8.0) and incubate at room temperature for 10 min.
4. Centrifuge cell suspension at 289 g for 5 min. Remove supernatant.
5. Resuspend cell pellet in 3 ml of ice cold polyamine isolation buffer (PAB, containing 15 mM Tris, 2 mM EDTA, 0.5 mM EGTA, 80 mM KC13 mM dithithreitol, 0.25% Triton X-100, 0.2 mM spermine, 0.5 mM spermidine, pH 7.50) and vortex for 20 s.
6. Briefly centrifuge chromosome suspensions at 201 g for 2 min. Filter supernatant through 20 lm mesh filter.
7. Stain chromosomes overnight with 5 lg/ml of Hoechst, 40 lg/ml chromomycin A3 and 10 mM MgSO4.
8. To the stained chromosome suspension, add 10 mM of sodium citrate and 25 mM of sodium sulphite 1 h before flow analysis.

The present invention also provides methods of sorting chromosomes for karyotyping wherein individual chromosomes are sorted. This sorting can be performed after chromosome-specific identification (such as hybridization of labeled probes) so as to enrich a population for one or more specific chromosomes. This enriched population can be used in DNA sequencing reactions.

The Giemsa-stained and/or labeled-probe-hybridized chromosomes can be sent through a constriction of a channel on a microfluidic device to detect the areas of stain and/or label as a genetic 'bar-code' to identify regions of translocation, etc. on individual chromosomes. Identification of chromosomes and karyotyping can be used after enrichment of specific cell-types, for example i) fetal cells from maternal blood, or ii) cancer cells from human blood.

Example 10

The present invention provides microbial strains with improved biomass conversion and methods of preparing such strains. Biomass is organic matter such as plant matter, i.e., trees, grasses, agricultural crops, or other biological material such as animal material. It can be used as a solid fuel, or converted into liquid or gaseous forms, for the production of electric power, heat, chemicals, or fuels. Biomass can also be used in formulating other commercial products in other industrial sectors such as textiles, food supply, environmental, communication, housing, etc. For example, biofuel development seeks the development of new microbial strains with improved biomass conversion to ethanol.

Researchers have been applying sophisticated metabolic engineering techniques to develop microorganisms that can more effectively ferment the sugars in biomass. Lignocellulosic biomass contains five carbon sugars such as xylose (from the hemicellulose) as well as the more "common" six carbon sugars such as glucose found in grains. This makes fermentation and other bioprocessing far more challenging. While some biorefinery scenarios will take advantage of the different sugar streams to produce multiple products, others will be more cost effective if all the sugars can coferment in a single set of equipment. Accordingly, researchers are developing microorganisms that can coferment all the sugars in biomass in order to improve ethanol production economics. With industrial partners, researchers are working to develop designer strains of microorganisms for biomass conversion of specific feedstocks, feedstreams, and processes. Thus, there is a need for devices and methods for the rapid engineering of new microbial strains with improved biomass conversion.

The present invention provides a microfluidic device in which to formulate a mutant bacterial, yeast, or fungi strain which can be used for biomass energy conversion. The microorganism strain can be engineered, e.g., by recombinant methods, to include at least one nucleic acid sequence encoding one or more polypeptides of interest, wherein the mutant strain expresses the polypeptides of interest at a higher level than the corresponding non-mutant strain under the same conditions.

In one embodiment, the nucleic acid sequence can be operably linked to an expression-regulating region selected from the group consisting of a promoter sequence associated with cellulase expression, xylanase expression, or gpdA expression. In another embodiment, the nucleic acid sequence can further be optionally linked to a secretion signal sequence.

In one embodiment, the nucleic acid sequence can be a heterologous nucleic acid sequence selected from heterologous polypeptide-encoding nucleic acid sequences, heterologous signal sequences, or heterologous expression-regulating sequences, or combinations thereof. For instance, the nucleic acid sequence can be a heterologous signal sequence, e.g., a secretion signal sequence. Alternatively, the nucleic acid sequence can be a heterologous expression-regulating region, e.g. an inducible promoter or a high expression promoter.

The polypeptides of interest can be homologous peptides and are expressed in the mutant strain at a higher level than in the corresponding non-mutant strain under the same conditions. In one embodiment, the polypeptides of interest can be selected from one or more of carbohydrate-degrading enzymes, proteases, lipases, esterases, other hydrolases, oxidoreductases, and transferases. In yet another embodiment, the polypeptides of interest can be selected from one or more of fungal enzymes that allow production or overproduction of primary metabolites, organic acids, secondary metabolites, and antibiotics. These fungal sequences can include secretion signal sequences, for example, and can be selected from one or more of cellulase, P-galactosidase, xylanase, pectinase, esterase, protease, amylase, polygalacturonase or hydrophobin. Alternatively, the fungal sequences can include one or more fungal expression-regulating regions. Preferably, the polypeptides of interest exhibit optimal activity and/or stability at a pH above 6, and/or have more than 70% of its activity and/or stability at a pH above 6.

The mutant microorganism can further include a selectable marker. The selectable marker can confer resistance to a drug, for example, or relieve a nutritional defect.

In another embodiment, the microorganism can be mutated via mutagenesis. Mutagenesis can be achieved, for example, by one or both of UV irradiation or chemical mutagenesis. For example, in one embodiment mutagenesis can include exposing a microorganism to UV irradiation, exposing it to N-methyl-N'-nitro-N-nitrosoguanidine, and exposing it again to UV irradiation.

The present invention also provides methods for creating microbial strains with improved biomass conversion. In one embodiment, the method includes providing a microfluidic device made of a microfabricated substrate. The microfabricated substrate can have a plurality of electrically addressable, channel bearing modules integrally arranged so as to be in fluid communication with each other, thereby forming at least one main channel adapted to carry at least one continuous phase fluid. The method further includes flowing a buffer, a microbe library, and a media (either in separate solutions or all together in one solution) through a first inlet channel into the main channel of the microfabricated substrate such that one or more droplets is formed in the continuous phase fluid; flowing a substrate through a second inlet channel into the main channel of the microfabricated substrate such that one or more droplets is formed in said continuous phase fluid; coalescing the droplets containing the microbe library with the droplets containing the substrate as the droplets pass through a coalescence module, thereby producing a NanoRefinery; interrogating the NanoRefinery for a predetermined characteristic within a detection module on the microfabricated substrate; and collecting the NanoRefineries containing the microbes of interest in a collection module on the microfabricated substrate. An assay system, e.g., a means by which to determine whether a desired product has been produced, or a means by which to determine the absence of a starting substrate material, can also be incorporated into one of the droplets or the NanoRefinery. The assay system can be added either before, after, or simultaneously with the addition of the substrate.

In one embodiment, the assay system is a dye that can measure the amount of sugar in a solution. In another embodiment, the microbe library can include one or more of DNA, bacteria, yeast or fungi. The substrate can include biomass, which can include one or more of fermentation broth, cellulose or other polysaccharide, or plant lignan.

Figure 36:
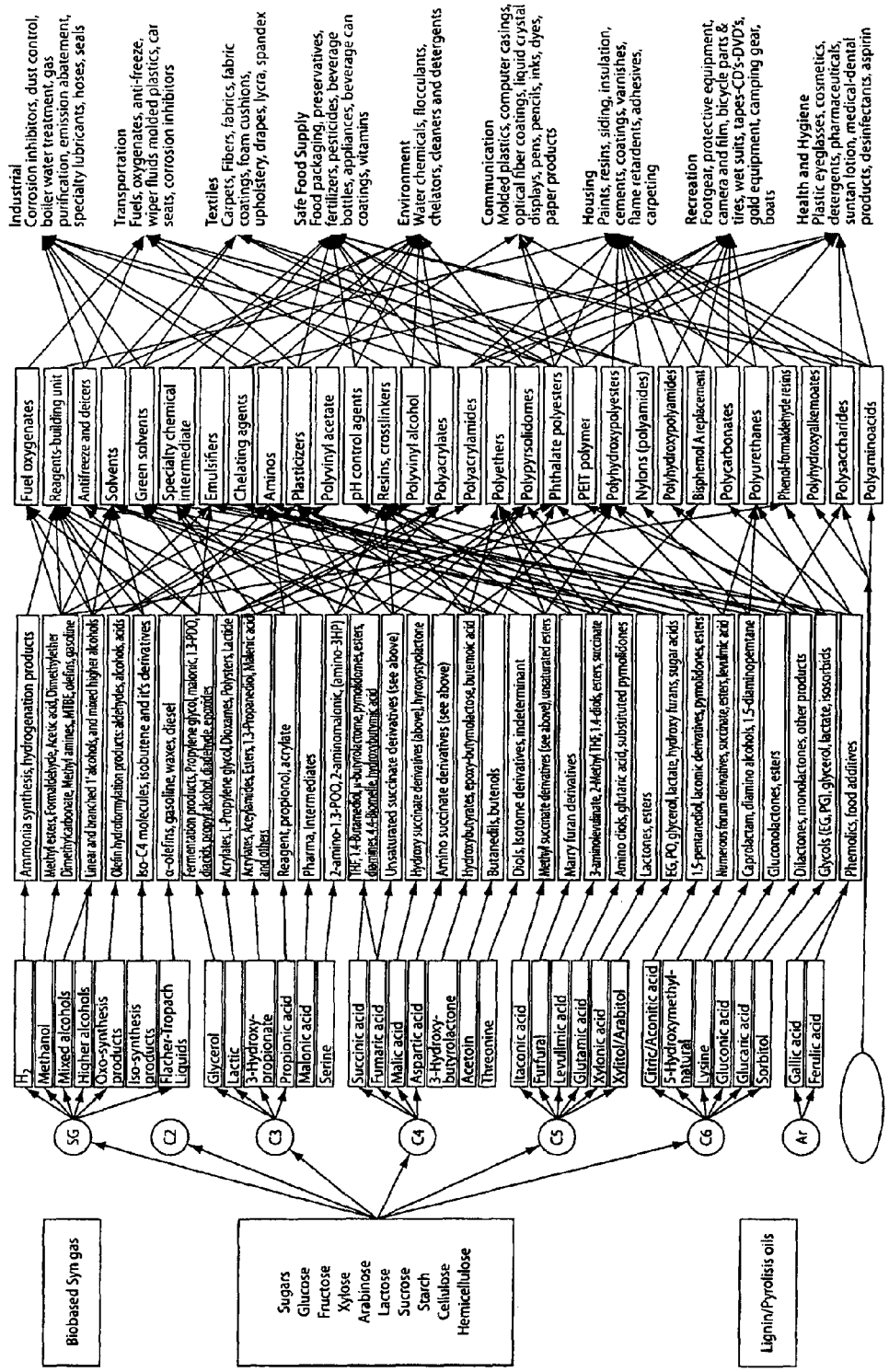
FIG. 36 shows the future BioBased Economy with six building blocks based on renewable biomass.
Figure 37:
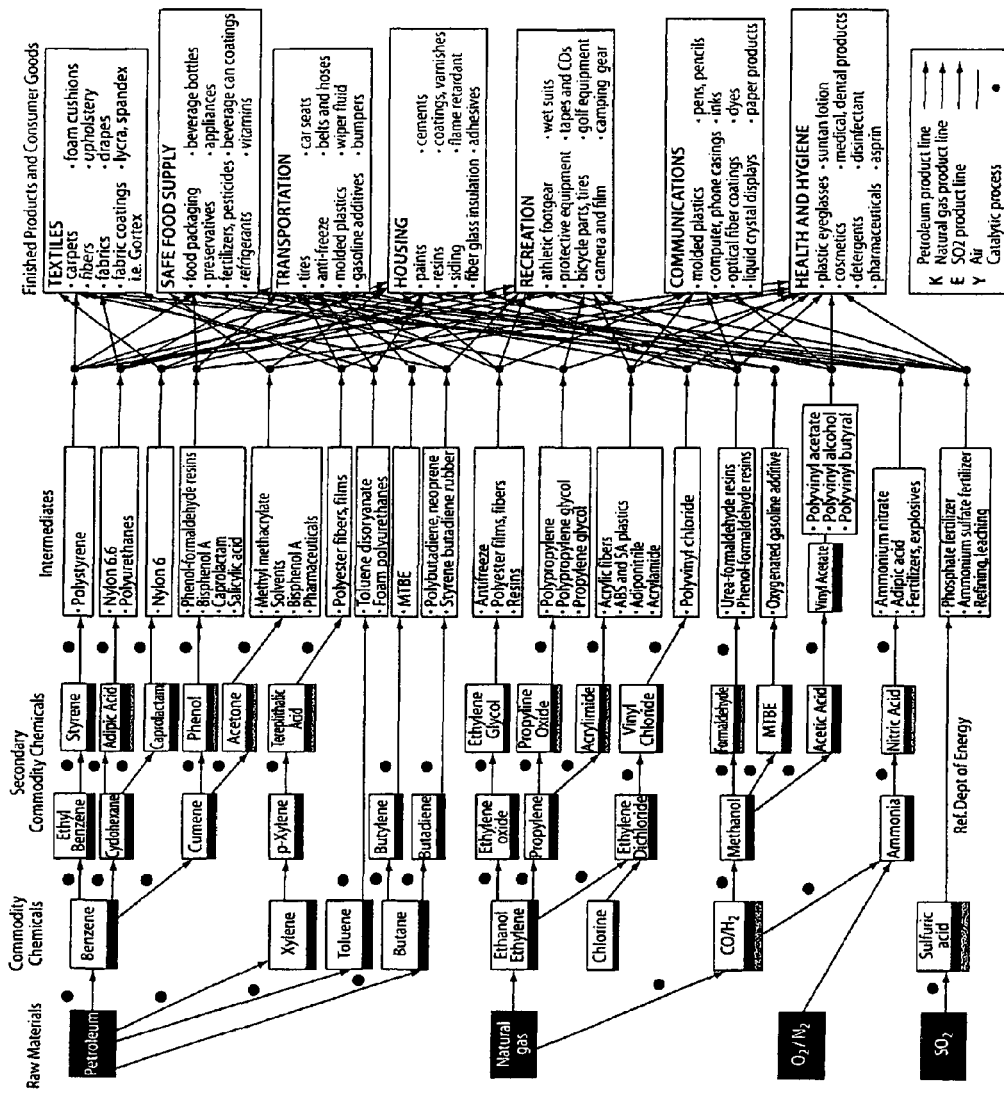
FIG. 37 shows the 8 non-renewable building blocks based on petroleum.

The present invention further provides methods for degrading or converting biomass into one or more products. In one embodiment, the method includes treating the biomass with an effective amount of a recombinant microorganism, wherein the recombinant microorganism expresses or overexpresses one or more heterologous sequences encoding enzymes that degrade or convert the biomass into one or more products. In one embodiment, the biomass can include plant cell wall polysaccharides. In another embodiment, the products can include one or more of the commodity chemicals or secondary commodity chemicals used to produce one or more of the Intermediates or finished products and consumer goods listed in FIGS. 36 and 37.

Example 11

The present invention provides methods of screening for enzymes with improved activity. As an example, at least one cell (prokaryotic or eukaryotic) is deposited into a droplet and the cells are allowed to secrete a substance for which a homogeneous assay is available. For a specific example, an individual *Bacillus subtilis* cell from a mutagen-treated culture is deposited within a 30 micron growth-medium containing droplet, the resulting droplets are collected and allowed to incubate overnight. The bacterium secretes a protease into the droplet. The droplets containing the Bacilli are then individually merged with an assay droplet containing a protease-cleavable dye-labeled peptide. The uncleaved peptide is colorless, while the cleaved peptide becomes red. The droplets are incubated on chip for a sufficient time such as to allow color formation. Droplets that are red are sorted. The collected sorted droplets are then plated onto solid growth medium and the resulting colonies, after overnight incubation, represent individual clonal isolates from the droplets.

In addition, the assay droplets can be sorted based upon a specific activity, for example enzymes that are more active, indicated by a more intense red droplet after a specific period of time. In addition, the conditions within the droplet can be changed during the merging of the two droplets to assay conditions which may itself not be permissive for the bacteria. For example the pH within the droplet is altered in order to find mutant enzymes that work better under either acidic or alkaline conditions. Or the droplets can be heated such that enzymes that are more heat resistant are identified.

The merging of the droplets can be right after the individual cell is placed into the droplet or after further incubation.

Another method of the instant invention is as described above, except that the cells are lysed before the assay step in order to release the contents of the cell into the droplet.

In other embodiments, the substrate can be added with— or simultaneously formulated from two or more separate reagent streams with the contained within a droplet. For a specific example, macrophage cells are washed in buffer and incubated with an enzyme-conjugated anti-cell-surface antibody. The cells are then individually loaded into droplets formulated at the same time, with the enzyme substrate. The amount of enzyme substrate turned over within the droplet will be proportional to the number of enzyme molecules within the droplet, which is proportional to the number of antibodies bound to the macrophage surface. By careful calibration it should be possible to estimate the number of cell-surface molecules attached to the cell surface.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

What is claimed is:

1. A method of reducing contamination associated with sample handling, comprising:
   providing an aqueous fluid comprising a sample through a sample inlet;
   providing an immiscible fluid flowing through a main channel that is in fluidic communication with the sample inlet, wherein the main channel is in a horizontal plane;
   partitioning the aqueous fluid with the immiscible fluid to form a plurality of droplets in the main channel, wherein at least one droplet comprises a sample;
   flowing the droplets toward a downstream separation chamber that is in fluidic communication with the main channel,
   wherein the separation chamber has a wider cross-section than the main channel cross-section and the separation chamber is disposed perpendicular to the main channel; and
   separating the plurality of droplets from the immiscible fluid in the separation chamber based on the different densities of the droplets and the immiscible fluid.

2. The method of claim 1, further comprising collecting the separated droplets.

3. The method of claim 1, wherein the separated droplets are collected in a vessel.

4. The method of claim 3, wherein the vessel is a PCR tube or a test tube.

5. The method of claim 3, after the partitioning step, further comprising introducing one or more reagents to the droplets.

6. The method of claim 5, wherein the one or more reagents are amplification reagents.

7. The method of claim 6, wherein the one or more amplification reagents are for a polymerase chain reaction.

8. The method of claim 5, wherein the one or more reagents are introduced by merging a droplet comprising one or more reagents with a droplet comprising a sample.

9. The method of claim 5, after the reagent introducing step, further comprising sorting the droplets.

10. The method of claim 1, wherein the sample comprises a biological material.

11. The method of claim 10, wherein the biological material is selected from the group consisting of a tissue, cell, particle, protein, antibody, amino acid, nucleotide, small molecule, and pharmaceutical.

12. The method of claim 11, wherein the biological material further comprises one or more labels.

13. The method of claim 12, wherein the one or more labels are DNA tags, dyes, quantum dot, or combination thereof.

14. A method of reducing sample loss associated with sample handling, comprising:
   providing an aqueous fluid comprising a sample through a sample inlet;
   providing an immiscible fluid flowing through a main channel that is in fluidic communication with the sample inlet, wherein the main channel is in a horizontal plane;
   partitioning the aqueous fluid with the immiscible fluid to form a plurality of droplets in the main channel;
   flowing the droplets toward a downstream separation chamber that is in fluidic communication with the main channel, wherein the separation chamber has a wider cross-section than the main channel cross-section and the separation chamber is disposed perpendicular to the main channel; and separating the plurality of droplets from the immiscible fluid in the separation chamber based on the different densities of the droplets and the immiscible fluid.

15. The method of claim 14, after the separation step, further comprising placing the droplets onto a second continuous phase carrier fluid.

16. The method of claim 15, wherein the second continuous phase carrier fluid comprises a de-stabilizing surfactant.

17. The method of claim 15, after the placing step, further comprising destabilizing the droplets.

* * * * *

(12) INTER PARTES REVIEW CERTIFICATE (2424th)
United States Patent
Link

(10) Number: US 9,896,722 K1
(45) Certificate Issued: Oct. 8, 2021

(54) SYSTEMS FOR HANDLING MICROFLUIDIC DROPLETS

(71) Applicant: Darren Roy Link

(72) Inventor: Darren Roy Link

(73) Assignee: BIO-RAD LABORATORIES, INC.

Trial Numbers:

IPR2020-00088 filed Oct. 25, 2019
IPR2020-00089 filed Oct. 25, 2019

Inter Partes Review Certificate for:

Patent No.: 9,896,722
Issued: Feb. 20, 2018
Appl. No.: 15/415,044
Filed: Jan. 25, 2017

The results of IPR2020-00088 and IPR2020-00089 are reflected in this inter partes review certificate under 35 U.S.C. 318(b).

INTER PARTES REVIEW CERTIFICATE
U.S. Patent 9,896,722 K1
Trial No. IPR2020-00088
Certificate Issued Oct. 8, 2021

AS A RESULT OF THE INTER PARTES REVIEW PROCEEDING, IT HAS BEEN DETERMINED THAT:

Claims 15-17 are found patentable.

Claims 1-7 and 10-14 are cancelled.

\* \* \* \* \*